US006251897B1

(12) United States Patent
Ina et al.

(10) Patent No.: US 6,251,897 B1
(45) Date of Patent: Jun. 26, 2001

(54) 6-PHENYLTETRAHYDRO-1,3-OXAZIN-2-ONE DERIVATIVE AND PHARMACEUTICAL COMPOSITION CONTAINING THE SAME

(75) Inventors: Shinji Ina; Kenjirou Yamana; Kyoji Noda, all of Omiya (JP)

(73) Assignee: Nikken Chemicals Co., LTD, Tokyo (JP)

( * ) Notice: Subject to any disclaimer, the term of this patent is extended or adjusted under 35 U.S.C. 154(b) by 0 days.

(21) Appl. No.: 09/230,869

(22) PCT Filed: Jul. 30, 1997

(86) PCT No.: PCT/JP97/02654

§ 371 Date: Feb. 1, 1999

§ 102(e) Date: Feb. 1, 1999

(87) PCT Pub. No.: WO98/04534

PCT Pub. Date: Feb. 5, 1998

(30) Foreign Application Priority Data

Jul. 31, 1996 (JP) .................................................. 8-216926

(51) Int. Cl.⁷ .......................... A61K 31/535; A61P 11/06; A61P 17/04; C07D 265/10
(52) U.S. Cl. ............................ 514/228.8; 544/96; 544/97
(58) Field of Search ..................... 544/97, 96; 514/228.8

(56) References Cited

U.S. PATENT DOCUMENTS

| 4,193,926 | 3/1980 | Schmiechen et al. ............ 260/326.5 |
| 5,128,358 | 7/1992 | Saccomano et al. ................ 514/392 |
| 5,459,145 | 10/1995 | Saccomano et al. ................ 514/274 |

FOREIGN PATENT DOCUMENTS

| 50-157360 | 12/1975 | (JP) . |
| 62-281864 | 12/1987 | (JP) . |
| 5-117239 | 5/1993 | (JP) . |
| 5-148248 | 6/1993 | (JP) . |
| 5-213893 | 8/1993 | (JP) . |
| 6-17777 | 1/1994 | (JP) . |
| 7-17946 | 1/1995 | (JP) . |
| 7-101861 | 4/1995 | (JP) . |
| WO 94/10118 | 5/1994 | (WO) . |
| WO 94/12461 | 6/1994 | (WO) . |
| WO 95/03794 | 2/1995 | (WO) . |
| WO 95/08534 | 3/1995 | (WO) . |

OTHER PUBLICATIONS

Eur. Respir. J., 7, 579 (1994) (on order).
Trends Pharm., Sci., 12, 19 (1991) (on order).
Thorax, 46, 512 (1991) (on order).
J. Pharmacol. Exp. Ther., 266, 306 (1993) (on order).
Br. J. Pharmacol., 112, 332 (1994) (on order).
Nature Medicine, 1, 244 (1994) (on order).
Clin. Exp. Immunol., 100, 126 (1995) (on order).
Barnes et al.; "Theoplhylline in the Management of Asthma: Time for Reappraisal"; Eur. Respir. J., vol. 7, pp. 579–591 (1994) U.K.

Nicholson et al.; "Differential Modulation of Tissue Function and Therapeutic Potential of Selective Inhibitors of Cyclic Nucleotide Phosphodiesterase Isoenzymes"; TIPS (1991), vol. 12, pp. 19–27, U.K.
Torphy et al.; "Phosphodiesterase Inhibitors: New Opportunities for the Treatment of Asthma"; Thorax, vol. 46, pp. 512–523 (1991) U.S.
Underwood et al.; "Inhibition of Antigen–Induced Bronchoconstriction and Eosinophil Infiltration in the Guinea Pig by the Cyclic AMP–Specific Phosphodiesterase Inhibitor, Rolimpram"; J. Pharmacol. Exp. Ther., vol. 266 No. 1, pp. 306–313 (1993) U.S.
Teixeira et al.; "Effects of Phosphodiesterase Isoenzyme Inhibitors on Cutaneous Inflammation in the Guinea–Pig"; Br. J. Pharmacol., vol. 112, pp. 332–340 (1994) U.S.
Sommer et al.; "The Antidepressant Rolipram Suppresses Cytokine Production and Prevents Autoimmune Encephalomyelitis";Nature Medicine, vol. 1, pp. 244–249 (1995) U.S.
Sekut et al.; "Anti–Inflammatory Activity of Phosphodiesterase (PDE)–IV Inhibitors in a...and Chronic Models of Inflammation",Clin. Exp. Immunol., vol. 100, pp. 126–132 (1995) U.S.

Primary Examiner—Richard L. Raymond
Assistant Examiner—Venketaraman Balasubramanian
(74) Attorney, Agent, or Firm—Christie, Parker & Hale, LLP

(57) ABSTRACT

A 6-phenyltetrahydro-1,3-oxazin-2-one derivative having the formula (I):

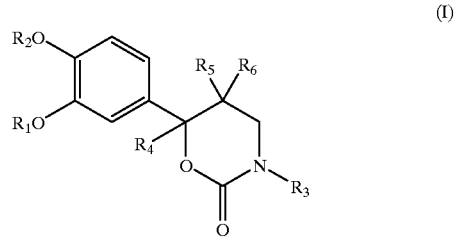

(I)

wherein, $R_1$ is an unsubstituted or substituted $C_1$ to $C_8$ alkyl group; an unsubstituted or substituted $C_3$ to $C_7$ cycloalkyl group;, etc., $R_2$ is a $C_1$ to $C_4$ alkyl group, $R_3$ is H; an unsubstituted or substituted $C_1$ to $C_5$ alkyl group; etc., $R_4$ is H; an unsubstituted or substituted $C_1$ to $C_6$ alkyl group, and $R_5$ and $R_6$ are independently a hydrogen atom; an unsubstituted or substituted $C_1$ to $C_5$ alkyl group; etc. an optical isomer thereof, or a pharmacologically acceptable salt thereof, or a hydrate or a solvate thereof and pharmaceutical compositions containing the same, in particular a drug for the prevention or treatment of inflammatory diseases and a drug for asthma.

The above 6-phenyltetrahydro-1,3-oxazin-2-one derivative has a strong type IV PDE inhibitory activity and has a bronchiodilator and antiinflammatory effects.

20 Claims, No Drawings

6-PHENYLTETRAHYDRO-1,3-OXAZIN-2-ONE DERIVATIVE AND PHARMACEUTICAL COMPOSITION CONTAINING THE SAME

TECHNICAL FIELD

The present invention relates to a novel 6-phenyltetrahydro-1,3-oxazin-2-one derivative having a type IV phosphodiesterase (PDE) inhibitory activity and a pharmaceutical composition containing the same.

BACKGROUND ART

Intracellular second messenger cAMP is involved in relaxation of airway smooth muscles and regulation of the functions of inflammatory cells. cAMP is broken down by phosphodiesterase (PDE) and becomes inactive 5'-AMP. It is considered that an increase in intracellular concentration of cAMP due to suppression of cAMP metabolism by PDE would give bronchodilating and anti-inflammatory actions and would exhibit a therapeutic effect on inflammatory diseases such as asthma [Eur. Respir. J., 7, 579 (1994)]. Up to now, PDE has been classified into five isozymes (i.e., types I to V PDE). Their distributions differ among on the tissue [Trends Pharm., Sci., 12, 19 (1991)]. This suggests a possibility that selective inhibitors of PDE isozymes would result in tissue specific increase of intracellular cAMP concentration.

It is reported that a selective inhibitor of type IV PDE isozyme suppresses inflammatory cells functions [Thorax, 46, 512 (1991)] and is useful for inflammatory diseases such as asthma [J. Pharmacol. Exp. Ther., 266, 306 (1993)] and dermatitis [Br. J. Pharmacol., 112, 332 (1994)] and autoimmune diseases such as multiple sclerosis [Nature Medicine, 1, 244 (1994)] and rheumatoid arthritis [Clin. Exp. Immunol., 100, 126 (1995)]. In addition, it is thought that cardiovascular side effect caused by non-selective PDE inhibitors such as theophylline could be reduced by using selective type IV PDE inhibitor. Rolipram having the following formula (Japanese Unexamined Patent Publication (Kokai) JP-A-50-157360) is known as a compound having a specific inhibitory activity against type IV PDE.

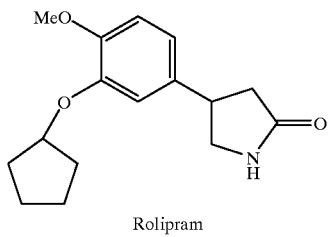

Rolipram

Other compounds having a specific inhibitory activity against type IV PDE are known (JP-A-62-281864, U.S. Pat. No. 5128358, WO 94/10118, WO 94/12461, JP-A-5-117239, JP-A-7-101861, WO 95/03794, WO 95/08534, etc.), but they have not been clinically applied up to now. Development of more useful compounds is desired. Further, JP-A-5-213893, discloses, as an antifungal agent, a compound having the following formula (II):

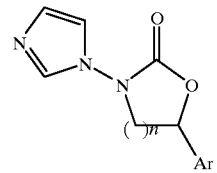

(II)

wherein, Ar represents an unsubstituted or substituted aryl group or heterocycle and n is 1 or 2. JP-A-6-1777 discloses, as an antifungal agent, a compound the following formula (III):

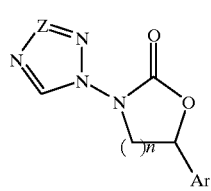

(III)

wherein, Ar represents an unsubstituted or substituted aryl group or a heterocyclic ring, n is 1 or 2, and Z is N or CH. JP-A-5-148248 discloses a compound having the following formula (IV):

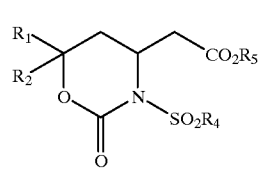

(IV)

wherein, $R_1$ and $R_2$ may be the same or different and represents a hydrogen atom or an unsubstituted or substituted phenyl group, $R_4$ is an unsubstituted or substituted $C_1$ to $C_{10}$ alkyl group, $R_5$ represents a $C_1$ to $C_{10}$ alkyl group, and n is 0 or 1, as a compound useful for the production of a carbapenem based antibiotic or carbacephem based antibiotic. JP-A-7-17946 discloses a compound having formula (V):

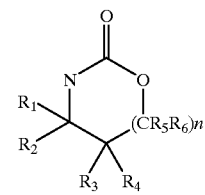

(V)

wherein, $R_1$ to $R_6$ each independently represent hydrogen; a $C_1$ to $C_4$ alkyl group; a hydroxy group; a $C_1$ to $C_4$ alkoxy group or a $C_1$ to $C_4$ alkyl group substituted with a —$SO_3H$ group; a phenyl group; a benzyl group; a halogen atom; a phenyl group substituted with a $C_1$ to $C_4$ alkoxy group or a —$SO_3H$ group; a benzyl group; and n is 0 or 1, as a starting material, when producing 2-(2'-aminoalkylmercapto) ethanol useful as a synthesis intermediate for a dye.

DISCLOSURE OF THE INVENTION

An object of the present invention is to provide a novel compound having a type IV phosphodiesterase (PDE)

inhibitory activity and a pharmaceutical composition containing the same.

In accordance with the present invention, there are provided a 6-phenyltetrahydro-1,3-oxazin-2-one derivative having the formula (I):

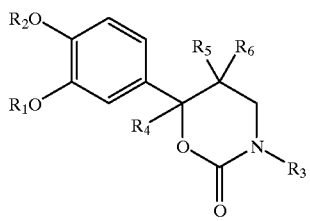

wherein, $R_1$ represents an unsubstituted or substituted $C_1$ to $C_8$ alkyl group; an unsubstituted or substituted $C_3$ to $C_7$ cycloalkyl group; an unsubstituted or substituted heterocycle; or a polycyclic hydrocarbon, $R_2$ represents a $C_1$ to $C_4$ alkyl group, $R_3$ is a hydrogen atom; an unsubstituted or substituted $C_1$ to $C_5$ alkyl group; an unsubstituted or substituted $C_3$ to $C_7$ cycloalkyl group; an unsubstituted or substituted aryl group; an unsubstituted or substituted heteroaryl group which contains at least one hetero atom selected from the group consisting of an oxygen atom, nitrogen atom, and sulfur atom; or acyl group, $R_4$ is a hydrogen atom; an unsubstituted or substituted $C_1$ to $C_6$ alkyl group; an unsubstituted or substituted aryl group; an unsubstituted or substituted heteroaryl group which contains at least one hetero atom selected from the group consisting of an oxygen atom, a nitrogen atom, and a sulfur atom, and $R_5$ and $R_6$ are independently a hydrogen atom; an unsubstituted or substituted $C_1$ to $C_5$ alkyl group; an unsubstituted or substituted $C_3$ to $C_7$ cycloalkyl group; or an unsubstituted or substituted aryl group which may contain at least one hetero atom selected from the group consisting of an oxygen atom, a nitrogen atom, and a sulfur atom an optical isomer or a pharmacologically acceptable salt thereof, or a hydrate thereof or a solvate thereof.

In accordance with the present invention, there is provided a pharmaceutical composition comprising, as an essential ingredient, the above derivative, an optical isomer or a pharmacologically acceptable salt thereof, or a hydrate thereof or a solvate thereof, specifically an agent for the prevention or treatment of inflammatory diseases or an antiasthmatic agent.

BEST MODE FOR CARRYING OUT THE INVENTION

The present inventors conducted a search for a novel compound having a type IV PDE inhibitory activity and, as a result, found that the above 6-phenyltetrahydro-1,3-oxazin-2-one derivative had a strong type IV PDE inhibitory activity and had a bronchodilator and antiinflammatory effects, whereby the present invention was completed.

The present invention will now be explained in detail.

As the $C_1$ to $C_8$ linear or branched alkyl group of $R_1$ of the compound having the above formula (I), methyl, ethyl, propyl, isopropyl, n-butyl, 2-methylpropyl, sec-butyl, t-butyl, n-pentyl, 1,1-dimethylpropyl, n-hexyl, 1-methylpentyl, 1,1-dimethylbutyl, 2-ethylbutyl, n-heptyl, n-octyl group, etc. may be mentioned. These may be substituted with a halogen atom; a hydroxy group; a nitro group; a cyano group; an amino group; a carboxyl group; an aryl group such as phenyl, tolyl or napthyl; a heteroaryl group such as pyridyl, thiazolyl, thienyl, furyl, or quinolyl; a cycloalkyl group such as cyclopropyl, cyclobutyl, cyclopentyl, or cyclohexyl; haloalkyl; carbamoyl; alkoxy; alkylcarbonyl, etc. As the substituted $C_1$ to $C_8$ alkyl group, for example, cyclopropylmethyl, cyclobutylmethyl, cyclopentylmethyl, cyclohexylmethyl, 1-methylcyclopropylmethyl, 1-phenylcyclopropylmethyl, benzyl, phenethyl, 4-fluorophenethyl, 3-phenylpropyl, 4-phenylbutyl, 5-phenylpentyl, 2-(1-naphthyl)ethyl, 2-(2-pyridyl)ethyl, 2-(4-methyl-5-thiazolyl)ethyl, 2-(benzyloxy) ethyl, 2-(phenethyloxy)ethyl, 2-(methoxy)ethyl, 3-(methoxy)propyl, 4-(methoxy)butyl, 2-(ethoxy)ethyl, 3-(ethoxy)propyl, 2-(butoxy)ethyl, 2-(cyclopropylmethyloxy)ethyl, 2-(cyclopentyloxy)ethyl, 2-(4-methyl-1-piperazinyl)ethyl, 3-(4-benzyl-1-piperazinyl) propyl, etc. may be mentioned.

As the $C_3$ to $C_7$ cycloalkyl group of $R_1$, cyclopropyl, cyclobutyl, cyclopentyl, cyclohexyl, cycloheptyl, etc. may be mentioned. This may be substituted with an alkyl group; a halogen atom; a hydroxy group; a nitro group; a cyano group; an amino group; a carboxyl group; an aryl group such as phenyl, tolyl or napthyl; a heteroaryl group such as pyridyl, thiazolyl, thienyl, furyl, or quinolyl; a cycloalkyl group such as cyclopropyl, cyclobutyl, cyclopentyl, or cyclohexyl; a haloalkyl group; a carbamoyl group; an alkoxy group; an alkylcarbonyl group, etc. As the substituted $C_3$ to $C_7$ cycloalkyl group, for example, 4-phenylcyclohexyl, 1-methylcyclopentyl, or 3-methylcyclopentyl may be mentioned.

As the heterocyclic ring of $R_1$, a pyridyl group; a thiazolyl, furyl, thienyl, tetrahydrofuryl, piperidyl, etc. may be mentioned. These may be substituted with an alkyl group; a halogen atom; a hydroxy group; a nitro group; a cyano group; an amino group; a carboxyl group; an aryl group such as phenyl, tolyl or napthyl; a heteroaryl group such as pyridyl, thiazolyl, thienyl, furyl, or quinolyl an aralkyl group such as benzyl, phenethyl, 1-naphthylmethyl, or 4-pyridylmethyl; a cycloalkyl group such as cyclopropyl, cyclobutyl, cyclopentyl, or cyclohexyl; a haloalkyl; a carbamoyl; an alkoxy group; an alkylcarbonyl group, etc. As the substituted heterocycle, for example, 1-benzyl-4-piperidyl, 2-nitropyridyl, or 3-tetrahydrofuryl may be mentioned.

As the polycyclic hydrocarbon of $R_1$, a dibenzocycloheptyl or indanyl may be mentioned.

As $R_1$, preferably a $C_1$ to $C_6$ alkyl group; a $C_1$ to $C_5$ alkyl group substituted with a group selected from the group consisting of an unsubstituted or substituted aryl group an unsubstituted or substituted heteroaryl group which contains at least one hetero atom selected from the group consisting of oxygen atom, a nitrogen atom, and a sulfur atom, an unsubstituted or substituted heterocyclic ring, an unsubstituted or substituted alkoxy group, and an unsubstituted or substituted $C_3$ to $C_6$ cycloalkyl group; a cyclopentyl group; a benzylpiperidyl group; a tetrahydrofuryl group; a dibenzocycloheptyl group or an indanyl group may be mentioned. More preferably, methyl; butyl; 2-methylpropyl; 2-ethylbutyl; a $C_1$ to $C_5$ alkyl group substituted with phenyl, pyridyl, naphthyl, methylthiazolyl, fluorophenyl, benzylpiperazinyl, benzylpiperidyl, benzyloxy, cyclopropylmethoxy, or a $C_3$ to $C_6$ cycloalkyl group, which may have a phenyl group; a cyclopentyl group; a cyclopropylmethyl group; a benzylpiperidyl group; a tetrahydrofuryl group; a dibenzocycloheptyl group or a 2-indanyl group may be mentioned.

As the $C_1$ to $C_4$ linear or branched alkyl group of $R_2$, methyl, ethyl, n-propyl, isopropyl, n-butyl, sec-butyl, t-butyl, etc. may be mentioned. Preferably methyl or ethyl may be mentioned. More preferably, methyl may be mentioned.

As $R_3$, a hydrogen atom may be mentioned. Further, as the $C_1$ to $C_5$ linear or branched alkyl group of $R_3$, methyl, ethyl, n-propyl, isopropyl, n-butyl, sec-butyl, t-butyl, n-pentyl, etc. may be mentioned. The $C_1$ to $C_5$ linear or branched alkyl group may be substituted with an aryl group (e.g. phenyl, tolyl, naphtyl, etc.) which may be substituted with a halogen atom, an unsubstituted or substituted heteroaryl groups, which contains at least one hetero atom selected from the group consisting of an oxygen atom, a nitrogen atom, and a sulfur atom (e.g. pyridyl, thiazolyl, furyl, thienyl, quinolyl, etc.), or with an alkoxycarbonyl group. As the substituted $C_1$ to $C_5$ alkyl group, for example, ethoxycarbonylmethyl, benzyl, 4-bromobenzyl, phenethyl, 3-phenylpropyl, pyridylmethyl, 4-phenylbutyl, 5-phenylpentyl, furylmethyl, thiazolylmethyl, 2-quinolylmethyl, 1-naphthylmethyl, etc. may mentioned.

As the $C_3$ to $C_7$ cycloalkyl group of $R_3$, cyclopropyl, cyclobutyl, cyclopentyl, cyclohexyl, cycloheptyl, etc. may be mentioned.

As the aryl group of $R_3$, phenyl, tolyl, napthyl, etc. may be mentioned.

As the heteroaryl group which contains at least one hetero atom selected from the group consisting of oxygen, nitrogen and sulfur of $R_3$, pyridyl, thiazolyl, furyl, thienyl, etc. may be mentioned.

As the acyl group of $R_3$, formyl, acetyl, propionyl, benzoyl, 2-naphthoyl, 3-furoyl, 2-thenoyl, nicotinoyl, isonicotinoyl, etc. may be mentioned.

As $R_3$, preferably a hydrogen; a $C_1$ to $C_4$ alkyl group; an aryl group; an unsubstituted or substituted heteroaryl group which may be substituted with halogen and may contain at least one hetero atom selected from the group consisting of oxygen, nitrogen, and sulfur, a $C_1$ to $C_3$ alkyl group substituted with a $C_4$ to $C_6$ cycloalkyl group containing at least one hetero atom selected from the group consisting of oxygen, nitrogen, and sulfur; ethoxycarbonylmethyl; or benzoyl may be mentioned. More preferably, hydrogen, methyl, ethyl, benzyl, 2-pyridylmethyl, or 4-pyridylmethyl may be mentioned.

As $R_4$, a hydrogen atom may be mentioned. As the $C_1$ to $C_6$ linear or branched alkyl group, methyl, ethyl, propyl, isopropyl, butyl, sec-butyl, t-butyl, pentyl, hexyl, etc. may be mentioned. These may be substituted with any substituent group. As the aryl group of $R_4$, phenyl, tolyl, napthyl, 4-methylphenyl, 4-chlorophenyl, etc. may be mentioned.

As the heteroaryl group which contains at least one hetero atom selected from the group consisting of oxygen, nitrogen and sulfur of $R_4$, pyridyl, thiazolyl, furyl, thienyl, etc. may be mentioned. These may be substituted with any substituent group.

As $R_4$, preferably hydrogen, methyl, ethyl, phenyl, or pyridyl may be mentioned. More preferably hydrogen or methyl may be mentioned.

$R_5$ and $R_6$ may independently be hydrogen. Further, $R_5$ and $R_6$ may independently be a $C_1$ to $C_6$ linear or branched alkyl group such as methyl, ethyl, propyl, isopropyl, butyl, sec-butyl, t-butyl, pentyl, hexyl, etc. These $C_1$ to $C_6$ linear or branched alkyl groups may be substituted with a halogen atom; a hydroxy group; a cyano group; an amino group; a carboxyl group; a cycloalkyl group; a haloalkyl group; a carbamoyl group; an alkoxy group; an alkylcarbonyl group; or an aryl group or an unsubstituted or substituted heteroaryl group, which may contain at least one hetero atom selected from the group consisting of oxygen, nitrogen, and sulfur.

$R_5$ and $R_6$ may independently be an aryl group such as phenyl, tolyl, napthyl, 4-methylphenyl, 4-chlorophenyl, etc.; or a heteroaryl group which contains at least one hetero atom selected from the group consisting of oxygen, nitrogen and sulfur, such as pyridyl, thiazolyl, furyl, thienyl, etc. may be mentioned. These groups may be substituted with a halogen atom, a hydroxy group, a cyano group, an amino group, a carboxyl group, an alkyl group, a cycloalkyl group, a haloalkyl group, a carbamoyl group, an alkoxy group, or an alkylcarbonyl group.

As $R_5$ and $R_6$, preferably hydrogen, methyl, or phenyl, may be mentioned. More preferably, hydrogen or methyl may be mentioned.

Specific compounds having the above formula (I) are those produced by the Examples mentioned below.

The compounds having the above formula (I) have asymmetric carbon atoms and include optical isomers. The optical isomers are also within the scope of the present invention. Further, the salts of the compounds having the above formula (I) and their optical isomers are also within the scope of the present invention. As their salts, pharmacologically acceptable salts are preferable. As the pharmacologically acceptable salts, for example, inorganic acid salts such as hydrochlorides, hydrobromides hydroiodides, and phosphates, etc. and organic acid salts such as oxalates, maleates, fumarates, lactates, malates, citrates, tartarates, benzoates, methanesulfonates, and p-toluenesulfonates, etc. may be mentioned.

Further, the present invention includes hydrates and solvates of the compounds having the above formula (I), their optical isomers, and their salts. As the solvent of the solvates, methanol, ethanol, isopropanol, butanol, acetone, ethyl acetate, chloroform, etc. may be mentioned.

The compounds having the above formula (I) may be produced by the following method combining known reactions. An example of the production process will be explained by the following reaction schemes.

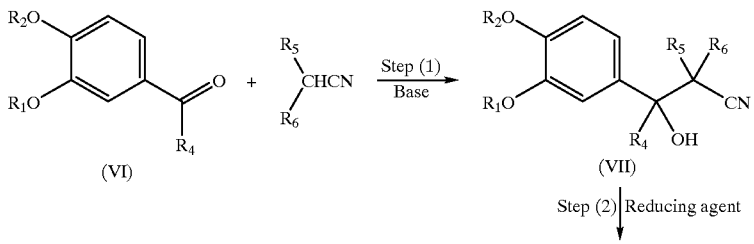

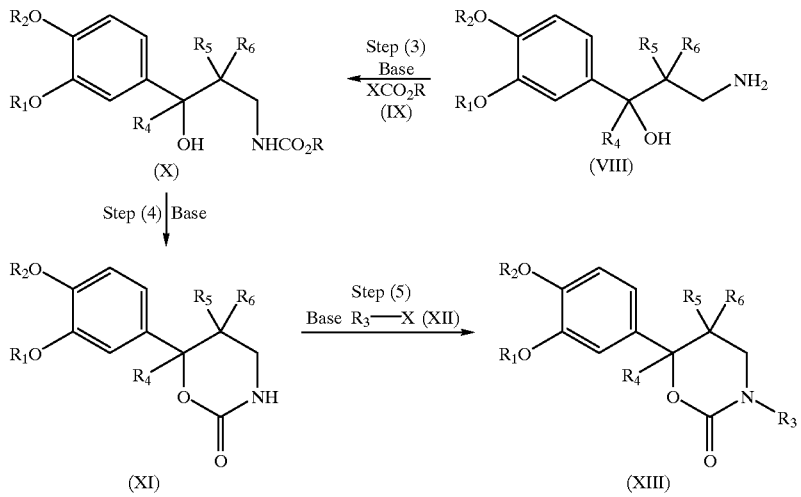

The compounds (XI) and (XIII) in the above reaction scheme correspond to compounds having the above formula (I).

Step (1): A ketone derivative (or an aldehyde derivative when $R_4$ represented a hydrogen atom) (VI) was reacted with a nitrile ($R_5R_6$CHCN) in the presence of a base such as lithium diisopropylamide (LDA) to synthesize a nitrile derivative (VII). In general, as the reaction solvent, an ether solvent such as diethyl ether or tetrahydrofuran is used and the reaction temperature is 0° C. or less.

Step (2): The nitrile derivative (VII) is converted to an aminoalcohol derivative (VIII) by a reducing agent such as lithium aluminum hydride.

Step (3): The aminoalcohol derivative (VIII) is reacted with a halogenated formic acid ester having the formula (IX), wherein X is a halogen atom and R is an alkyl group in the presence of a base such as triethylamine or pyridine to synthesize the compound (X).

Step (4): The compound (X) is intramolecularly condensed with a base such as sodium hydride or sodium methoxide to obtain a ring-closed compound (XI).

Step (5): The compound (XI) is reacted with an alkyl halide (XII), wherein X is a halogen atom, in the presence of a base such as sodium hydride to obtain the compound (XIII).

The compounds obtained in the above steps are isolated by known methods (e.g., crystallization, recrystallization, chromatography, etc.), but sometimes the synthesis intermediates are used for the next steps without further purification.

The starting materials, which may be used in the above reaction process, are commercially available products or may be synthesized from known compounds. For example, the ketone derivative (U/C) may be produced by a known method (for example, see WO94/10118).

When the compound of the present invention is used as a therapeutic agent, it can be administered alone or together with a pharmacologically acceptable carrier. The composition is determined by the solubility of the compound, its chemical properties, the delivery route, medication plan, etc.

For instance, it can be orally administered in the form of granules, powders, tablets, pills, hard gelatin capsules, soft gelatin capsules, syrups, emulsions, suspensions, liquids, etc. or can be administered by a non-oral route such as an injection (intravenous, intramuscular, or hypodermic), ointment, suppository, aerosol, etc. Alternatively, it may be made a powder for injection which is prepared at the time of use. Organic or inorganic solid or liquid carriers or diluents which are suitable for oral, rectal, non-oral, and topical administration can be used together with the compound of the invention. For example, in the case of oral administration, the compound can be prepared in the desired form by using excipients such as lactose, D-glucose, corn starch, and sucrose, disintegrants such as calcium carboxymethylcellulose, hydroxypropylcellulose, etc., lubricants such as calcium stearate, magnesium stearate, talc, polyethylene glycol, and hydrogenated oil, humectants such as hydroxypropylcellulose, hydroxypropylmethylcellulose, carboxymethylcellulose, polyvinyl alcohol, gelatin, and gum arabic, and a surfactant and flavoring agents if necessary.

When administered by a non-oral route, it is possible to use a diluent such as water, ethanol, glycerine, propylene glycol, polyethylene glycol, agar, and tragacanth and, if necessary, use a solution adjuvant, buffering agent, preservative, flavoring agent, and colorant, etc. Pharmaceutical compositions may be prepared by general methods.

The clinical dosage generally ranges 0.01 to 1000 mg in terms of the compound of the invention per adult per day when orally administered, preferably 0.01 to 100 mg, but can be appropriately arranged depending upon the age, condition, symptoms, other drugs administered at the same time, etc. The daily dosage of the drug (compound of present invention) can be administered once a day or twice or three times a day with suitable intervals or intermittently. When administered by injection, one dosage in an amount of 0.001 to 100 mg per adult with or without intervals is preferable.

EXAMPLES

The present example will be explained in detail below by Examples and Test Examples, but of course the present invention is not limited to these Examples and Test Examples.

Example 1

Synthesis of 6-(3,4-dimethoxyphenyl)-3,4,5,6-tetrahydro-2H-1,3-oxazin-2-one (Compound No. 1 of Table 1)

(1) Synthesis of 3-(3,4-dimethoxyphenyl)-3-hydroxypropiononitrile

A solution of diisopropylamine (0.67 g, 6.62 mM) in dried tetrahydrofuran (5 ml) was cooled to −78° C. A hexane solution of n-butyllithium (6.62 mM) was dropped into this solution, then this was stirred at that temperature for 30 minutes. Next, acetonitrile (0.27 g, 6.62 mM) was dropped into this solution and the result stirred for a further 30 minutes, then a solution of 3,4-dimethoxybenzaldehyde (1.00 g, 6.02 mM) in dried tetrahydrofuran (5 ml) was added and the mixture stirred at that temperature for 4 hours. An aqueous ammonium chloride was poured into the obtained solution, which was warmed to room temperature and extracted with diethyl ether. The organic layer was dried over anhydrous magnesium sulfate, then the solvent was removed in vacuo to obtain a crude product (1.25 g) of 3-(3,4-dimethoxyphenyl)-3-hydroxypropiononitrile as a yellow oil. The crude product thus obtained had sufficient purity without purification, therefore could be used for the next reaction as it was.

$^1$H-NMR (400 MHz, CDCl$_3$) δ2.74 (1H, dd, J=16.60, 5.86 Hz), 2.79 (1H, dd, J=16.60, 5.86 Hz), 3.89 (3H, s), 3.91 (3H, s), 5.00 (1H, t, J=5.86 Hz), 6.87 (1H, d, J=8.30 Hz), 6.93 (1H, dd, J=8.30, 1.95 Hz), 6.96 (1H, d, J=1.95 Hz)

(2) Synthesis of 3-amino-1-(3,4-dimethoxyphenyl)-1-propanol

A solution of 3-(3,4-dimethoxyphenyl)-3-hydroxypropiononitrile (1.25 g, 6.02 mM) in dried tetrahydrofuran (25 ml) was dropped into a solution of lithium aluminum hydride (0.55 g, 14.48 mM) in dried tetrahydrofuran (40 ml) at 0° C. This was gradually warmed to room temperature and stirred for 1 hour. Next, the reaction solution was again cooled to 0° C., water was carefully added to it, then the mixture was stirred at room temperature for 30 minutes. Next, the solution was filtered through Celite, the filtrate was dried over anhydrous sodium sulfate, then the solvent was removed in vacuo to obtain a crude product of 3-amino-1-(3,4-dimethoxyphenyl)-1-propanol (1.27 g). The crude product obtained here had a sufficient purity even without purification, so could be used as it was for the next reaction.

$^1$H-NMR (400 MHz, CDCl$_3$) δ1.72–1.87 (2H, m), 2.95 (1H, ddd, J=12.70, 9.28, 3.91 Hz), 3.11 (1H, ddd, J=12.70, 5.37, 5.37 Hz), 3.87 (3H, s), 3.90 (3H, s), 4.90 (1H, dd, J=7.30, 2.93 Hz), 6.83 (1H, d, J=8.30 Hz), 6.88 (1H, dd, J=8.30, 1.96 Hz), 6.97 (1H, d, J=1.96 Hz)

(3) Synthesis of 6-(3,4-dimethoxyphenyl)-3,4,5,6-tetrahydro-2H-1,3-oxazin-2-one 3-amino-1-(3,4-dimethoxyphenyl)-1-propanol (1.27 g, 6.02 mM), triethylamine (0.84 g, 8.30 mM), and methyl chloroformate (0.59 g, 6.25 mM) were dissolved in dried tetrahydrofuran (80 ml) and stirred at room temperature for 5.5 hours. The solution obtained was poured into ice water and extracted with methylene chloride. The organic layer was dried over anhydrous sodium sulfate, then the solvent was removed in vacuo to obtain a crude product of 1-(3,4-dimethoxyphenyl)-3-(methoxycarbonylamino)-1-propanol as a yellow oil. Next, the crude product was dissolved in dried benzene (5 ml). The mixture was dropped into a solution of sodium hydride (60%) (0.24 g, 6.04 mM) in dried benzene (40 ml) at room temperature, water was added into the reaction solution and the mixture stirred at that temperature for 24 hours, which was then extracted with methylene chloride. The extract was dried over anhydrous sodium sulfate, then the solvent was removed in vacuo to obtain a crude product as a brown solid. The crude product was washed with ether to obtain the above-described compound 0.86 g (yield 63.1%) as a light brown solid.

$^1$H-NMR (400 MHz, CDCl$_3$) δ2.07–2.18 (1H, m), 2.19–2.23 (1H, m), 3.38–3.44 (1H, m), 3.50 (1H, ddd, J=10.74, 10.74, 4.88 Hz), 3.89 (3H, s), 3.90 (3H, s), 5.27 (1H, m), 6.86 (1H, d, J=8.30 Hz), 6.90 (1H, dd, J=8.30, 1.46 Hz), 6.92 (1H, d, J=1.46 Hz)

Example 2

Synthesis of 6-(3-cyclopentyloxy-4-methoxyphenyl)-3,4,5,6-tetrahydro-2H-1,3-oxazin-2-one (Compound No. 2 of Table 1)

(1) Synthesis of 3-(3-cyclopentyloxy-4-methoxyphenyl)-3-hydroxypropiononitrile

According to the same procedure as in Example 1(1), using 3-cyclopentyloxy-4-methoxybenzaldehyde instead of 3,4-dimethoxybenzaldehyde, 3-(3-cyclopentyloxy-4-methoxyphenyl)-3-hydroxypropiononitrile was obtained as a light yellow oil.

$^1$H-NMR (400 MHz, CDCl$_3$) δ1.58–1.67 (2H, m), 1.79–1.98 (6H, m), 2.74–2.76 (2H, m), 3.84 (3H, s), 4.80 (1H, m), 4.97 (1H, t, J=5.86 Hz), 6.85 (1H, d, J=8.30 Hz), 6.90 (1H, dd, J=8.30, 1.95 Hz), 6.95 (1H, d, J=1.95 Hz)

(2) Synthesis of 6-(3-cyclopentyloxy-4-methoxyphenyl)-3,4,5,6-tetrahydro-2H-1,3-oxazin-2-one According to the same procedure as in Example 1(2) to (3), using 3-(3-cyclopentyloxy-4-methoxyphenyl)-3-hydroxypropiononitrile instead of 3-(3,4-dimethoxyphenyl)-3-hydroxypropiononitrile, the above-described compound (yield 60.5%) was obtained as a light yellow solid.

$^1$H-NMR (400 MHz, CDCl$_3$) δ1.57–1.66 (2H, m), 1.79–1.97 (6H, m), 2.03–2.21 (2H, m), 3.36–3.42 (1H, m), 3.47 (1H, ddd, J=10.75, 10.75, 4.88 Hz), 3.85 (3H, s), 4.80 (1H, m), 5.26 (1H, dd, J=9.77, 2.45 Hz), 5.81 (1H, broad s), 6.85 (1H, d, J=8.30 Hz), 6.87–6.90 (2H, m)

Example 3

Synthesis of 6-(3-butoxy-4-methoxyphenyl)-3,4,5,6-tetrahydro-2H-13-oxazin-2-one (Compound No. 3 of Table 1)

(1) Synthesis of 3-butoxy-4-methoxybenzaldehyde

Isovanillin (6.00 g, 39.4 mM), butyl iodide (5.7 ml, 49.3 mM), and anhydrous potassium carbonate (6.8 g, 49.3 mM) were dissolved in dried dimethylformamide (50 ml) and stirred at room temperature for one night, then the solution was diluted with ethyl acetate (300 ml) and washed with water. The organic layer was dried over anhydrous magnesium sulfate and the solvent was removed in vacuo to obtain a residue as a light yellow oil. The residue was purified by flash chromatography (SiO$_2$: eluted by 20% ethyl acetate/hexane solution). The solvent was removed in vacuo and the resultant product was dried to obtain 3-butoxy-4-methoxy-3-benzaldehyde 8.09 g (yield 99.0%) as a light yellow oil.

$^1$H-NMR (400 MHz, CDCl$_3$) δ0.99 (3H, t, J=7.32 Hz), 1.46–1.55 (2H, m), 1.82–1.89 (2H, m), 3.95 (3H, s), 4.08 (2H, t, J=6.83 Hz), 6.98 (1H, d, J=7.81 Hz), 7.40–7.46 (2H, m), 9.84 (1H, s)

(2) Synthesis of 3-(3-butoxy-4-methoxyphenyl)-3-hydroxypropiononitrile

According to the same procedure as in Example 1(1), using 3-butoxy-4-methoxybenzaldehyde instead of 3,4- dimethoxybenzaldehyde, 3-(3-butoxy-4-methoxyphenyl)-3-hydroxypropiononitrile was obtained as a light yellow oil.

$^1$H-NMR (400 MHz, CDCl$_3$) δ0.98 (3H, t, J=7.32 Hz), 1.49 (2H, m, J=7.32 Hz), 1.83 (2H, m), 2.72 (1H, dd, J=16.60, 6.35 Hz), 2.77 (1H, dd, J=16.60, 6.35 Hz), 3.86 (3H, s), 4.02 (2H, t, J=6.84 Hz), 4.97 (1H, t, J=6.35 Hz), 6.85 (1H, d, J=8.30 Hz), 6.90 (1H, dd, J=8.30, 1.95 Hz), 6.94 (1H, d, J=1.95 Hz)

(3) Synthesis of 6-(3-butoxy-4-methoxyphenyl)-3,4,5,6tetrahydro-2H-1,3-oxazin-2-one According to the same procedure as in Example 1(2) to (3), using 3-(3-butoxy-4-methoxyphenyl)-3-hydroxypropiononitrile instead of 3-(3,4-dimethoxyphenyl)-3-hydroxypropiononitrile, the above-described compound (yield 61.1%) was obtained as a light brown solid.

$^1$H-NMR (400 MHz, CDCl$_3$) δ0.98 (3H, t, J=7.33 Hz), 1.50 (2H, m, J=7.33 Hz), 1.83 (2H, q, J=7.33 Hz), 2.07–2.22 (2H, m), 3.38–3.51 (2H, m), 3.87 (3H, s), 4.03 (2H, t, J=7.33 Hz), 5.27 (1H, dd, J=9.76, 1.95 Hz), 5.47 (1H, broad s), 6.84–6.92 (3H, m)

Example 4

Synthesis of 6-(3-cyclopropylmethyloxy-4-methoxyphenyl)-3,4,5 6-tetrahydro-2H-1 3-oxazin-2-one (Compound No. 4 of Table 1)

(1) Synthesis of 3-cyclopropylmethyloxy-4-methoxybenzaldehyde

Isovanillin (2.00 g, 13.14 mM), cyclopropylcarbinol (0.95 g, 13.14 mM), and triphenylphosphine (4.14 g, 15.77 mM) were dissolved in dried tetrahydrofuran (50 ml). Diethyl azodicarboxylate (2.75 g, 15.77 mM) was carefully dropped into this solution at room temperature. The solution was stirred at room temperature for one night, then this solution was diluted with diethyl ether (100 ml) and was successively washed with a aqueous sodium hydroxide and water. The organic solution was dried over anhydrous magnesium sulfate and the solvent was removed in vacuo to obtain a residue as a light yellow oil. The residue was purified by flash chromatography (SiO$_2$: eluted by 25% hexane/ethyl acetate). The solvent was removed in vacuo and the resultant product was dried to obtain 3-cyclopropylmethyloxy-4-methoxybenzaldehyde 2.10 g (yield 77.4%) as a white solid.

$^1$H-NMR (400 MHz, CDCl$_3$) δ0.36–0.40 (2H, m), 0.65–0.70 (2H, m), 1.34–1.38 (1H, m), 3.92 (2H, d, J=6.84 Hz), 3.97 (3H, s), 6.98 (1H, d, J=8.30 Hz), 7.39 (1H, d, J=1.95 Hz), 7.45 (1H, dd, J=8.30, 1.95 Hz), 9.84 (1H, s)

(2) Synthesis of 3-(3-cyclopropylmethyloxy-4-methoxyphenyl)-3-hydroxypropiononitrile According to the same procedure as in Example 1(1), using 3-cyclopropylmethyloxy-4-methoxybenzaldehyde instead of 3,4-dimethoxybenzaldehyde, 3-(3-cyclopropylmethyloxy-4-methoxyphenyl)-3-hydroxypropiononitrile was obtained as a light yellow oil.

$^1$H-NMR (400 MHz, CDCl$_3$) δ0.34–0.38 (2H, m), 0.63–0.68 (2H, m), 1.28–1.38 (1H, m), 2.73 (1H, dd, J=16.60, 6.35 Hz), 2.77 (1H, dd, J=16.60, 6.35 Hz), 3.86 (2H, d, J=7.81 Hz), 3.88 (3H, s), 4.97 (1H, t, J=6.35 Hz), 6.87 (1H, d, J=8.30 Hz), 6.92 (1H, dd, J=8.30, 1.95 Hz), 6.94 (1H, d, J=1.95 Hz)

(3) Synthesis of 6-(3-cyclopropylmethyloxy-4-methoxyphenyl)-3,4 5,6-tetrahydro-2H-1,3-oxazin-2-one According to the same procedure as in Example 1(2) to (3), using 3-(3-cyclopropylmethyloxy-4-methoxyphenyl)-3-hydroxypropiononitrile instead of 3-(3,4-dimethoxyphenyl)-3-hydroxypropiononitrile, the above-described compound (yield 60.5%) was obtained as a light brown solid.

$^1$H-NMR (400 MHz, CDCl$_3$) δ0.34–0.38 (2H, m), 0.62–0.67 (2H, m), 1.29–1.39 (1H, m), 2.03–2.20 (2H, m), 3.37–3.43 (1H, m), 3.48 (1H, ddd, J=11.23, 11.23, 4.88 Hz), 3.86 (2H, d, J=7.32 Hz), 3.88 (3H, s), 5.26 (1H, dd, J=10.25, 2.93 Hz), 5.54 (1H, broad s), 6.85–6.91 (3H, m)

Example 5

Synthesis of 6-(3,4-dimethoxyphenyl)-6-methyl-3,4,5,6-tetrahydro-2H-1,3-oxazin-2-one (Compound No. 5 of Table 1)

(1) Synthesis of 3-(3,4-dimethoxyphenyl)-3-hydroxybutyronitrile

According to the same procedure as in Example 1(1), using 3,4-dimethoxyacetophenone instead of 3,4-dimethoxybenzaldehyde, 3-(3,4-dimethoxyphenyl)-3-hydroxybutyronitrile was obtained as a light yellow oil.

$^1$H-NMR (400 MHz, CDCl$_3$) δ1.77 (3H, s), 2.78 (1H, d, J=16.60 Hz), 2.84 (1H, d, J=16.60 Hz), 3.89 (3H, s), 3.91 (3H, s), 6.86 (1H, d, J=8.30 Hz), 6.97 (1H, dd, J=8.30, 1.95 Hz), 7.08 (1H, d, J=1.95 Hz)

(2) Synthesis of 6-(3.4-dimethoxyphenyl)-6-methyl-3,4,5,6-tetrahydro-2H-1,3-oxazin-2-one According to the same procedure as in Example 1(2) to (3), using 3-(3,4-dimethoxyphenyl)-3-hydroxybutyronitrile instead of 3-(3,4-dimethoxyphenyl)-3-hydroxypropiononitrile, the above-described compound (yield 44.4%) was obtained as a light brown oil.

$^1$H-NMR (400 MHz, CDCl$_3$) δ1.67 (3H, s), 2.10–2.17 (1H, m), 2.31 (1H, ddd, J=14.16, 4.39, 4.39 Hz), 3.03–3.09 (1H, m), 3.25–3.31 (1H, m), 3.88 (3H, s), 3.89 (3H, s), 5.81 (1H, broad s), 6.86–6.92 (3H, m)

Example 6

Synthesis of 6-(3-cyclopentyloxy-4-methoxyphenyl)-6-methyl-3,4,5 6-tetrahydro-2H-1,3-oxazin-2-one (Compound No. 6 of Table 1)

(1) Synthesis of 3-cyclopentyloxy-4-methoxyacetophenone

A solution of 3-cyclopentyloxy-4-methoxybenzaldehyde (10.00 g, 45.40 mM) in dried tetrahydrofuran (100 ml) was cooled to 0° C., a tetrahydrofuran solution of methyl magnesium bromide (136.20 mM) was dropped into this solution, and the resultant mixture was stirred at that temperature for 2 hours. A aqueous ammonium chloride was added to the solution obtained, which was then warmed to room temperature and extracted with ethyl acetate. The extract was successively washed with brine and water. The organic solution was dried over anhydrous magnesium sulfate and the solvent was removed in vacuo to obtain crude product of 1-(3-cyclopentyloxy-4-methoxyphenyl)ethanol 10.67 g as a light yellow oil. The crude product thus obtained of 1-(3-cyclopentyloxy-4-methoxyphenyl)ethanol (10.67 g) was dissolved in dried methylene chloride (200 ml). Manganese dioxide (39.2 g) was added to this solution. The resultant product was stirred vigorously at room temperature for 16 hours. The undissolved material in the solution was removed by filtration through Celite, then the filtrate was concentrated in vacuo to obtain residue as a yellow oil. The residue was purified by flash chromatography (SiO$_2$: eluted by 25% ethyl acetate/hexane). The solvent was removed in vacuo and the resultant product was dried to obtain 3-cyclopentyloxy-4-methoxyacetophenone 10.00 g (yield 94.4%) as a yellow oil.

$^1$H-NMR (400 MHz, CDCl$_3$) δ1.61–1.64 (2H, m), 1.81–1.90 (4H, m), 1.97–2.00 (2H, m), 2.56 (3H, s), 3.91 (3H, s), 4.86 (1H, m), 6.87 (1H, d, J=8.30 Hz), 7.52 (1H, d, J=1.95 Hz), 7.55 (1H, dd, J=8.30, 1.95 Hz)

(2) Synthesis of 3-(3-cyclopentyloxy-4-methoxyphenyl)-3-hydroxybutyronitrile

According to the same procedure as in Example 1(1), using 3-cyclopentyloxy-4-methoxyacetophenone instead of 3,4-dimethoxybenzaldehyde, 3-(3-cyclopentyloxy-4-methoxyphenyl)-3-hydroxybutyronitrile was obtained as a light yellow oil.

$^1$H-NMR (400 MHz, CDCl$_3$) δ1.59–1.62 (2H, m), 1.72 (3H, s), 1.80–1.94 (6H, m), 2.74 (1H, d, J=16.60 Hz), 2.80 (1H, d, J=16.60 Hz), 3.82 (3H, s), 4.79 (1H, m), 6.83 (1H, d, J=8.30 Hz), 6.94 (1H, dd, J=8.30, 1.95 Hz), 7.05 (1H, d, J=1.95 Hz)

(3) Synthesis of 6-(3-cyclopentyloxy-4-methoxyphenyl)-6-methyl-3,4,5,6-tetrahydro-2H-1,3-oxazin-2-one According to the same procedure as in Example 1(2) to (3), using 3-(3-cyclopentyloxy-4-methoxyphenyl)-3-hydroxybutyronitrile instead of 3-(3,4-dimethoxyphenyl)-3-hydroxypropiononitrile, the above-described compound (yield 51.9%) was obtained as a light yellow oil.

$^1$H-NMR (400 MHz, CDCl$_3$) δ1.56–1.69 (2H, m), 1.65 (3H, s), 1.78–1.97 (6H, m), 2.11 (1H, ddd, J=13.67, 10.74, 5.37 Hz), 2.28 (1H, ddd, J=13.67, 3.90, 3.90 Hz), 3.03 (1H, ddd, J=11.23, 10.74, 3.90 Hz), 3.22–3.27 (1H, m), 3.84 (3H, s), 4.80 (1H, m), 5.80 (1H, broad s), 6.84 (2H, s), 6.90 (1H, s)

Example 7

Synthesis of 6-(3-cyclopentyloxy-4-methoxyphenyl)-6-phenyl-3,4,5,6-tetrahydro-2H-1,3-oxazin-2-one (Compound No. 7 of Table 1)

(1) Synthesis of 3-cyclopentyloxy-4-methoxybenzophenone

A solution of 3-cyclopentyloxy-4-methoxybenzaldehyde (10.00 g, 45.40 mM) in dried tetrahydrofuran (50 ml) was cooled to −78° C. A toluene solution of phenyllithium (49.94 mM) was dropped into this solution and the resultant mixture was stirred at that temperature for 5 hours. Water was added to the solution obtained, which was then warmed to room temperature and extracted with diethyl ether. The extract was dried over anhydrous magnesium sulfate, then the solvent was removed in vacuo to obtain a crude product of α-(3-cyclopentyloxy-4-methoxyphenyl)benzylalcohol (13.56 g) as a yellow oil. The crude product (10.00 g) of α-(3-cyclopentyloxy-4-methoxyphenyl)benzylalcohol was dissolved in dried methylene chloride (110 ml) thus obtained, manganese dioxide (16.00 g) was added to the solution, then the solution was vigorously stirred at room temperature for 2 days. The undissolved material in the solution was removed by filtration through Celite and the filtrate was concentrated in vacuo to obtain a residue as a yellow solid. The residue was purified by flash chromatography (SiO$_2$: eluted by 20% ethyl acetate/hexane). The solvent was removed in vacuo and the resultant product was dried to obtain 3-cyclopentyloxy-4-methoxybenzophenone 9.20 g (yield 92.6%) as a light yellow solid.

$^1$H-NMR (400 MHz, CDCl$_3$) δ1.60–1.65 (2H, m), 1.82–2.00 (6H, m), 3.93 (3H, s), 4.84 (1H, m), 6.89 (1H, d, J=8.30 Hz), 7.38 (1H, dd, J=8.30, 1.95 Hz), 7.46 (1H, d, J=1.95 Hz), 7.49 (2H, d, J=7.81 Hz), 7.55–7.59 (1H, m), 7.75–7.77 (2H, m)

(2) Synthesis of 3-(3-cyclopentyloxy-4-methoxyphenyl)-3-hydroxy-3-phenylpropiononitrile According to the same procedure as in Example 1(1), using 3-cyclopentyloxy-4-methoxybenzophenone instead of 3,4-dimethoxybenzaldehyde, 3-(3-cyclopentyloxy-4-methoxyphenyl)-3-hydroxy-3-phenylpropiononitrile was obtained as a light yellow oil.

$^1$H-NMR (400 MHz, CDCl$_3$) δ1.54–1.62 (2H, m), 1.75–1.91 (6H, m), 2.80 (1H, broad s), 3.22 (1H, d, J=16.60 Hz), 3.26 (1H, d, J=16.60 Hz), 3.83 (3H, s), 4.69 (1H, m), 6.82 (1H, d, J=8.30 Hz), 6.88 (1H, dd, J=8.30, 2.44 Hz), 6.91 (1H, d, J=2.44 Hz), 7.29–7.41 (5H, m)

(3) Synthesis of 6-(3-cyclopentyloxy-4-methoxyphenyl)-6-phenyl-3,4,5,6-tetrahydro-2H-1,3-oxazin-2-one According to the same procedure as in Example 1(2) to (3), using 3-(3-cyclopentyloxy-4-methoxyphenyl)-3-hydroxy-3-phenylpropiononitrile instead of 3-(3,4-dimethoxyphenyl)-3-hydroxypropiononitrile, the above-described compound (yield 48.6%) was obtained as a yellow solid.

$^1$H-NMR (400 MHz, CDCl$_3$) δ1.56–1.59 (2H, m), 1.79–1.88 (6H, m), 2.61–2.65 (2H, m), 3.23–3.29 (2H, m), 3.82 (3H, s), 4.73 (1H, m), 5.37 (1H, broad s), 6.82 (1H, d, J=8.30 Hz), 6.91 (1H, dd, J=8.30, 2.44 Hz), 6.94 (1H, d, J=2.44 Hz), 7.28 (1H, d, J=7.33 Hz), 7.35 (2H, t, J=7.33 Hz), 7.41 (2H, d, J=7.33 Hz)

Example 8

Synthesis of 6-(3,4-dimethoxyphenyl)-3-methyl-3,4,5,6-tetrahydro-2H-1,3-oxazin-2-one (Compound No. 8 of Table 1)

To a solution of the 6-(3,4-dimethoxyphenyl)-3,4,5,6-tetrahydro-2H-1,3-oxazin-2-one (1.20 g, 5.06 mM) produced in Example 1 in dried N,N-dimethylformamide (30 ml) were added sodium hydride (60%) (0.41 g, 10.12 mM) and methyl iodide (1.44 g, 10.12 mM). The solution was then stirred at room temperature for one night. The reaction solution was carefully poured into ice water, then extracted with methylene chloride. The extract was dried over anhydrous sodium sulfate and the solvent was removed in vacuo to obtain a residue as a brown oil. The residue was purified by flash chromatography (SiO$_2$; eluted by 0.5% methanol/chloroform) to obtain the above-described compound 0.28 g (yield 22.3%) as a colorless solid.

$^1$H-NMR (400 MHz, CDCl$_3$) δ2.16–2.22 (2H, m), 3.05 (3H, s), 3.25–3.30 (1H, m), 3.49 (1H, ddd, J=11.72, 11.72, 5.86 Hz), 3.89 (3H, s), 3.90 (3H, s), 5.23 (1H, dd, J=9.77, 3.42 Hz), 6.84–6.92 (3H, m)

Example 9

Synthesis of 3-benzyl-6-(3 4-dimethoxyphenyl)-3,4,5,6-tetrahydro-2H-1,3-oxazin-2-one (Compound No. 9 of Table 1)

According to the same procedure as in Example 8, using benzyl bromide instead of methyl iodide, the above-described compound (yield 74.1%) was obtained as a light yellow solid.

$^1$H-NMR (400 MHz, CDCl$_3$) δ2.10–2.22 (2H, m), 3.21 (1H, ddd, J=11.72, 5.86, 3.42 Hz), 3.32–3.39 (1H, m), 3.88 (3H, s), 3.89 (3H, s), 4.57 (1H, d, J=15.13 Hz), 4.68 (1H, d, J=15.13 Hz), 5.25 (1H, dd, J=9.77, 2.93 Hz), 6.84 (1H, d, J=8.30 Hz), 6.88 (1H, dd, J=8.30, 1.95 Hz), 6.92 (1H, d, J=1.95 Hz), 7.28–7.38 (5H, m)

Example 10

Synthesis of 6-(3-cyclopentyloxy-4-methoxyphenyl)-3-methyl-3,4,5,6-tetrahydro-2H-1 3-oxazin-2-one (Compound No. 10 of Table 1)

According to the same procedure as in Example 8, using the 6-(3-cyclopentyloxy-4-methoxyphenyl)-3,4,5,6-tetrahydro-2H-1,3-oxazin-2-one produced in Example 2 instead of 6-(3,4-dimethoxyphenyl)-3,4,5,6-tetrahydro-2H-1,3-oxazin-2-one, the above-described compound (yield 77.6%) was obtained as a yellow solid.

$^1$H-NMR (400 MHz, CDCl$_3$) δ1.57–1.65 (2H, m), 1.79–1.96 (6H, m), 2.13–2.24 (2H, m), 3.03 (3H, s), 3.25 (1H, ddd, J=11.72, 5.86, 3.42 Hz), 3.47 (1H, ddd, J=11.72, 10.25, 5.86 Hz), 3.84 (3H, s), 4.79 (1H, m), 5.21 (1H, dd, J=9.77, 3.42 Hz), 6.83–6.90 (3H, m)

Example 11

Synthesis of 3-(4-bromobenzyl)-6-(3-cyclopentyloxy-4-methoxyphenyl)-3,4,5,6-tetrahydro-2H-1,3-oxazin-2-one (Compound No. 11 of Table 1)

According to the same procedure as in Example 10, using 4-bromobenzyl bromide instead of methyl iodide, the above-described compound (yield 99.5%) was obtained as a yellow oil.

$^1$H-NMR (400 MHz, CDCl$_3$) δ1.56–1.66 (2H, m), 1.76–1.97 (6H, m), 2.07–2.23 (2H, m), 3.18 (1H, ddd, J=11.23, 5.86, 3.91 Hz), 3.33 (1H, m), 3.84 (3H, s), 4.49 (1H, d, J=15.14 Hz), 4.60 (1H, d, J=15.14 Hz), 4.78 (1H, m), 5.23 (1H, dd, J=9.76, 2.93 Hz), 6.82–6.88 (3H, m), 7.21 (2H, d, J=8.30 Hz), 7.47 (2H, d, J=8.30 Hz)

Example 12

Synthesis of 6-(3-cyclopentyloxy-4-methoxyphenyl)-3-(2-quinolylmethyl)-3,4,5 6-tetrahydro-2H-1,3-oxazin-2-one (Compound No. 12 of Table 1)

To a solution of the 6-(3-cyclopentyloxy-4-methoxyphenyl)-3,4,5,6-tetrahydro-2H-1,3-oxazin-2-one (0.50 g, 1.72 mM) produced in Example 2 in dried N,N-dimethylformamide (23 ml) were added sodium hydride (60%) (0.15 g, 3.78 mM) and 2-chloromethylquinoline hydrochloride (0.37 g, 1.72 mM). The solution was stirred at room temperature for one night. The reaction solution was carefully poured into ice water, then was extracted with methylene chloride. The extract was dried over anhydrous sodium sulfate, and the solvent was removed in vacuo. The residue obtained was purified by flash chromatography (SiO$_2$; eluted by 60% ethyl acetate/hexane) to obtain above-described compound 0.63 g (yield 84.9%) as a light yellow solid.

$^1$H-NMR (400 MHz, CDCl$_3$) δ1.56–1.61 (2H, m), 1.78–1.95 (6H, m), 2.13–2.25 (2H, m), 3.39–3.44 (1H, m), 3.50–3.57 (1H, m), 3.84 (3H, s), 4.78 (1H, m), 4.83 (1H, d, J=15.63 Hz), 4.96 (1H, d, J=15.63 Hz), 5.30 (1H, dd, J=9.28, 2.93 Hz), 6.84 (1H, d, J=8.30 Hz), 6.89–6.92 (2H, m), 7.52–7.56 (2H, m), 7.72 (1H, t, J=7.81 Hz), 7.81 (1H, d, J=7.81 Hz), 8.05 (1H, d, J=8.30 Hz), 8.16 (1H, d, J=8.30 Hz)

Example 13

Synthesis of 6-(3-cyclopentyloxy-4-methoxyphenyl)-3-(1-naphthylmethyl)-3,4,5,6-tetrahydro-2H-1 3-oxazin-2-one (Compound No. 13 of Table 1)

According to the same procedure as in Example 10, using 1-chloromethylnaphthalene instead of methyl iodide, the above-described compound (yield 36.2%) was obtained as a light yellow solid.

$^1$H-NMR (400 MHz, CDCl$_3$) δ1.56–1.60 (2H, m), 1.80–1.93 (6H, m), 2.07–2.13 (2H, m), 3.13–3.17 (2H, m), 3.83 (3H, s), 4.76 (1H, m), 5.00 (1H, d, J=15.13 Hz), 5.17 (1H, dd, J=8.30, 3.90 Hz), 5.25 (1H, d, J=15.13 Hz), 6.80 (1H, d, J=7.81 Hz), 6.83 (1H, dd, J=7.81, 1.46 Hz), 6.87 (1H, d, J=1.46 Hz), 7.39–7.60 (4H, m), 7.83 (1H, d, J=7.82 Hz), 7.89 (1H, d, J=7.32 Hz), 8.20 (1H, d, J=8.30 Hz)

Example 14

Synthesis of 6-(3-cyclopentyloxy-4-methoxyphenyl)-3-(4-pyridylmethyl)-3,4,5,6-tetrahydro-2H-1,3-oxazin-2-one (Compound No. 14 of Table 1)

According to the same procedure as in Example 12, using 4-chloromethylpyridine hydrochloride instead of 2-chloromethylquinoline hydrochloride, the above-described compound (yield 81.0%) was obtained as a yellow solid.

$^1$H-NMR (400 MHz, CDCl$_3$) δ1.59–1.65 (2H, m), 1.79–1.97 (6H, m), 2.16–2.28 (2H, m), 3.22 (1H, ddd, J=11.23, 5.37, 3.91 Hz), 3.36–3.43 (1H, m), 3.85 (3H, s), 4.55 (1H, d, J=15.63 Hz), 4.67 (1H, d, J=15.63 Hz), 4.80 (1H, m), 5.29 (1H, dd, J=9.76, 2.92 Hz), 6.85 (1H, d, J=8.30 Hz), 6.87–6.91 (2H, m), 7.22 (2H, d, J=4.88 Hz), 8.58 (2H, d, J=4.88 Hz)

Example 15

Synthesis of 6-(3-cyclopentyloxy-4-methoxyphenyl)-3-(2-naphthylmethyl)-3,4,5,6-tetrahydro-2H-1,3-oxazin-2-one (Compound No. 15 of Table 1)

According to the same procedure as in Example 10, using 2-bromomethylnaphthalene instead of methyl iodide, the above-described compound (yield 100%) was obtained as a light yellow solid.

$^1$H-NMR (400 MHz, CDCl$_3$) δ1.54–1.61 (2H, m), 1.78–1.94 (6H, m), 2.10–2.18 (2H, m), 3.23 (1H, ddd, J=11.72, 5.37, 3.91 Hz), 3.35 (1H, ddd, J=11.72, 10.25, 5.37 Hz), 3.84 (3H, s), 4.73 (1H, d, J=15.14 Hz), 4.78 (1H, m), 4.82 (1H, d, J=15.14 Hz), 5.25 (1H, dd, J=9.76, 3.41 Hz), 6.83 (1H, d, J=8.30 Hz), 6.87 (1H, dd, J=8.30, 1.96 Hz), 6.90 (1H, d, J=1.96 Hz), 7.46–7.51 (3H, m), 7.73 (1H, s), 7.80–7.84 (3H, m)

Example 16

Synthesis of 6-(3-cyclopentyloxy-4-methoxyphenyl)-3-(2-pyridylmethyl)-2H-1,3-oxazin-2-one (Compound No. 16 of Table 1)

According to the same procedure as in Example 12, using 2-chloromethylpyridine hydrochloride instead of 2-chloromethylquinoline hydrochloride, the above-described compound (yield 63.9%) was obtained as a yellow oil. This compound was purified by flash chromatography (Al$_2$O$_3$; eluted by 3% ethyl acetate/methylene chloride).

$^1$H-NMR (400 MHz, CDCl$_3$) δ1.60 (2H, m), 1.79–1.90 (6H, m), 2.13–2.25 (2H, m), 3.41 (1H, ddd, J=11.72, 5.37, 3.91 Hz), 3.50–3.57 (1H, m), 3.84 (3H, s), 4.67 (1H, d, J=15.63 Hz), 4.74 (1H, d, J=15.63 Hz), 4.78 (1H, m), 5.27 (1H, dd, J=9.77, 3.42 Hz), 6.84 (1H, d, J=8.30 Hz), 6.88 (1H, dd, J=8.30, 1.95 Hz), 6.91 (1H, d, J=1.95 Hz), 7.20–7.27 (1H, m), 7.39–7.41 (1H, dd, J=6.35, 3.42 Hz), 7.66–7.71 (1H, m), 8.54 (1H, m)

Example 17

Synthesis of 3-butyl-6-(3-cyclopentyloxy-4-methoxyphenyl)-3,4,5,6-tetrahydro-2H-1,3-oxazin-2-one (Compound No. 17 of Table 1)

According to the same procedure as in Example 10, using butyl iodide instead of methyl iodide, the above-described compound (yield 83.3%) was obtained as a brown oil.

$^1$H-NMR (400 MHz, CDCl$_3$) δ0.95 (3H, t, J=7.33 Hz), 1.35 (2H, m, J=7.33 Hz), 1.55–1.66 (4H, m), 1.79–1.96 (6H, m), 2.11–2.24 (2H, m), 3.26 (1H, ddd, J=11.72, 5.37, 3.91 Hz), 3.31–3.47 (3H, m), 3.84 (3H, s), 4.79 (1H, m), 5.20 (1H, dd, J=9.76, 2.93 Hz), 6.83 (1H, d, J=8.30 Hz), 6.87 (1H, dd, J=8.30, 1.47 Hz), 6.89 (1H, d, J=1.47 Hz)

Example 18

Synthesis of 3-benzoyl-6-(3-cyclopentyloxy-4-methoxyphenyl)-3,4,5,6-tetrahydro-2H-1,3-oxazin-2-one (Compound No. 18 of Table 1)

According to the same procedure as in Example 10, using benzoyl chloride instead of methyl iodide, the above-described compound (yield 40.7%) was obtained as a brown oil.

$^1$H-NMR (400 MHz, CDCl$_3$) δ1.55–1.64 (2H, m), 1.80–1.96 (6H, m), 2.29–2.37 (1H, m), 2.44–2.50 (1H, m), 3.79–3.85 (1H, m), 3.86 (3H, s), 4.13 (1H, ddd, J=12.69, 6.35, 3.42 Hz), 4.81 (1H, m), 5.42 (1H, dd, J=9.77, 2.45 Hz), 6.88–6.95 (3H, m), 7.41 (2H, m), 7.48–7.50 (1H, m), 7.58 (2H, m)

Example 19

Synthesis of 6-(3-cyclopentyloxy-4-methoxyphenyl)-3-(ethoxycarbonylmethyl)-3,4,5,6-tetrahydro-2H-1,3-oxazin-2-one (Compound No. 19 of Table 1)

According to the same procedure as in Example 10, using ethyl bromoacetate instead of methyl iodide, the above-described compound (yield 78.6%) was obtained as a brown oil.

$^1$H-NMR (400 MHz, CDCl$_3$) δ1.30 (3H, t, J=7.32 Hz), 1.59–1.62 (2H, m), 1.81–1.97 (6H, m), 2.24 (2H, m), 3.34 (1H, ddd, J=10.74, 4.39, 4.39 Hz), 3.58 (1H, m), 3.84 (3H, s), 4.07 (1H, d, J=17.06 Hz), 4.19 (1H, d, J=17.06 Hz), 4.23 (2H, q, J=7.32 Hz), 4.80 (1H, m), 5.30 (1H, t, J=6.35 Hz), 6.85 (1H, d, J=8.30 Hz), 6.89 (1H, dd, J=8.30,1.96 Hz), 6.91 (1H, d, J=1.96 Hz)

Example 20

Synthesis of 6-(3-cyclopentyloxy-4-methoxyphenyl)-3-(3-pyridylmethyl)-3,4,5,6-tetrahydro-2H-1,3-oxazin-2-one (Compound No. 20 of Table 1)

According to the same procedure as in Example 12, using 3-chloromethylpyridine hydrochloride instead of 2-chloromethylquinoline hydrochloride, the above-described compound (yield 59.2%) was obtained as a yellow oil. This compound was purified by flash chromatography (Al$_2$O$_3$; eluted by gradient in range from ethyl acetate to 5% methanol/ethyl acetate).

$^1$H-NMR (400 MHz, CDCl$_3$) δ1.57–1.61 (2H, m), 1.77–1.95 (6H, m), 2.11–2.23 (2H, m), 3.22 (1H, ddd, J=11.23, 5.37, 3.42 Hz), 3.39 (1H, ddd, J=11.23, 11.23, 5.37 Hz), 3.83 (3H, s), 4.54 (1H, d, J=15.13 Hz), 4.66 (1H, d, J=15.13 Hz), 4.78 (1H, m), 5.24 (1H, dd, J=9.77, 2.93 Hz), 6.82–6.88 (3H, m), 7.29 (1H, dd, J=7.81, 4.88 Hz), 7.73 (1H, d, J=7.81 Hz), 8.56 (1H, dd, J=4.88, 1.47 Hz), 8.57 (1H, d, J=1.96 Hz)

Example 21

Synthesis of 6-(3-cyclopentyloxy-4-methoxyphenyl)-3,6-dimethyl-3,4,5,6-tetrahydro-2H-1,3-oxazin-2-one (Compound No. 21 of Table 1)

According to the same procedure as in Example 8, using the 6-(3-cyclopentyloxy-4-methoxyphenyl)-6-methyl-3,4,5,6-tetrahydro-2H-1,3-oxazin-2-one produced in Example 6 instead of 6-(3,4-dimethoxyphenyl)-3,4,5,6-tetrahydro-2H-1,3-oxazin-2-one, the above-described compound (yield 99.4%) was obtained as a yellow solid.

$^1$H-NMR (400 MHz, CDCl$_3$) δ1.58–1.65 (2H, m), 1.62 (3H, s), 1.81–1.99 (6H, m), 2.19 (1H, ddd, J=14.16, 11.23, 5.86 Hz), 2.33 (1H, ddd, J=14.16, 4.88, 2.93 Hz), 2.90 (3H, s), 3.00 (1H, ddd, J=11.23, 11.23, 4.88 Hz), 3.11 (1H, ddd, J=11.23, 5.86, 2.93 Hz), 3.84 (3H, s), 4.80 (1H, m), 6.81 (1H, dd, J=8.30, 1.95 Hz), 6.85 (1H, d, J=8.30 Hz), 6.89 (1H, d, J=1.95 Hz)

Example 22

Synthesis of 6-(3-cyclopentyloxy-4-methoxyphenyl)-6-methyl-3-(4-pyridylmethyl)-3,4,5,6-tetrahydro-2H-1,3-oxazin-2-one (Compound No. 22 of Table 1)

According to the same procedure as in Example 21, using 4-chloromethylpyridine hydrochloride instead of methyl iodide, the above-described compound (yield 77.4%) was obtained as an orange solid. This compound was purified by flash chromatography (Al$_2$O$_3$; eluted by gradient in range from ethyl acetate to 5% methanol/ethyl acetate).

$^1$H-NMR (400 MHz, CDCl$_3$) δ1.59 (2H, m), 1.65 (3H, s), 1.81–1.94 (6H, m), 2.22–2.28 (1H, m), 2.42 (1H, ddd, J=14.16, 4.88, 2.44 Hz), 3.00–3.06 (2H, m), 4.36 (1H, d, J=16.11 Hz), 4.61 (1H, d, J=16.11 Hz), 4.78 (1H, m), 6.85 (2H, s), 6.90 (2H, d, J=5.86 Hz), 6.94 (1H, s), 8.43 (2H, d, J=5.86 Hz)

Example 23

Synthesis of 6-(4-methoxy-3-phenethyloxyphenyl)-3,4,5,6-tetrahydro-2H-1,3-oxazin-2-one (Compound No. 23 of Table 1)

(1) Synthesis of 4-methoxy-3-phenethyloxybenzaldehyde

According to the same procedure as in Example 4(1), using phenethyl alcohol, instead of cyclopropylcarbinol, 4-methoxy-3-phenethyloxybenzaldehyde 2.88 g (yield 85.5%) was obtained as a light yellow oil.

$^1$H-NMR (400 MHz, CDCl$_3$) δ3.19 (2H, t, J=7.33 Hz), 4.28 (2H, t, J=7.33 Hz), 6.98 (1H, d, J=8.30 Hz), 7.23–7.35

(5H, m), 7.40 (1H, d, J=1.96 Hz), 7.46 (1H, dd, J=8.30, 1.96 Hz), 9.83 (1H, s)

(2) Synthesis of 3-hydroxy-3-(4-methoxy-3-phenethyloxyphenyl)propiononitrile According to the same procedure as in Example 1(1) using 4-methoxy-3-phenethyloxybenzaldehyde, instead of 3,4-dimethoxybenzaldehyde, 3-hydroxy-3-(4-methoxy-3-phenethyloxyphenyl)propiononitrile was obtained as a yellow oil.

$^1$H-NMR (400 MHz, CDCl$_3$) δ2.70 (1H, dd, J=16.60, 5.86 Hz), 2.75 (1H, dd, J=16.60, 6.83 Hz), 3.17 (2H, t, J=7.33 Hz), 3.87 (3H, s), 4.23 (1H, t, J=7.33 Hz), 4.95 (1H, m), 6.85–6.93 (3H, m), 7.22–7.34 (5H, m)

(3) Synthesis of 6-(4-methoxy-3-phenethyloxyphenyl)-3,4,5,6-tetrahydro-2H-1 3-oxazin-2-one According to the same procedure as in Example 1(2) to (3), using 3-hydroxy-3-(4-methoxy-3-phenethyloxyphenyl) propiononitrile instead of 3-(3,4-dimethoxyphenyl)-3-hydroxypropiononitrile, the above-described compound (yield 68.9%) was obtained as a brown solid.

$^1$H-NMR (400 MHz, CDCl$_3$) δ2.02–2.11 (1H, m), 2.13–2.19 (1H, m), 3.17 (2H, t, J=7.32 Hz), 3.35–3.41 (1H, m), 3.47 (1H, ddd, J=11.23, 11.23, 4.88 Hz), 3.87 (3H, s), 4.20–4.24 (2H, m), 5.24 (1H, dd, J=9.76, 2.44 Hz), 5.37 (1H, broad s), 6.86–6.92 (3H, m), 7.22–7.36 (5H, m)

Example 24

Synthesis of 6-[3-(2-indanyloxy)-4-methoxyphenyl]-3,4,5,6-tetrahydro-2H-1,3-oxazin-2-one (Compound No. 24 of Table 1)

(1) Synthesis of 3-(2-indanyloxy)-4-methoxybenzaldehyde

According to the same procedure as in Example 4(1), using 2-indanol instead of cyclopropylcarbinol, 3-(2-indanyloxy)-4-methoxybenzaldehyde (yield 62.6%) was obtained as a light yellow solid.

$^1$H-NMR (400 MHz, CDCl$_3$) δ3.25 (2H, dd, J=16.60, 3.42 Hz), 3.46 (2H, dd, J=16.60, 6.35 Hz), 3.90 (3H, s), 5.26 (1H, m), 6.98 (1H, d, J=8.30 Hz), 7.17–7.21 (2H, m), 7.22–7.25 (2H, m), 7.46–7.49 (2H, m), 9.87 (1H, s)

(2) Synthesis of 3-hydroxy-3-[3-(2-indanyloxy)-4-methoxyphenyl]propiononitrile According to the same procedure as in Example 1(1), using 3-(2-indanyloxy)-4-methoxybenzaldehyde instead of 3,4-dimethoxybenzaldehyde, 3-hydroxy-3-[3-(2-indanyloxy)-4-methoxyphenyl]propiononitrile was obtained as a yellow oil.

$^1$H-NMR (400 MHz, CDCl$_3$) δ2.76 (2H, d, J=6.35 Hz), 3.23 (2H, dd, J=16.60, 3.90 Hz), 3.39 (2H, ddd, J=16.60, 6.35, 2.93 Hz), 3.81 (3H, s), 4.98 (1H, t, J=6.35 Hz), 5.20 (1H, m), 6.87 (1H, d, J=8.30 Hz), 6.93 (1H, dd, J=8.30,1.95 Hz), 7.01 (1H, d, J=1.95 Hz), 7.16–7.24 (4H, m)

(3) Synthesis of 6-[3-(2-indanyloxy)-4-methoxyphenyl]-3,4,5,6-tetrahydro-2H-1, 3-oxazin-2-one According to the same procedure as in Example 1(2) to (3), using 3-hydroxy-3-[3-(2-indanyloxy)-4-methoxyphenyl]propiononitrile instead of 3-(3,4-dimethoxyphenyl)-3-hydroxypropiononitrile, the above-described compound (yield 74.2%) was obtained as a light brown solid.

$^1$H-NMR (400 MHz, CDCl$_3$) δ2.08–2.16 (1H, m), 2.19–2.23 (1H, m), 3.24 (2H, dd, J=16.60, 3.42 Hz), 3.38 (2H, dd, J=16.60, 6.34 Hz), 3.38–3.68 (2H, m), 3.82 (3H, s), 5.21 (1H, m), 5.28 (1H, dd, J=10.25, 2.44 Hz), 5.43 (1H, broad s), 6.87–6.99 (3H, m), 7.16–7.25 (4H, m)

Example 25

Synthesis of 6-[3-(2-indanyloxy)-4-methoxyphenyl]-3-methyl-3,4,5,6-tetrahydro-2H-1, 3-oxazin-2-one (Compound No. 25 of Table 1)

According to the same procedure as in Example 8, using the 6-[3-(2-indanyloxy)-4-methoxyphenyl]-3,4,5,6-tetrahydro-2H-1,3-oxazin-2-one produced in Example 24 instead of 6-(3,4-dimethoxyphenyl)-3,4,5,6-tetrahydro-2H-1,3-oxazin-2-one, the above-described compound (yield 100%) was obtained as a yellow solid.

$^1$H-NMR (400 MHz, CDCl$_3$) δ2.16–2.23 (2H, m), 3.05 (3H, s), 3.23 (2H, dd, J=16.60, 2.93 Hz), 3.27 (1H, ddd, J=11.72, 5.37, 3.42 Hz), 3.37 (2H, dd, J=16.60, 6.35 Hz), 3.49 (1H, ddd, J=11.72, 11.72, 5.86 Hz), 3.81 (3H, s), 5.18–5.24 (2H, m), 6.86 (1H, d, J=8.30 Hz), 6.93 (1H, dd, J=8.30, 1.96 Hz), 6.96 (1H, d, J=1.96 Hz), 7.15–7.19 (2H, m), 7.22–7.24 (2H, m)

Example 26

Synthesis of 6-(3-cyclopentyloxy-4-methoxyphenyl)-6-ethyl-3,4,5,6-tetrahydro-2H-1,3-oxazin-2-one (Compound No. 26 of Table 1)

(1) Synthesis of 3'-cyclopentyloxy-4'-methoxypropiophenone

According to the same procedure as in Example 6(1), using ethyl magnesium bromide instead of methyl magnesium bromide, 3'-cyclopentyloxy-4'-methoxypropiophenone (yield 81.2%) was obtained as a brown oil.

$^1$H-NMR (400 MHz, CDCl$_3$) δ1.22 (3H, t, J=7.32 Hz), 1.57–1.68 (2H, m), 1.76–2.04 (6H, m), 2.96 (2H, q, J=7.32 Hz), 3.91 (3H, s), 4.85 (1H, m), 6.88 (1H, d, J=8.30 Hz), 7.53 (1H, d, J=1.96 Hz), 7.57 (1H, dd, J=8.30, 1.96 Hz)

(2) Synthesis of 3-(3-cyclopentyloxy-4-methoxyphenyl)-3-hydroxyvaleronitrile According to the same procedure as in Example 1(1), using 3'-cyclopentyloxy-4'-methoxypropiophenone instead of 3,4-dimethoxybenzaldehyde, 3-(3-cyclopentyloxy-4-methoxyphenyl)-3-hydroxyvaleronitrile was obtained as a yellow oil.

$^1$H-NMR (400 MHz, CDCl$_3$) δ0.83 (3H, t, J=7.32 Hz), 1.54–1.63 (2H, m), 1.82–1.95 (6H, m), 2.01 (2H, q, J=7.32 Hz), 2.79 (1H, d, J=16.60 Hz), 2.84 (1H, d, J=16.60 Hz), 3.85 (3H, s), 4.80 (1H, m), 6.85 (1H, d, J=8.30 Hz), 6.90 (1H, dd, J=8.30, 1.95 Hz), 6.99 (1H, d, J=1.95 Hz)

(3) Synthesis of 6-(3-cyclopentyloxy-4-methoxyphenyl)-6-ethyl-3,4,5,6-tetrahydro-2H-1,3-oxazin-2-one According to the same procedure as in Example 1(2) to (3), using 3-(3-cyclopentyloxy-4-methoxyphenyl)-3-hydroxyvaleronitrile instead of 3-(3,4-dimethoxyphenyl)-3- hydroxypropiononitrile, the above-described compound (yield 21.8%) was obtained as a light yellow solid.

$^1$H-NMR (400 MHz, CDCl$_3$) δ0.84 (3H, t, J=7.33 Hz), 1.60 (2H, m), 1.82–1.98 (8H, m), 2.14 (1H, ddd, J=11.72, 11.72, 5.37 Hz), 2.25 (1H, d, J=13.67 Hz), 3.01 (1H, ddd, J=11.72, 11.72, 4.39 Hz), 3.21–3.24 (1H, m), 3.84 (3H, s), 4.79 (1H, m), 5.18 (1H, broad), 6.77–6.90 (3H, m)

Example 27

Synthesis of 6-(3,4-dimethoxyphenyl)-6-(2-thiazolyl)-3,4,5,6-tetrahydro-2H-1,3-oxazin-2-one (Compound No. 27 of Table 1)

(1) Synthesis of 3,4-dimethoxyphenyl 2-thiazolyl ketone

A hexane solution of butyllithium (9.50 mM) was dissolved in dried diethyl ether (6.5 ml) and cooled to −78° C. A solution of 2-bromothiazole (1.03 g, 6.13 mM) in diethyl ether (0.5 ml) was dropped into this solution. The solution was stirred at that temperature for 30 minutes, then a solution of 3,4-dimethoxybenzonitrile (1.00 g, 6.13 mM) in diethyl ether (3.0 ml) was added and the resultant mixture stirred for a further 6 hours. 1N Hydrochloric acid (20 ml) was poured into the solution obtained, which was then warmed to room temperature and stirred for 30 minutes, then a saturated sodium hydrogencarbonate solution was added to neutralize the solution and extraction was performed with ethyl acetate. Next, the organic layer was washed with brine and dried over anhydrous magnesium sulfate, then the solvent was removed in vacuo to obtain a dark red solid residue. The residue was purified by flash chromatography (SiO$_2$: eluted by gradient from 50% hexane/methylene chloride to 25% hexane/methylene chloride). The solvent was removed in vacuo and the resultant product was dried to obtain 3,4-dimethoxyphenyl 2-thiazolyl ketone 0.71 g (yield 46.5%) as a red solid.

$^1$H-NMR (400 MHz, CDCl$_3$) δ3.99 (6H, s), 6.98 (1H, d, J=8.79 Hz), 7.70 (1H, d, J=3.42 Hz), 8.02 (1H, d, J=1.96 Hz), 8.08 (1H, d, J=3.42 Hz), 8.43 (1H, dd, J=8.79, 1.96 Hz)

(2) Synthesis of 3-(3,4-dimethoxyphenyl)-3-hydroxy-3-(2-thiazolyl)propiononitrile According to the same procedure as in Example 1, using 3,4-dimethoxyphenyl 2-thiazolyl ketone instead of 3,4-dimethoxybenzaldehyde, 3-(3,4-dimethoxyphenyl)-3-hydroxy-3-(2-thiazolyl)propiononitrile was obtained as a yellow oil.

$^1$H-NMR (400 MHz, CDCl$_3$) δ3.40 (1H, d, J=16.60 Hz), 3.51 (1H, d, J=16.60 Hz), 3.87 (6H, s), 4.05 (1H, broad s), 6.85 (1H, d, J=8.30 Hz), 7.05 (1H, dd, J=8.30, 2.44 Hz), 7.13 (1H, d, J=2.44 Hz), 7.36 (1H, d, J=3,42 Hz), 7.76 (1H, d, J=3,42 Hz)

(3) Synthesis of 6-(3,4-dimethoxyphenyl)-6-(2-thiazolyl)-3,4,5,6-tetrahydro-2H-1,3-oxazin-2-one According to the same procedure as in Example 1(2) to (3), using 3-(3,4-dimethoxyphenyl)-3-hydroxy-3-(2-thiazolyl)propiononitrile instead of 3-(3,4-dimethoxyphenyl)-3-hydroxypropiononitrile, the above-described compound (yield 38.3%) was obtained as a yellow solid.

$^1$H-NMR (400 MHz, CDCl$_3$) δ2.65 (1H, ddd, J=14.16, 7.82, 5.86 Hz), 2.97 (1H, ddd, J=14.16, 5.86, 5.86 Hz), 3.24–3.31 (1H, m), 3.34–3.40 (1H, m), 3.86 (3H, s), 3.88 (3H, s), 5.53 (1H, broad s), 6.84 (1H, d, J=8.30 Hz), 7.08 (1H, dd, J=8.30, 1.95 Hz), 7.12 (1H, d, J=1.95 Hz), 7.35 (1H, d, J=2.93 Hz), 7.77 (1H, d, J=2.93 Hz)

Example 28

Synthesis of 6-(3-cyclopentyloxy-4-methoxyphenyl)-3-ethyl-3,4,5,6-tetrahydro-2H-1,3-oxazin-2-one (Compound No. 28 of Table 1)

According to the same procedure as in Example 10, using ethyl iodide instead of methyl iodide, the above-described compound (yield 98.1%) was obtained as a yellow oil.

$^1$H-NMR (400 MHz, CDCl$_3$) δ1.20 (3H, t, J=7.33 Hz), 1.26–1.66 (2H, m), 1.78–1.96 (6H, m), 2.11–2.25 (2H, m), 3.27 (1H, ddd, J=11.23, 5.37, 3.42 Hz), 3.41–3.47 (1H, m), 3,44 (2H, q, J=7.33 Hz), 3.84 (3H, s), 4.79 (1H, m), 5.20 (1H, dd, J=9.77, 2.93 Hz), 6.83–6.89 (3H, m)

Example 29

Synthesis of 6-(3-cyclopentyloxy-4-methoxyphenyl)-6-(2-thienyl)-3,4,5, 6-tetrahydro-2H-1,3-oxazin-2-one (Compound No. 29 of Table 1)

(1) Synthesis of 3-cyclopentyloxy-4-methoxyphenyl 2-thienyl ketone

According to the same procedure as in Example 7(1), using 2-thienyllithium instead of phenyllithium, 3-cyclopentyloxy-4-methoxyphenyl 2-thienyl ketone (yield 51.3%) was obtained as a yellow oil.

$^1$H-NMR (400 MHz, CDCl$_3$) δ1.54–1.66 (2H, m), 1.80–2.03 (6H, m), 3.93 (3H, s), 4.85 (1H, m), 6.93 (1H, d, J=8.30 Hz), 7.17 (1H, dd, J=4.40 Hz), 7.46 (1H, d, J=1.95 Hz), 7.54 (1H, dd, J=8.30, 1.95 Hz), 7.68 (1H, d, J=4.40 Hz), 7.69 (1H, d, J=4.40 Hz)

(2) Synthesis of 3-(3-cyclopentyloxy-4-methoxyphenyl)-3-hydroxy-3-(2-thienyl) propiononitrile According to the same procedure as in Example 1(1), using 3-cyclopentyloxy-4-methoxyphenyl 2-thienyl ketone instead of 3cyclopentyloxy-4-methoxyphenyl/-3-hydroxy-3-(2-thienyl)propiononitrile was obtained as a yellow oil.

$^1$H-NMR (400 MHz, CDCl$_3$) δ1.53–1.61 (2H, m), 1.77–1.91 (6H, m), 3.26 (1H, d, J=16.60 Hz), 3.31 (1H, d, J=16.60 Hz), 3.85 (3H, s), 4.74 (1H, m), 6.85 (1H, d, J=8.30 Hz), 6.96 (4H, m), 7.31 (1H, dd, J=4.88, 0.98 Hz)

(3) Synthesis of 6-(3-cyclopentyloxy-4-methoxyphenyl)-6-(2-thienyl)-3,4,5,6-tetrahydro-2H-1,3-oxazin-2-one According to the same procedure as in Example 1(2) to (3), using 3-(3-cyclopentyloxy-4-methoxyphenyl)-3-hydroxy-3-(2-thienyl)propiononitrile instead of 3-(3,4-dimethoxyphenyl)-3-hydroxypropiononitrile, the above-described compound (yield 35.4%) was obtained as a brown solid.

$^1$H-NMR (400 MHz, CDCl$_3$) δ1.59–1.61 (2H, m), 1.81–1.91 (6H, m), 2.66 (2H, t, J=5.86 Hz), 3.20–3.26 (1H, m), 3.35 (1H, ddd, J=11.23, 5.86, 2.44 Hz), 3.84 (3H, s), 4.76 (1H, m), 5.46 (1H, broad s), 6.85 (1H, d, J=8.30 Hz), 6.94–6.97 (3H, m), 6.99 (1H, d, J=1.95 Hz), 7.28 (1H, dd, J=3.42,3.42 Hz)

Example 30

Synthesis of 6-butyl-6-(3-cyclopentyloxy-4-methoxyphenyl)-3,4,5 6-tetrahydro-2H-1, 3-oxazin-2-one (Compound No. 30 of Table 1)

(1) Synthesis of 3'-cyclopentyloxy-4'-methoxyvaleriophenone

According to the same procedure as in Example 7(1), using butyllithium instead of phenyllithium, 3'-cyclopentyloxy-4'-methoxyvaleriophenone (yield 78.9%) was obtained as a light green oil.

$^1$H-NMR (400 MHz, CDCl$_3$) δ0.95 (3H, t, J=7.32 Hz), 1.41 (2H, m), 1.60–1.64 (2H, m), 1.71 (2H, m), 1.79–2.00 (6H, m), 2.91 (2H, t, J=7.32 Hz), 3.90 (3H, s), 4.85 (1H, m), 6.87 (1H, d, J=8.30 Hz), 7.53 (1H, d, J=1.95 Hz), 7.56 (1H, dd, J=8.30, 1.95 Hz)

(2) Synthesis of 3-(3-cyclopentyloxy-4-methoxyphenyl)-3-hydroxyheptanonitrile

According to the same procedure as in Example 1(1), using 3'-cyclopentyloxy-4'-methoxyvaleriophenone instead of 3,4-dimethoxybenzaldehyde, 3-(3-cyclopentyloxy-4-methoxyphenyl)-3-hydroxyheptanonitrile was obtained as a yellow oil.

$^1$H-NMR (400 MHz, CDCl$_3$) δ0.86 (3H, t, J=7.32 Hz), 1.11–1.34 (4H, m), 1.54–1.63 (2H, m), 1.79–1.99 (8H, m), 2.78 (1H, d, J=16.60 Hz), 2.83 (1H, d, J=16.60 Hz), 3.85 (3H, s), 4.80 (1H, m), 6.85 (1H, d, J=8.30 Hz), 6.90 (1H, dd, J=8.30, 2.44 Hz), 6.98 (1H, d, J=2.44 Hz)

(3) Synthesis of 6-butyl-6-(3-cyclopentyloxy-4-methoxyphenyl)-3,4,5,6-tetrahydro-2H-1,3-oxazin-2-one According to the same procedure as in Example 1(2) to (3), using 3-(3-cyclopentyloxy-4-methoxyphenyl)-3-hydroxyheptanonitrile instead of 3-(3,4-dimethoxyphenyl)-3-hydroxypropiononitrile, the above-described compound (yield 40.6%) was obtained as a colorless solid.

$^1$H-NMR (400 MHz, CDCl$_3$) δ0.82 (3H, t, J=7.32 Hz), 1.19–1.60 (6H, m), 1.73–1.93 (8H, m), 2.13 (1H, ddd, J=14.16, 11.72, 5.37 Hz), 2.22–2.25 (1H, m), 2.99 (1H, ddd, J=11.72, 11.72, 4.40 Hz), 3.11–3.21 (1H, m), 3.84 (3H, s), 4.79 (1H, m), 5.75 (1H, broad), 6.79 (1H, dd, J=8.30, 1.95 Hz), 6.84 (1H, d, J=1.95 Hz), 6.85 (1H, d, J=8.30 Hz)

Example 31

Synthesis of 6-(3-cyclopentyloxy-4-methoxyphenyl)-6-(2-thiazolyl)-3,4,5,6-tetrahydro-2H-1,3-oxazin-2-one (Compound No. 31 of Table 1)

(1) Synthesis of 3-cyclopentyloxy-4-methoxybenzonitrile 3-cyclopentyloxy-4-methoxybenzaldehyde (13.00 g, 59.02 mM) and hydroxylamine hydrochloride (8.46 g, 118.04 mM) were dissolved in pyridine (120 ml) and the resultant mixture was heated to reflux for 23 hours. The solution obtained was cooled to room temperature, water (100 ml) was added, then the solution was extracted with ethyl acetate. The organic layer was dried over anhydrous magnesium sulfate, then the solvent was removed in vacuo to obtain a green oily residue. The residue was purified by flash chromatography (SiO$_2$: eluted by 20% ethyl acetate/hexane). The solvent was removed in vacuo and the resultant product was dried to obtain 3-cyclopentyloxy-4-methoxybenzaldehyde oxime 14.57 g as a colorless oil. The 3-cyclopentyloxy-4-methoxybenzaldehyde oxime (14.57 g) thus obtained was dissolved in acetic acid (130 ml) and the resultant mixture was heated to reflux for 22 hours. The solution obtained was ice cooled, then a saturated sodium hydrogencarbonate solution was added to neutralize it. The solution was extracted with ethyl acetate, the organic layer was dried over anhydrous magnesium sulfate, and the solvent was removed in vacuo to obtain a red solid residue. The residue was purified by flash chromatography (SiO$_2$: eluted by 25% ethyl acetate/hexane). The solvent was removed in vacuo and the result dried to obtain 3-cyclopentyloxy-4-methoxybenzonitrile 9.60 g (yield 75.2%) as a yellow-green oil.

$^1$H-NMR (400 MHz, CDCl$_3$) δ1.55–1.69 (2H, m), 1.79–2.05 (6H, m), 3.89 (3H, s), 4.76 (1H, m), 6.88 (1H, d, J=8.30 Hz), 7.07 (1H, d, J=1.96 Hz), 7.25 (1H, dd, J=8.30, 1.96 Hz)

(2) Synthesis of 3-cyclopentyloxy-4-methoxyphenyl 2-thiazolyl ketone

According to the same procedure as in Example 27(1), using 3-cyclopentyloxy-4-methoxybenzonitrile instead of 3,4-dimethoxybenzonitrile, 3-cyclopentyloxy-4-methoxyphenyl 2-thiazolyl ketone (yield 67.0%) was obtained as a red oil.

$^1$H-NMR (400 MHz, CDCl$_3$) δ1.58–1.68 (2H, m), 1.81–2.07 (6H, m), 3.94 (3H, s), 4.90 (1H, m), 6.96 (1H, d, J=8.79 Hz), 7.68 (1H, d, J=2.93 Hz), 8.05 (1H, d, J=1.95 Hz), 8.07 (1H, d, J=2.93 Hz), 8.36 (1H, dd, J=8.79, 1.95 Hz)

(3) Synthesis of 3-(3-cyclopentyloxy-4-methoxyphenyl)-3-hydroxy-3-(2-thiazolyl)propiononitrile According to the same procedure as in Example 1(1), using 3-cyclopentyloxy-4-methoxyphenyl 2-thiazolyl ketone instead of 3,4-dimethoxybenzaldehyde, 3-(3-cyclopentyloxy-4-methoxyphenyl)-3-hydroxy-3-(2-thiazolyl)propiononitrile was obtained as a yellow oil.

$^1$H-NMR (400 MHz, CDCl$_3$) δ1.54–1.62 (2H, m), 1.79–1.93 (6H, m), 3.38 (1H, d, J=16.60 Hz), 3.50 (1H, d, J=16.60 Hz), 3.73 (1H, broad s), 3.83 (3H, s), 4.75 (1H, m), 6.85 (1H, d, J=8.30 Hz), 7.03 (1H, dd, J=8.30, 2.44 Hz), 7.09 (1H, d, J=2.44 Hz), 7.37 (1H, d, J=3,42 Hz), 7.77 (1H, d, J=3,42 Hz)

(4) Synthesis of 6-(3-cyclopentyloxy-4-methoxyphenyl)-6-(2-thiazolyl)-3,4,5,6-tetrahydro-2H-1,3-oxazin-2-one According to the same procedure as in Example 1(2) to (3), using 3-(3-cyclopentyloxy-4-methoxyphenyl)-3-hydroxy-3-(2-thiazolyl)propiononitrile instead of 3-(3,4-dimethoxyphenyl)-3-hydroxypropiononitrile, the above-described compound (yield 33.1%) was obtained as a light brown solid.

$^1$H-NMR (400 MHz, CDCl$_3$) δ1.58–1.80 (2H, m), 1.85–1.93 (6H, m), 2.65 (1H, ddd, J=13.68, 7.33, 5.86 Hz), 2.91 (1H, ddd, J=13.68, 5.86, 5.86 Hz), 3.24–3.26 (1H, m), 3.32–3.36 (1H, m), 3.82 (3H, s), 4.77 (1H, m), 6.57 (1H, broad), 6.83 (1H, d, J=8.30 Hz), 7.06 (1H, dd, J=8.30,1.96 Hz), 7.08 (1H, d, J=1.96 Hz), 7.34 (1H, d, J=3.42 Hz), 7.76 (1H, d, J=3.42 Hz)

Example 32

Synthesis of 6-(3-cyclopentyloxy-4-methoxyphenyl)-3-[2-(1-piperidyl)ethyl]-3,4,5,6-tetrahydro-2H-1,3-oxazin-2-one (Compound No. 32 of Table 1)

According to the same procedure as in Example 10, using 1-(2-iodoethyl)piperidine instead of methyl iodide, the above-described compound (yield 78.2%) was obtained as a colorless solid.

$^1$H-NMR (400 MHz, CDCl$_3$) δ1.43 (2H, m), 1.54–1.62 (6H, m), 1.80–1.96 (6H, m), 2.10–2.23 (2H, m), 2.44 (4H, m), 2.57 (2H, m), 3.38 (1H, ddd, J=11.72, 5.37, 3.90 Hz), 3.43–3.56 (3H, m), 3.84 (3H, s), 4.79 (1H, m), 5.21 (1H, dd, J=9.28, 2.93 Hz), 6.83–6.89 (3H, m)

Example 33

Synthesis of 6-(3-cyclopentyloxy-4-methoxyphenyl)-3-[2-(4-morpholino)ethyl]-3,4,5,6-tetrahydro-2H-1,3-oxazin-2-one (Compound No. 33 of Table 1)

According to the same procedure as in Example 10, using 4-(2-iodoethyl) morpholine instead of methyl iodide, the above-described compound (yield 49.9%) was obtained as a light yellow oil.

$^1$H-NMR (400 MHz, CDCl$_3$) δ1.58–1.62 (2H, m), 1.80–1.96 (6H, m), 2.11–2.24 (2H, m), 2.50 (4H, m), 2.59 (2H, t, J=6.35 Hz), 3.36 (1H, ddd, J=11.71, 5.37, 4.39 Hz), 3.42–3.58 (1H, m), 3.53 (2H, t, J=6.35 Hz), 3.69 (4H, t, J=4.39 Hz), 3.84 (3H, s), 4.79 (1H, m), 5.22 (1H, dd, J=9.76, 2.93 Hz), 6.83–6.89 (3H, m)

Example 34

Synthesis of 3-(1-acetyl-3-methyl-2-indolylmethyl)-6-(3-cyclopentyloxy-4-methoxyphenyl)-3,4,5,6-tetrahydro-2H-1,3-oxazin-2-one (Compound No. 34 of Table 1)

According to the same procedure as in Example 10, using 1-acetyl-2-iodomethyl-3-methylindole instead of methyl iodide, the above-described compound (yield 35.2%) was obtained as a yellow solid.

$^1$H-NMR (400 MHz, CDCl$_3$) δ1.56 (3H, s), 1.58–1.60 (2H, m), 1.81–1.92 (6H, m), 2.05–2.19 (2H, m), 2.34 (3H, s), 3.32 (1H, ddd, J=11.72, 5.38, 2.93 Hz), 3,49 (1H, ddd, J=11.72, 10.75, 5.38 Hz), 3.83 (3H, s), 4.43 (1H, d, J=15.14 Hz), 4.73–4.76 (1H, m), 4.76 (1H, d, J=15.14 Hz), 5.19 (1H, dd, J=10.25, 2.44 Hz), 6.80–6.85 (3H, m), 7.11 (1H, dd, J=7.81, 6.84 Hz), 7.20 (1H, dd, J=7.81, 6.84 Hz), 7.33 (1H, d, J=7.81 Hz), 7.53 (1H, d, J=7.81 Hz)

Example 35

Synthesis of 6-(3-cyclopentyloxy-4-methoxyphenyl)-3-(2-furylmethyl)-3,4,5,6-tetrahydro-2H-1,3-oxazin-2-one (Compound No. 35 of Table 1)

According to the same procedure as in Example 10, using 2-iodomethylfuran instead of methyl iodide, the above-described compound (yield 94.1%) was obtained as a light yellow oil.

$^1$H-NMR (400 MHz, CDCl$_3$) δ1.56–1.61 (2H, m), 1.78–1.96 (6H, m), 2.10–2.23 (2H, m), 3.34 (1H, ddd, J=11.72, 5.86, 3.42 Hz), 3,44 (1H, ddd, J=11.72, 11.72, 5.37 Hz), 3.84 (3H, s), 4.56 (1H, d, J=15.63 Hz), 4.62 (1H, d, J=15.63 Hz), 4.77 (1H, m), 5.21 (1H, dd, J=9.77, 2.93 Hz), 6.33–6.35 (2H, m), 6.82–6.88 (3H, m), 7.38 (1H, d, J=0.97 Hz)

Example 36

Synthesis of 6-(3-cyclopentyloxy-4-methoxyphenyl)-6-(3-pyridyl)-3,4,5,6-tetrahydro-2H-1,3-oxazin-2-one (Compound No. 36 of Table 1)

(1) Synthesis of 3-cyclopentyloxy-4-methoxyphenyl 3-pyridyl ketone

According to the same procedure as in Example 31(2), using 3-bromopyridine instead of 2-bromothiazole, 3-cyclopentyloxy-4-methoxyphenyl 3-pyridyl ketone (yield 77.7%) was obtained as a yellow solid.

$^1$H-NMR (400 MHz, CDCl$_3$) δ1.58–1.66 (2H, m), 1.80–2.04 (6H, m), 3.94 (3H, s), 4.85 (1H, m), 6.91 (1H, d, J=8.30 Hz), 7.36 (1H, dd, J=8.30, 1.95 Hz), 7.44 (1H, dd, J=7.82, 4.89 Hz), 7.47 (1H, d, J=1.95 Hz), 8.08 (1H, ddd, J=7.82, 1.95, 1.95 Hz), 8.79 (1H, dd, J=4.89, 1.95 Hz), 8.97 (1H, d, J=1.95 Hz)

(2) Synthesis of 3-(3-cyclopentyloxy-4-methoxyphenyl)-3-hydroxy-3-(3-pyridyl) propiononitrile According to the same procedure as in Example 1(1), using 3-cyclopentyloxy-4-methoxyphenyl 3-pyridyl ketone instead of 3,4-dimethoxybenzaldehyde, 3-(3-cyclopentyloxy-4-methoxyphenyl)-3-hydroxy-3-(3-pyridyl) propiononitrile was obtained as a yellow oil.

$^1$H-NMR (400 MHz, CDCl$_3$) δ1.56–1.59 (2H, m), 1.79–1.87 (6H, m), 3.23 (1H, d, J=16.60 Hz), 3.29 (1H, d, J=16.60 Hz), 3.85 (3H, s), 4.70 (1H, m), 6.84–6.90 (3H, m), 7.30 (1H, dd, J=8.30, 4.88 Hz), 7.76 (1H, ddd, J=8.30, 1.95, 1.95 Hz), 8.54 (1H, dd, J=4.88, 1.95 Hz), 8.62 (1H, s)

(3) Synthesis of 6-(3-cyclopentyloxy-4-methoxyphenyl)-6-(3-pyridyl)-3,4 5,6-tetrahydro-2H-1,3-oxazin-2-one According to the same procedure as in Example 1(2) to (3), using 3-(3-cyclopentyloxy-4-methoxyphenyl)-3-hydroxy-3-(3-pyridyl)propiononitrile instead of 3-(3,4-dimethoxyphenyl)-3-hydroxypropiononitrile, above-described compound (yield 14.9%) was obtained as a brown solid.

$^1$H-NMR (400 MHz, CDCl$_3$) δ1.57 (2H, m), 1.79–1.87 (6H, m), 2.58 (1H, ddd, J=14.16, 7.33, 7.33 Hz), 2.70 (1H, ddd, J=14.16, 5.37, 5.37 Hz), 3.28 (2H, m), 3.83 (3H, s), 4.73 (1H, m), 6.45 (1H, broad), 6.84 (1H, d, J=7.81 Hz), 6.89–6.92 (2H, m), 7.28 (1H, dd, J=8.30, 4.88 Hz), 7.76 (1H, dd, J=8.30, 1.95 Hz), 8.52 (1H, d, J=4.88 Hz), 8.64 (1H, d, J=1.95 Hz)

Example 37

Synthesis of 6-(3-cyclopentyloxy-4-methoxyphenyl)-3-(2-pyrazinylmethyl)-3,4,5,6-tetrahydro-2H-1,3-oxazin-2-one (Compound No. 37 of Table 1)

According to the same procedure as in Example 10, using 2-iodomethylpyrazine instead of methyl iodide, the above-described compound (yield 24.4%) was obtained as a yellow oil.

$^1$H-NMR (400 MHz, CDCl$_3$) δ1.58–1.62 (2H, m), 1.78–1.96 (6H, m), 2.18–2.26 (2H, m), 3.46 (1H, ddd, J=11.23, 5.37, 3.91 Hz), 3.60 (1H, ddd, J=11.23, 11.23, 5.37 Hz), 3.84 (3H, s), 4.69 (1H, d, J=15.62 Hz), 4.76 (1H, d, J=15.62 Hz), 4.76–4.80 (1H, m), 5.29 (1H, dd, J=9.28, 3.42 Hz), 6.83–6.90 (3H, m), 8.52 (2H, s), 8.71 (1H, s)

Example 38

Synthesis of 6-(3-cyclopentyloxy-4-methoxyphenyl)-3-(2-thienylmethyl)-3,4,5 6-tetrahydro-2H-1,3-oxazin-2-one (Compound No. 38 of Table 1)

According to the same procedure as in Example 10, using 2-iodomethylthiophene instead of methyl iodide, the above-described compound (yield 42.4%) was obtained as a light yellow oil.

¹H-NMR (400 MHz, CDCl₃) δ1.61 (2H, m), 1.78–1.97 (6H, m), 2.06–2.23 (2H, m), 3.30 (1H, m), 3.42 (1H, m), 3.84 (3H, s), 4.72 (1H, d, J=15.14 Hz), 4.77 (1H, m), 4.78 (1H, d, J=15.14 Hz), 5.21 (1H, dd, J=9.76, 2.93 Hz), 6.82–6.87 (3H, m), 6.97 (1H, dd, J=4.89, 3.42 Hz), 7.04 (1H, d, J=3.42 Hz), 7.26 (1H, d, J=4.89 Hz)

Example 39

Synthesis of 6-(3-cyclopentyloxy-4-methoxyphenyl)-6-(2-pyridyl)-3,4,5,6-tetrahydro-2H-1,3-oxazin-2-one (Compound No. 39 of Table 1)

(1) Synthesis of 3-cyclopentyloxy-4-methoxyphenyl 2-pyridyl ketone

According to the same procedure as in Example 31(2), using 2-bromopyridine instead of 2-bromothiazole, 3-cyclopentyloxy-4-methoxyphenyl 2-pyridyl ketone(yield 99.0%) was obtained as a yellow oil.

¹H-NMR (400 MHz, CDCl₃) δ1.58–1.66 (2H, m), 1.80–2.02 (6H, m), 3.92 (3H, s), 4.86 (1H, m), 6.90 (1H, d, J=8.79 Hz), 7.47 (1H, ddd, J=7.81, 4.88, 0.98 Hz), 7.72 (1H, d, J=1.96 Hz), 7.72 (1H, dd, J=8.79, 1.96 Hz), 7.89 (1H, ddd, J=7.81, 7.81, 1.95 Hz), 7.98 (1H, d, J=7.81 Hz), 8.71 (1H, d, J=4.88 Hz)

(2) Synthesis of 3-(3-cyclopentyloxy-4-methoxyphenyl)-3-hydroxy-3-(2-pyridyl) propiononitrile According to the same procedure as in Example 1(1), using 3-cyclopentyloxy-4-methoxyphenyl 3-pyridyl ketone instead of 3,4-dimethoxybenzaldehyde, 3-(3-cyclopentyloxy-4-methoxyphenyl)-3-hydroxy-3-(2-pyridyl) propiononitrile was obtained as a yellow oil.

¹H-NMR (400 MHz, CDCl₃) δ1.56–1.58 (2H, m), 1.79–1.89 (6H, m), 3.26 (1H, d, J=16.60 Hz), 3.34 (1H, d, J=16.60 Hz), 3.82 (3H, s), 4.73 (1H, m), 5.69 (1H, s), 6.82 (1H, d, J=8.31 Hz), 6.95 (1H, dd, J=8.31, 1.95 Hz), 7.00 (1H, d, J=1.95 Hz), 7.25–7.29 (2H, m), 7.35 (1H, d, J=8.30 Hz), 7.72 (1H, ddd, J=7.82, 7.82, 1.95 Hz), 8.59 (1H, d, J=4.89 Hz)

(3) Synthesis of 6-(3-cyclopentyloxy-4-methoxyphenyl)-6-(2-pyridyl)-3,4,5,6-tetrahydro-2H-1,3-oxazin-2-one According to the same procedure as in Example 1(2) to (3), using 3-(3-cyclopentyloxy-4-methoxyphenyl)-3-hydroxy-3-(2-pyridyl)propiononitrile instead of 3-(3,4-dimethoxyphenyl)-3-hydroxypropiononitrile, the above-described compound (yield 11.6%) was obtained as a brown solid.

¹H-NMR (400 MHz, CDCl₃) δ1.57–1.59 (2H, m), 1.78–1.94 (6H, m), 2.63 (1H, ddd, J=14.16, 6.84, 6.84 Hz), 2.93 (1H, ddd, J=14.16, 5.86, 5.86 Hz), 3.21–3.24 (2H, m), 3.79 (3H, s), 4.75 (1H, m), 6.20 (1H, broad), 6.79 (1H, d, J=8.78 Hz), 7.04 (1H, dd, J=8.78, 2.45 Hz), 7.07 (1H, d, J=2.45 Hz), 7.18 (1H, ddd, J=5.37, 5.37, 2.44 Hz), 7.65–7.70 (2H, m), 8.56 (1H, d, J=5.37 Hz)

Example 40

Synthesis of 6-[3-(2-indanyloxy)-4-methoxyphenyl]-6-methyl-3,4,5,6-tetrahydro-2H-1,3-oxazin-2-one (Compound No. 40 of Table 1)

(1) Synthesis of 3-(2-indanyloxy)-4-methoxyacetophenone

According to the same procedure as in Example 6(1), using the 3-(2-indanyloxy)-4-methoxybenzaldehyde produced in Example 24(1) instead of 3-cyclopentyloxy-4-methoxybenzaldehyde, 3-(2-indanyloxy)-4-methoxyacetophenone (yield 75.7%) was obtained as a yellow solid.

¹H-NMR (400 MHz, CDCl₃) δ2.57 (3H, s), 3.24 (2H, dd, J=16.60, 3.42 Hz), 3.44 (1H, dd, J=16.60, 6.83 Hz), 3.88 (3H, s), 5.27 (1H, m), 6.89 (1H, d, J=8.79 Hz), 7.17–7.20 (2H, m), 7.22–7.25 (2H, m), 7.59 (1H, dd, J=8.79, 1.95 Hz), 7.60 (1H, d, J=1.95 Hz)

(2) Synthesis of 3-hydroxy-3-[3-(2-indanyloxy)-4-methoxyphenyl]butyronitrile

According to the same procedure as in Example 1(1), using 3-(2-indanyloxy)-4-methoxyacetophenone instead of 3,4-dimethoxybenzaldehyde, 3-hydroxy-3-[3-(2-indanyloxy)-4-methoxyphenyl]butyronitrile was obtained as a yellow oil.

¹H-NMR (400 MHz, CDCl₃) δ1.76 (3H, s), 2.26 (1H, broad s), 2.78 (1H, d, J=16.60 Hz), 2.83 (1H, d, J=16.60 Hz), 3.24 (2H, dd, J=16.60, 3.91 Hz), 3.38 (2H, dd, J=16.60, 6.34 Hz), 3.82 (3H, s), 5.23 (1H, m), 6.87 (1H, d, J=8.30 Hz), 7.01 (1H, dd, J=8.30, 2.44 Hz), 7.12 (1H, d, J=2.44 Hz), 7.14–7.25 (4H, m)

(3) Synthesis of 6-[3-(2-indanyloxy)-4-methoxyphenyl]-6-methyl-3,4,5,6-tetrahydro-2H-1,3-oxazin-2-one According to the same procedure as in Example 1(2) to (3), using 3-hydroxy-3-[3-(2-indanyloxy)-4-methoxyphenyl]butyronitrile instead of 3-(3,4-dimethoxyphenyl)-3-hydroxypropiononitrile, the above-described compound (yield 45.6%) was obtained as a light brown solid.

¹H-NMR (400 MHz, CDCl₃) δ1.67 (3H, s), 2.12 (1H, ddd, J=14.16, 10.74, 5.37 Hz), 2.29 (1H, ddd, J=14.16, 4.88, 4.88 Hz), 3.05 (1H, ddd, J=10.74, 10.74, 4.88 Hz), 3.21 (2H, ddd, J=16.60, 6.84, 3.91 Hz), 3.22–3.30 (1H, m), 3.37 (2H, ddd, J=16.60, 6.34, 1.95 Hz), 3.81 (3H, s), 5.21 (1H, m), 5.55 (1H, broad s), 6.86 (1H, d, J=8.30 Hz), 6.91 (1H, dd, J=8.30, 1.95 Hz), 6.96 (1H, d, J=1.95 Hz), 7.15–7.23 (4H, m)

Example 41

Synthesis of 6-[4-methoxy-3-(5-phenylpentyloxy) phenyl]-3,4,5,6-tetrahydro-2H-1,3-oxazin-2-one (Compound No. 41 of Table 1)

(1) Synthesis of 4-methoxy-3-(5-phenylpentyloxy) benzaldehyde

According to the same procedure as in Example 4(1), using 5-phenylpentanol instead of cyclopropylcarbinol, 4-methoxy-3-(5-phenylpentyloxy)benzaldehyde (yield 81.4%) was obtained as a light yellow solid.

¹H-NMR (400 MHz, CDCl₃) δ1.47–1.59 (2H, m), 1.67–1.75 (2H, m), 1.87–1.94 (2H, m), 2.65 (2H, t, J=7.81 Hz), 3.94 (3H, s), 4.07 (2H, t, J=6.83 Hz), 6.96–7.56 (8H, m), 9.84 (1H, s)

(2) Synthesis of 3-hydroxy-3-[4-methoxy-3-(5-phenylpentyloxy)phenyl)]propiononitrile According to the same procedure as in Example 1(1), using 4-methoxy-3-(5-phenylpentyloxy)benzaldehyde instead of 3,4-dimethoxybenzaldehyde, 3-hydroxy-3-[4-methoxy-3-(5-phenylpentyloxy)phenyl)]propiononitrile was obtained as a yellow oil.

¹H-NMR (400 MHz, CDCl₃) δ1.50–1.53 (2H, m), 1.68–1.72 (2H, m), 1.83–1.90 (2H, m), 2.64 (2H, t, J=7.32 Hz), 2.70 (1H, dd, J=16.60, 6.35 Hz), 2.72 (1H, dd, J=16.60, 6.35 Hz), 3.85 (3H, s), 4.01 (2H, t, J=6.35 Hz), 4.96 (1H, t, J=6.35 Hz), 6.85 (1H, d, J=8.30 Hz), 6.90 (1H, dd, J=8.30, 1.96 Hz), 6.93 (1H, d, J=1.96 Hz), 7.18–7.30 (5H, m)

(3) Synthesis of 6-[4-methoxy-3-(5-phenylpentyloxy)phenyl]-3,4,5,6-tetrahydro-2H-1,3-oxazin-2-one According to the same procedure as in Example 1(2) to (3), using 3-hydroxy-3-[4-methoxy-3-(5-phenylpentyloxy)phenyl)]propiononitrile instead of 3-(3,4-dimethoxyphenyl)-3-hydroxypropiononitrile, the above-described compound (yield 44.1%) was obtained as a light yellow solid.

¹H-NMR (400 MHz, CDCl₃) δ1.48–1.58 (2H, m), 1.67–1.74 (2H, m), 1.85–1.92 (2H, m), 2.06–2.13 (1H, m), 2.17–2.19 (1H, m), 2.65 (2H, t, J=7.33 Hz), 3.37–3.42 (1H, m), 3.44–3.51 (1H, m), 3.90 (3H, s), 4.01 (2H, t, J=6.84 Hz), 5.26 (1H, dd, J=9.77, 2.44 Hz), 5.60 (1H, broad s), 6.84–6.91 (3H, m), 7.16–7.30 (5H, m)

Example 42

Synthesis of 6-[4-methoxy-3-(5-phenylpentyloxy)phenyl]-3-methyl-3,4,5,6-tetrahydro-2H-1,3-oxazin-2-one (Compound No. 42 of Table 1)

According to the same procedure as in Example 8, using the 6-[4-methoxy-3-(5-phenylpentyloxy)phenyl]-3,4,5,6-tetrahydro-2H-1,3-oxazin-2-one produced in Example 41 instead of 6-(3,4-dimethoxyphenyl)-3,4,5,6-tetrahydro-2H-1,3-oxazin-2-one, the above-described compound (yield 75.9%) was obtained as a brown oil.

¹H-NMR (400 MHz, CDCl₃) δ1.49–1.56 (2H, m), 1.66–1.74 (2H, m), 1.84–1.92 (2H, m), 2.14–2.21 (2H, m), 2.64 (2H, t, J=7.81 Hz), 3.04 (3H, s), 3.25 (1H, ddd, J=11.72, 5.37, 3.42 Hz), 3.44–3.51 (1H, m), 3.85 (3H, s), 4.01 (2H, t, J=6.83 Hz), 5.21 (1H, dd, J=9.76, 3.42 Hz), 6.83–6.90 (3H, m), 7.16–7.29 (5H, m)

Example 43

Synthesis of 3,6-dimethyl-6-[3-(2-indanyloxy)-4-methoxyphenyl]-3,4,5,6-tetrahydro-2H-1,3-oxazin-2-one (Compound No. 43 of Table 1)

According to the same procedure as in Example 8, using the 6-[3-(2-indanyloxy)-4-methoxyphenyl]-6-methyl-3,4,5,6-tetrahydro-2H-1,3-oxazin-2-one produced in Example 40 instead of 6-(3,4-dimethoxyphenyl)-3,4,5,6-tetrahydro-2H-1,3-oxazin-2-one, the above-described compound (yield 98.7%) was obtained as a yellow oil.

¹H-NMR (400 MHz, CDCl₃) δ1.64 (3H, s), 2.20 (1H, ddd, J=13.67, 10.74, 5.86 Hz), 2.33 (1H, ddd, J=13.67, 4.88, 3.41 Hz), 2.93 (3H, s), 3.02 (1H, ddd, J=11.72, 10.74, 4.88 Hz), 3.14 (1H, ddd, J=11.72, 5.86, 3.41 Hz), 3.23 (2H, dd, J=16.60, 3.91 Hz), 3.38 (2H, ddd, J=16.60, 6.35, 6.35 Hz), 3.81 (3H, s), 5.21 (1H, m), 6.86 (1H, d, J=8.30 Hz), 6.89 (1H, dd, J=8.30, 1.95 Hz), 6.94 (1H, d, J=1.95 Hz), 7.16–7.20 (2H, m), 7.22–7.23 (2H, m)

Example 44

Synthesis of 6-(4-methoxy-3-phenethyloxyphenyl)-3-methyl-3,4,5,6-tetrahydro-2H-1,3-oxazin-2-one (Compound No. 44 of Table 1)

According to the same procedure as in Example 8, using the 6-(4-methoxy-3-phenethyloxyphenyl)-3,4,5,6-tetrahydro-2H-1,3-oxazin-2-one produced in Example 23 instead of 6-(3,4-dimethoxyphenyl)-3,4,5,6-tetrahydro-2H-1,3-oxazin-2-one, the above-described compound (yield 91.0%) was obtained as a yellow solid.

¹H-NMR (400 MHz, CDCl₃) δ2.11–2.18 (2H, m), 3.03 (3H, s), 3.16 (2H, t, J=7.81 Hz), 3.24 (1H, ddd, J=11.72, 5.37, 3.41 Hz), 3.46 (1H, ddd, J=11.72, 10.74, 5.86 Hz), 3.86 (3H, s), 4.21 (2H, ddd, J=7.81, 7.81, 2.93 Hz), 5.18 (1H, dd, J=9.77, 3.41 Hz), 6.84–6.90 (3H, m), 7.22–7.34 (5H, m)

Example 45

Synthesis of 6-[4-methoxy-3-(5-phenylpentyloxy)phenyl]-6-methyl-3,4,5,6-tetrahydro-2H-1,3-oxazin-2-one (Compound No. 45 of Table 1)

(1) Synthesis of 4-methoxy-3-(5-phenylpentyloxy)acetophenone

According to the same procedure as in Example 6(1), using the 4-methoxy-3-(5-phenylpentyloxy)benzaldehyde produced in Example 41(1) instead of 3-cyclopentyloxy-4-methoxybenzaldehyde, 4-methoxy-3-(5-phenylpentyloxy)acetophenone (yield 97.3%) was obtained as a yellow oil.

¹H-NMR (400 MHz, CDCl₃) δ1.50–1.57 (2H, m), 1.67–1.73 (2H, m), 1.86–1.92 (2H, m), 2.56 (3H, s), 2.65 (2H, t, J=7.82 Hz), 3.92 (3H, s), 4.07 (2H, t, J=6.83 Hz), 6.88 (1H, d, J=8.30 Hz), 7.16–7.30 (5H, m), 7.51 (1H, d, J=1.96 Hz), 7.56 (1H, dd, J=8.30, 1.96 Hz)

(2) Synthesis of 3-hydroxy-3-[4-methoxy-3-(5-phenylpentyloxy)phenyl)]butyronitrile According to the same procedure as in Example 1(1), using 4-methoxy-3-(5-phenylpentyloxy)acetophenone instead of 3,4-dimethoxybenzaldehyde, 3-hydroxy-3-[4-methoxy-3-(5-phenylpentyloxy)phenyl)]butyronitrile was obtained as a yellow oil.

¹H-NMR (400 MHz, CDCl₃) δ1.50–1.59 (2H, m), 1.69–1.75 (2H, m), 1.75 (3H, s), 1.85–1.91 (2H, m), 2.20 (1H, broad s), 2.65 (2H, t, J=7.81 Hz), 2.76 (1H, d, J=16.60 Hz), 2.82 (1H, d, J=16.60 Hz), 3.86 (3H, s), 4.02 (2H, t, J=6.83 Hz), 6.85 (1H, d, J=8.30 Hz), 6.96 (1H, dd, J=8.30, 1.95 Hz), 7.05 (1H, d, J=1.95 Hz), 7.16–7.30 (5H, m)

(3) Synthesis of 6-[4-methoxy-3-(5-phenylpentyloxy)phenyl]-6-methyl-3,4,5,6-tetrahydro-2H-1,3-oxazin-2-one According to the same procedure as in Example 1(2) to (3), using 3-hydroxy-3-[4-methoxy-3-(5-phenylpentyloxy)phenyl)]butyronitrile instead of 3-(3,4-dimethoxyphenyl)-3-hydroxypropiononitrile, the above-described compound (yield 52.9%) was obtained as a yellow oil.

¹H-NMR (400 MHz, CDCl₃) δ1.47–1.55 (2H, m), 1.65 (3H, s), 1.68–1.73 (2H, m), 1.85–1.91 (2H, m), 2.12 (1H, ddd, J=14.16, 10.25, 5.37 Hz), 2.29 (1H, ddd, J=14.16, 4.40, 4.40 Hz), 2.64 (2H, t, J=7.32 Hz), 3.05 (1H, ddd, J=11.23, 10.25, 4.40 Hz), 3.25 (1H, ddd, J=11.23, 5.37, 4.40 Hz), 3.85 (3H, s), 5.31 (1H, broad s), 6.85 (2H, s), 6.90 (1H, s), 7.15–7.29 (5H, m)

Example 46

Synthesis of 6-(4-methoxy-3-phenethyloxyphenyl)-6-methyl-3,4,5,6-tetrahydro-2H-1,3-oxazin-2-one (Compound No. 46 of Table 1)

(1) Synthesis of 4-methoxy-3-phenethyloxyacetophenone

According to the same procedure as in Example 6(1), using the 4-methoxy-3-phenethyloxybenzaldehyde produced in Example 23(1) instead of 3-cyclopentyloxy-4-methoxybenzaldehyde, 4-methoxy-3-phenethyloxyacetophenone(yield 89.3%) was obtained as a yellow oil.

$^1$H-NMR (400 MHz, CDCl$_3$) δ2.55 (3H, s), 3.18 (2H, t, J=7.32 Hz), 3.94 (3H, s), 4.27 (2H, t, J=7.32 Hz), 6.90 (1H, d, J=8.30 Hz), 7.25–7.33 (5H, m), 7.51 (1H, d, J=1.95 Hz), 7.58 (1H, dd, J=8.30, 1.95 Hz)

(2) Synthesis of 3-hydroxy-3-(4-methoxy-3-phenethyloxyphenyl)butyronitrile

According to the same procedure as in Example 1(1), using 4-methoxy-3-phenethyloxyacetophenone instead of 3,4-dimethoxybenzaldehyde, 3-hydroxy-3-(4-methoxy-3-phenethyloxyphenyl)butyronitrile was obtained as a yellow oil.

$^1$H-NMR (400 MHz, CDCl$_3$) δ1.72 (3H, s), 2.74 (1H, d, J=16.60 Hz), 2.78 (1H, d, J=16.60 Hz), 3.17 (2H, t, J=7.32 Hz), 3.87 (3H, s), 4.24 (2H, t, J=7.32 Hz), 6.86 (1H, d, J=8.30 Hz), 6.97 (1H, dd, J=8.30,1.95 Hz), 7.00 (1H, d, J=1.95 Hz), 7.22–7.35 (5H, m)

(3) Synthesis of 6-(4-methoxy-3-phenethyloxyphenyl)-6-methyl-3,4,5,6-tetrahydro-2H-1,3-oxazin-2-one According to the same procedure as in Example 1(2) to (3), using 3-hydroxy-3-(4-methoxy-3 -phenethyloxyphenyl)butyronitrile instead of 3-(3,4-dimethoxyphenyl)-3-hydroxypropiononitrile, the above-described compound (yield 74.6%) was obtained as a light yellow solid.

$^1$H-NMR (400 MHz, CDCl$_3$) δ1.63 (3H, s), 2.09 (1H, ddd, J=14.16, 11.24, 5.37 Hz), 2.24 (1H, ddd, J=14.16, 4.40, 3.90 Hz), 3.01 (1H, ddd, J=11.24, 11.24, 4.40 Hz), 3.15 (2H, t, J=7.32 Hz), 3.20–3.25 (1H, m), 3.86 (3H, s), 4.21 (2H, m), 5.66 (1H, broad s), 6.82–6.89 (3H, m), 7.21–7.34 (5H, m)

Example 47

Synthesis of 3,6-dimethyl-6-[4-methoxy-3-(5-phenylpentyloxy)phenyl]-3,4,5,6-tetrahydro-2H-1,3-oxazin-2-one (Compound No. 47 of Table 1)

According to the same procedure as in Example 8, using the 6-[4-methoxy-3-(5-phenylpentyloxy)phenyl]-6-methyl-3,4,5,6-tetrahydro-2H-1,3-oxazin-2-one produced in Example 45 instead of 6-(3,4-dimethoxyphenyl)-3,4,5,6-tetrahydro-2H-1,3-oxazin-2-one, the above-described compound (yield 86.0%) was obtained as a yellow oil.

$^1$H-NMR (400 MHz, CDCl$_3$) δ1.47–1.57 (2H, m), 1.61 (3H, s), 1.65–1.73 (2H, m), 1.83–1.90 (2H, m), 2.18 (1H, ddd, J=13.67, 10.74, 5.86 Hz), 2.33 (1H, ddd, J=13.67, 4.88, 3.42 Hz), 2.66 (2H, t, J=7.32 Hz), 2.90 (3H, s), 3.01 (1H, ddd, J=11.72, 10.74, 4.88 Hz), 3.12 (1H, ddd, J=11.72, 5.86, 3.42 Hz), 3.85 (3H, s), 4.00 (2H, t, J=6.83 Hz), 6.81–6.88 (3H, m), 7.15–7.29 (5H, m)

Example 48

Synthesis of 3.6-dimethyl-6-(4-methoxy-3-phenethyloxyphenyl)-3,4,5,6-tetrahydro-2H-1,3-oxazin-2-one (Compound No. 48 of Table 1)

According to the same procedure as in Example 8, using the 6-(4-methoxy-3-phenethyloxyphenyl)-6-methyl-3,4,5,6-tetrahydro-2H-1,3-oxazin-2-one produced in Example 46 instead of 6-(3,4-dimethoxyphenyl)-3,4,5,6-tetrahydro-2H-1,3-oxazin-2-one, the above-described compound (yield 71.0%) was obtained as a brown oil.

$^1$H-NMR (400 MHz, CDCl$_3$) δ1.60 (3H, s), 2.17 (1H, ddd, J=14.16, 11.23, 5.86 Hz), 2.30 (1H, ddd, J=14.16, 4.88, 3.91 Hz), 2.89 (3H, s), 2.99 (1H, ddd, J=11.23, 11.23, 4.88 Hz), 3.10 (1H, ddd, J=11.23, 5.86, 3.91 Hz), 3.15 (2H, t, J=7.32 Hz), 3.86 (3H, s), 4.21 (2H, m), 6.85–6.86 (3H, m), 7.21–7.34 (5H, m)

Example 49

Synthesis of 6-(3-cyclopropylmethyloxy-4-methoxyphenyl)-3-methyl-3,4 5,6-tetrahydro-2H-1,3-oxazin-2-one (Compound No. 49 of Table 1)

According to the same procedure as in Example 8, using the 6-(3-cyclopropylmethyloxy-4-methoxyphenyl)-3,4,5,6-tetrahydro-2H-1,3-oxazin-2-one produced in Example 4 instead of 6-(3,4-dimethoxyphenyl)-3,4,5,6-tetrahydro-2H-1,3-oxazin-2-one, the above-described compound (yield 73.7%) was obtained as a light yellow solid.

$^1$H-NMR (400 MHz, CDCl$_3$) δ0.33–0.37 (2H, m), 0.62–0.67 (2H, m), 1.30–1.37 (1H, m), 2.12–2.24 (2H, m), 3.04 (3H, s), 3.26 (1H, ddd, J=11.72, 5.86, 3.42 Hz), 3.48 (1H, ddd, J=11.72, 10.26, 5.86 Hz), 3.85 (2H, d, J=6.83 Hz), 3.88 (3H, s), 5.21 (1H, dd, J=9.77, 3.42 Hz), 6.85 (1H, d, J=8.30 Hz), 6.86 (1H, dd, J=8.30, 1.47 Hz), 6.91 (1H, d, J=1.47 Hz)

Example 50

Synthesis of 6-(3-cyclopropylmethyloxy-4-methoxyphenyl)-6-methyl-3,4,5,6-tetrahydro-2H-1,3-oxazin-2-one (Compound No. 50 of Table 1)

(1) Synthesis of 3-cyclopropylmethyloxy-4-methoxyacetophenone

According to the same procedure as in Example 6(1), using the 3-cyclopropylmethyloxy-4-methoxybenzaldehyde produced in Example 4(1) instead of 3-cyclopentyloxy-4-methoxybenzaldehyde, 3-cyclopropylmethyloxy-4-methoxyacetophenone (yield 92.9%) was obtained as a yellow solid.

$^1$H-NMR (400 MHz, CDCl$_3$) δ0.35–0. 39 (2H, m) , 0.64–0.68 (2H, m), 1.32–1.39 (1H, m), 2.56 (3H, s), 3.91 (2H, d, J=6.83 Hz), 3.95 (3H, s), 6.89 (1H, d, J=8.79 Hz), 7.51 (1H, d, J=1.95 Hz), 7.57 (1H, dd, J=8.79,1.95 Hz)

(2) Synthesis of 3-( 3-cyclopropylmethyloxy-4-methoxyphenyl) -3-hydroxybutyronitrile According to the same procedure as in Example Example 1(1), using 3-cyclopropylmethyloxy-4-methoxyacetophenone instead of 3,4-dimethoxybenzaldehyde, 3- (3-cyclopropylmethyloxy-4-methoxyphenyl) -3-hydroxybutyronitrile was obtained as a yellow oil.

$^1$H-NMR (400 MHz, CDCl$_3$) δ0.34–0.38 (2H, m) , 0.63–0.67 (2H, m), 1.30–1.38 (1H, m), 1.76 (3H, s), 2.77 (1H, d, J=16.61 Hz), 2.83 (1H, d, J=16.61 Hz), 3.88 (3H, s), 3.88 (2H, d, J=6.83 Hz), 6.86 (1H, d, J=8.30 Hz), 6.97 (1H, dd, J=8.30,2.44 Hz), 7.06 (1H, d, J=2.44 Hz)

(3) Synthesis of 6- (3-cyclopropylmethyloxy-4-methoxyphenyl) -6-methyl-3,4,5,6-tetrahydro-2H-1,3-oxazin-2-one According to the same procedure as in Example 1(2) to (3), using 3- (3-cyclopropylmethyloxy-4-methoxyphenyl)-3-hydroxybutyronitrile instead of 3-(3,4-dimethoxyphenyl)

-3-hydroxypropiononitrile, the above-described compound (yield 58.8%) was obtained as a colorless solid.

$^1$H-NMR (400 MHz, CDCl$_3$) δ0.33–0.37 (2H, m), 0.61–0.66 (2H, m), 1.29–1.34 (1H, m), 1.66 (3H, s), 2.13 (1H, ddd, J=13.67,10.75, 5.37 Hz), 2.30 (1H, ddd, J=13.67, 4.88, 4.88 Hz), 3.06 (1H, ddd, J=10.75, 10.75, 4.88 Hz), 3.23–3.28 (1H, m), 3.84–3.86 (2H, m), 3.87 (3H, s), 5.30 (1H, broad), 6.86–6.91 (3H, m)

Example 51

Synthesis of 6- (3-cyclopropylmethyloxy-4-methoxyphenyl)-3,6-dimethyl-3,4,5,6-tetrahydro-2H-1,3-oxazin-2-one (Compound No. 51 of Table 1)

According to the same procedure as in Example 8, using the 6-(3-cyclopropylmethyloxy-4-methoxyphenyl)-6-methyl-3,4,5,6-tetrahydro-2H-1,3-oxazin-2-one produced in Example 50 instead of 6-(3,4-dimethoxyphenyl)-3,4,5,6-tetrahydro-2H-1,3-oxazin-2-one, the above-described compound (yield 94.7%) was obtained as a light brown oil.

$^1$H-NMR (400 MHz, CDCl$_3$) δ0.33–0.37 (2H, m), 0.61–0.66 (2H, m), 1.28–1.35 (1H, m), 1.61 (3H, s), 2.19 (1H, ddd, J=13.68, 11.72, 5.86 Hz), 2.34 (1H, ddd, J=13.68, 4.88, 3.42 Hz), 2.90 (3H, s), 3.02 (1H, ddd, J=11.72, 11.72, 4.88 Hz), 3.12 (1H, ddd, J=11.72, 5.86, 3.42 Hz), 3.85 (2H, d, J=6.83 Hz), 3.87 (3H, s), 6.85–6.90 (3H, m)

Example 52

Synthesis of 6-(3-butoxy-4-methoxyphenyl)-6-methyl-3,4,5,6-tetrahydro-2H-1,3-oxazin-2-one (Compound No. 52 of Table 1)

(1) Synthesis of 3-butoxy-4-methoxyacetophenone

According to the same procedure as in Example 6(1), using 3-butoxy-4-methoxybenzaldehyde instead of 3-cyclopentyloxy-4-methoxybenzaldehyde, 3-butoxy-4-methoxyacetophenone (yield 97.3%) was obtained as a yellow oil.

$^1$H-NMR (400 MHz, CDCl$_3$) δ0.99 (3H, t, J=7.32 Hz), 1.48–1.58 (2H, m), 1.81–1.88 (2H, m), 2.56 (3H, s), 3.93 (3H, s), 4.08 (2H, t, J=6.84 Hz), 6.88 (1H, d, J=8.30 Hz), 7.52 (1H, d, J=1.96 Hz), 7.56 (1H, dd, J=8.30, 1.96 Hz)

(2) Synthesis of 3-(3-butoxy-4-methoxyphenyl)-3-hydroxybutyronitrile

According to the same procedure as in Example 1(1), using 3-butoxy-4-methoxyacetophenone instead of 3,4-dimethoxybenzaldehyde, 3-(3-butoxy-4-methoxyphenyl)-3-hydroxybutyronitrile was obtained as a yellow oil.

$^1$H-NMR (400 MHz, CDCl$_3$) δ0.99 (3H, t, J=6.83 Hz), 1.51 (2H, m), 1.76 (3H, s), 1.84 (2H, m), 2.77 (1H, d, J=16.60 Hz), 2.83 (1H, d, J=16.60 Hz), 3.86 (3H, s), 4.04 (2H, t, J=6.83 Hz), 6.85 (1H, d, J=8.30 Hz), 6.97 (1H, dd, J=8.30,2.44 Hz), 7.07 (1H, d, J=2.44 Hz)

(3) Synthesis of 6-(3-butoxy-4-methoxyphenyl)-6-methyl-3,4,5,6-tetrahydro-2H-1,3-oxazin-2-one According to the same procedure as in Example 1(2) to (3), using 3-(3-butoxy-4-methoxyphenyl)-3-hydroxybutyronitrile instead of 3-(3,4-dimethoxyphenyl)-3-hydroxypropiononitrile, the above-described compound (yield 32.6%) was obtained as a brown solid.

$^1$H-NMR (400 MHz, CDCl$_3$) δ0.97 (3H, t, J=7.32 Hz), 1.49 (2H, m), 1.66 (3H, s), 1.82 (2H, m), 2.13 (1H, ddd, J=13.67, 10.25, 5.38 Hz), 2.31 (1H, ddd, J=13.67, 4.40, 4.40 Hz), 3.06 (1H, ddd, J=11.23, 10.25, 4.40 Hz), 3.23–3.30 (1H, m), 3.86 (3H, s), 4.02 (2H, t, J=6.84 Hz), 5.15 (1H, broad s), 6.85–6.91 (3H, m)

Example 53

Synthesis of 6-(3-butoxy-4-methoxyphenyl)-3-methyl-3,4,5,6-tetrahydro-2H-1,3-oxazin-2-one (Compound No. 53 of Table 1)

According to the same procedure as in Example 8, using the 6-(3-butoxy-4-methoxyphenyl)-3,4,5,6-tetrahydro-2H-1,3-oxazin-2-one produced in Example 3 instead of 6-(3,4-dimethoxyphenyl)-3,4,5,6-tetrahydro-2H-1,3-oxazin-2-one, the above-described compound (yield 81.7%) was obtained as a light yellow solid.

$^1$H-NMR (400 MHz, CDCl$_3$) δ0.98 (3H, t, J=7.32 Hz), 1.45–1.54 (2H, m), 1.79–1.85 (2H, m), 2.13–2.24 (2H, m), 3.04 (3H, s), 3.26 (1H, ddd, J=11.23, 5.85, 3.42 Hz), 3.48 (1H, m), 3.86 (3H, s), 4.02 (2H, t, J=6.83 Hz), 5.21 (1H, dd, J=9.76, 3,41 Hz), 6.83–6.91 (3H, m)

Example 54

Synthesis of 6-(3-butoxy-4-methoxyphenyl)-3,6-dimethyl-3,4,5,6-tetrahydro-2H-1,3-oxazin-2-one (Compound No. 54 of Table 1)

According to the same procedure as in Example 8, using the 6-(3-butoxy-4-methoxyphenyl)-6-methyl-3,4,5,6-tetrahydro-2H-1,3-oxazin-2-one produced in Example 52 instead of 6-(3,4-dimethoxyphenyl)-3,4,5,6-tetrahydro-2H-1,3-oxazin-2-one, the above-described compound (yield 92.1%) was obtained as a light yellow oil.

$^1$H-NMR (400 MHz, CDCl$_3$) δ0.97 (3H, t, J=7.33 Hz), 1.45–1.54 (2H, m), 1.62 (3H, s), 1.78–1.85 (2H, m), 2.19 (1H, ddd, J=13.67,11.72, 5.86 Hz), 2.34 (1H, ddd, J=13.67, 4.88, 3.42 Hz), 2.90 (3H, s), 3.02 (1H, ddd, J=11.72, 11.72, 4.88 Hz), 3.12 (1H, ddd, J=11.72, 5.86, 3.42 Hz), 3.86 (3H, s), 4.02 (2H, t, J=6.83 Hz), 6.82 (1H, dd, J=8.30, 1.95 Hz), 6.85 (1H, d, J=8.30 Hz), 6.90 (1H, d, J=1.95 Hz)

Example 55

Synthesis of 6-[4-methoxy-3-[2-(2-pyridyl)ethoxy]phenyl]-3,4,5,6-tetrahydro-2H-1,3-oxazin-2-one (Compound No. 55 of Table 1)

(1) Synthesis of 4-methoxy-3-[2-(2-pyridyl)ethoxy]benzaldehyde

According to the same procedure as in Example 4(1), using 2-(2-pyridyl)ethanol instead of cyclopropylcarbinol, 4-methoxy-3-[2-(2-pyridyl)ethoxy]benzaldehyde (yield 83.7%) was obtained as a colorless solid.

$^1$H-NMR (400 MHz, CDCl$_3$) δ3.36 (2H, t, J=7.32 Hz), 3.94 (3H, s), 4.48 (2H, t, J=7.32 Hz), 6.97 (1H, d, J=7.81 Hz), 7.16 (1H, dd, J=7.32,4.88 Hz), 7.29 (1H, d, J=7.81 Hz), 7.45–7.47 (2H, m), 7.63 (1H, ddd, J=7.81,7.81,1.95 Hz), 8.56 (1H, d, J=4.88 Hz), 9.83 (1H, s)

(2) Synthesis of 3-hydroxy-3-[4-methoxy-3-[2-(2-pyridyl)ethoxy]phenyl]propiononitrile According to the same procedure as in Example 1(1), using 4-methoxy-3-[2-(2-pyridyl)ethoxy]benzaldehyde instead of 3,4-dimethoxybenzaldehyde, 3-hydroxy-3-[4-methoxy-3-[2-(2-pyridyl)ethoxy]phenyl]propiononitrile was obtained as a brown oil.

¹H-NMR (400 MHz, CDCl₃) δ2.68–2.79 (2H, m), 3.14 (1H, broad s), 3.30 (2H, t, J=7.32 Hz), 3.83 (3H, s), 4.39 (2H, t, J=7.32 Hz), 4.96 (1H, t, J=6.35 Hz), 6.85 (1H, d, J=8.30 Hz), 6.93 (1H, dd, J=8.30, 1.95 Hz), 6.98 (1H, d, J=1.95 Hz), 7.15 (1H, dd, J=7.82, 4.88 Hz), 7.29 (1H, d, J=7.82 Hz), 7.63 (1H, ddd, J=7.82, 7.82, 1.96 Hz), 8.51 (1H, m)

(3) Synthesis of 6-[4-methoxy-3-[2-(2-pyridyl)ethoxy]phenyl]-3,4,5,6-tetrahydro-2H-1,3-oxazin-2-one According to the same procedure as in Example 1(2) to (3), using 3-hydroxy-3-[4-methoxy-3-[2-(2-pyridyl)ethoxy]phenyl]propiononitrile instead of 3-(3,4-dimethoxyphenyl)-3-hydroxypropiononitrile, the above-described compound (yield 25.9%) was obtained as a light yellow solid.

¹H-NMR (400 MHz, CDCl₃) δ2.04–2.17 (2H, m), 3.33 (2H, t, J=7.32 Hz), 3.39–3.69 (2H, m), 3.84 (3H, s), 4.42 (2H, t, J=7.32 Hz), 5.27 (1H, m), 6.86 (1H, d, J=8.31 Hz), 6.91–6.94 (2H, m), 7.15 (1H, m), 7.30 (1H, d, J=7.82 Hz), 7.62 (1H, t, J=7.82 Hz), 8.56 (1H, d, J=3.90 Hz)

Example 56

Synthesis of 6-[4-methoxy-3-[(1-phenylcyclopropyl)methyloxy]phenyl]-3,4,5,6-tetrahydro-2H-1,3-oxazin-2-one (Compound No. 56 of Table 1)

(1) Synthesis of 4-methoxy-3-[(1-phenylcyclopropyl)methyloxy]benzaldehyde

According to the same procedure as in Example 4(1), using 1-phenylcyclopropylmethanol instead of cyclopropylcarbinol, 4-methoxy-3-[(1-phenylcyclopropyl)methyloxy]benzaldehyde (yield 74.8%) was obtained as a yellow oil.

¹H-NMR (400 MHz, CDCl₃) δ1.00–1.02 (2H, m), 1.04–1.07 (2H, m), 3.90 (3H, s), 4.13 (2H, s), 6.93 (1H, d, J=7.81 Hz), 7.19–7.23 (1H, m), 7.28–7.31 (3H, m), 7.41–7.45 (3H, m), 9.79 (1H, s)

(2) Synthesis of 3-hydroxy-3-[4-methoxy-3-[(1-phenylcyclopropyl)methyloxy]phenyl]propiononitrile According to the same procedure as in Example 1(1), using 4-methoxy-3-[(1-phenylcyclopropyl)methyloxy]benzaldehyde instead of 3,4-dimethoxybenzaldehyde, 3-hydroxy-3-[4-methoxy-3-[(1-phenylcyclopropyl)methyloxy]phenyl]propiononitrile was obtained as a brown oil.

¹H-NMR (400 MHz, CDCl₃) δ0.97–1.00 (2H, m), 1.02–1.05 (2H, m), 2.38 (1H, broad s), 2.61 (1H, dd, J=16.60, 5.86 Hz), 2.66 (1H, dd, J=16.60, 5.86 Hz), 3.79 (3H, s), 4.09 (2H, s), 4.83 (1H, t, J=5.86 Hz), 6.73 (1H, d, J=1.96 Hz), 6.81 (1H, d, J=8.30 Hz), 6.84 (1H, dd, J=8.30, 1.96 Hz), 7.18–7.22 (1H, m), 7.25–7.31 (2H, m), 7.42–7.45 (2H, m)

(3) Synthesis of 6-[4-methoxy-3-[(1-phenylcyclopropyl)methyloxy]phenyl]-3,4,5 6-tetrahydro-2H-1,3-oxazin-2-one According to the same procedure as in Example 1(2) to (3), using 3-hydroxy-3-[4-methoxy-3-[(1-phenylcyclopropyl)methyloxy]phenyl]propiononitrile instead of 3-(3,4-dimethoxyphenyl)-3-hydroxypropiononitrile, the above-described compound (yield 55.5%) was obtained as a light yellow solid.

¹H-NMR (400 MHz, CDCl₃) δ0.97–1.00 (2H, m), 1.03–1.06 (2H, m), 1.98–2.05 (1H, m), 2.08–2.14 (1H, m), 3.33–3.37 (1H, m), 3.40–3,47 (1H, m), 3.80 (3H, s), 4.10 (2H, s), 5.19 (1H, dd, J=10.24, 2.93 Hz), 5.65 (1H, broad s), 6.79 (1H, d, J=1.95 Hz), 6.83 (1H, d, J=8.30 Hz), 6.86 (1H, dd, J=8.30, 1.95 Hz), 7.18–7.21 (1H, m), 7.27–7.31 (2H, m), 7.43–7.45 (2H, m)

Example 57

Synthesis of 6-[4-methoxy-3-[(1-phenylcyclopropyl)methyloxy]phenyl]-3-methyl-3,4,5,6-tetrahydro-2H-1,3-oxazin-2-one (Compound No. 57 of Table 1)

According to the same procedure as in Example 8, using the 6-[4-methoxy-3-[(1-phenylcyclopropyl)methyloxy]phenyl]-3,4,5,6-tetrahydro-2H-1,3-oxazin-2-one produced in Example 56 instead of 6-(3,4-dimethoxyphenyl)-3,4,5,6-tetrahydro-2H-1,3-oxazin-2-one, the above-described compound (yield 91.2%) was obtained as a brown oil.

¹H-NMR (400 MHz, CDCl₃) δ0.97–1.00 (2H, m), 1.03–1.06 (2H, m), 2.06–2.14 (2H, m), 3.03 (3H, s), 3.22 (1H, ddd, J=11.72,5.37,2.93 Hz), 3.44 (1H, ddd, J=11.72, 10.74,5.85 Hz), 3.79 (3H, s), 4.09 (2H, s), 5.14 (2H, dd, J=9.77,2.93 Hz), 6.78 (1H, d, J=1.96 Hz), 6.81 (1H, d, J=8.30 Hz), 6.85 (1H, dd, J=8.30,1.96 Hz), 7.18–7.22 (1H, m), 7.27–7.31 (2H, m), 7.42–7.45 (2H, m)

Example 58

Synthesis of 6-[3-(10,11-dihydro-5H-dibenzo[a,d]cyclohepten-5-yloxy)-4-methoxyphenyl]-3,4,5,6-tetrahydro-2H-1,3-oxazin-2-one (Compound No. 58 of Table 1)

(1) Synthesis of 3-(10,11-dihydro-5H-dibenzo[a,d]cyclohepten-5-yloxy)-4-methoxybenzaldehyde According to the same procedure as in Example 4(1), using dibenzosuberol instead of cyclopropylcarbinol, 3-(10,11-dihydro-5H-dibenzo[a,d]cyclohepten-5-yloxy)-4-methoxybenzaldehyde (yield 51.9%) was obtained as a light yellow solid.

¹H-NMR (400 MHz, CDCl₃) δ3.15–3.21 (2H, m), 3.55–3.62 (2H, m), 3.96 (3H, s), 6.37 (1H, s), 6.98 (1H, d, J=8.31 Hz), 7.11–7.22 (6H, m), 7.34 (1H, d, J=1.95 Hz), 7.43–7.47 (3H, m), 9.74 (1H, s)

(2) Synthesis of 3-[3-(10,11-dihydro-5H-dibenzo[a,d]cyclophenten-5-yloxy)-4-methoxyphenyl]-3-hydroxypropiononitrile According to the same procedure as in Example 1(1), using 3-(10,11-dihydro-5H-dibenzo[a,d]cyclohepten-5-yloxy)-4-methoxybenzaldehyde instead of 3,4-dimethoxybenzaldehyde, 3-[3-(10,11-dihydro-5H-dibenzo[a,d]cyclophenten-5-yloxy)-4-methoxyphenyl]-3-hydroxypropiononitrile was obtained as a yellow oil.

¹H-NMR (400 MHz, CDCl₃) δ2.09 (1H, d, J=2.93 Hz), 2.49 (1H, dd, J=16.60,5.86 Hz), 2.56 (1H, dd, J=16.60,6.83 Hz), 3.10–3.16 (2H, m), 3.60–3.66 (2H, m),3.89 (3H, s), 4.81 (1H, m), 6.17 (1H, s), 6.71 (1H, d, J=1.95 Hz), 6.88 (1H, d, J=8.30 Hz), 6.94 (1H, dd, J=8.30,1.95 Hz), 7.11–7.22 (6H, m), 7.38 (2H, dd, J=7.32,3,41 Hz)

(3) Synthesis of 6-[3-(10,11-dihydro-5H-dibenzo[a,d]cyclophenten-5-yloxy)-4-methoxyphenyl]-3,4,5,6-tetrahydro-2H-1,3-oxazin-2-one According to the same procedure as in Example 1(2) to (3), using 3-[3-(10,11-dihydro-5H-dibenzo[a,d]

cyclohepten-5-yloxy)-4-methoxyphenyl]-3-hydroxypropiononitrile instead of 3-(3,4-dimethoxyphenyl)-3-hydroxypropiononitrile, the above-described compound (yield 22.6%) was obtained as a yellow solid.

$^1$H-NMR (400 MHz, CDCl$_3$) δ1.73–1.88 (1H, m), 1.89–1.95 (1H, m), 3.05–3.14 (3H, m), 3.24 (1H, ddd, J=11.23,11.23,4.89 Hz), 3.57–3.68 (2H, m), 3.84 (3H, s), 5.08 (1H, dd, J=9.76,2.93 Hz), 6.19 (1H, s), 6.62 (1H, broad s), 6.69 (1H, d, J=1.96 Hz), 6.84 (1H, d, J=8.30 Hz), 6.90 (1H, dd, J=8.30,1.96 Hz), 7.08–7.19 (6H, m), 7.38 (2H, d, J=7.32 Hz)

Example 59

Synthesis of 6-[3-(10,11-dihydro-5H-dibenzo[a,d] cyclohepten-5-yloxy)-4-methoxyphenyl]-3-methyl-3,4,5,6-tetrahydro-2H-1,3-oxazin-2-one (Compound No. 59 of Table 1)

According to the same procedure as in Example 8, using the 6-[3-(10,11-dihydro-5H-dibenzo[a,d]cyclohepten-5-yloxy)-4-methoxyphenyl]-3,4,5,6-tetrahydro-2H-1,3-oxazin-2-one produced in Example 58 instead of 6-(3,4-dimethoxyphenyl)-3,4,5,6-tetrahydro-2H-1,3-oxazin-2-one, the above-described compound (yield 77.0%) was obtained as a light yellow solid.

$^1$H-NMR (400 MHz, CDCl$_3$) δ1.89–1.97 (1H, m), 1.99–2.05 (1H, m), 2.98 (3H, s), 3.08–3.18 (3H, m), 3.34 (1H, ddd, J=11.23,9.77,5.37 Hz), 3.57–3.68 (2H, m), 3.88 (3H, s), 5.08 (1H, dd, J=9.28,2.45 Hz), 6.19 (1H, s), 6.68 (1H, d, J=1.95 Hz), 6.87 (1H, d, J=8.30 Hz), 6.92 (1H, dd, J=8.30,1.95 Hz), 7.10–7.22 (6H, m), 7.39 (2H, d, J=7.32 Hz)

Example 60

Synthesis of 6-[3-[3-(4-benzyl-1-piperazinyl) propoxy]-4-methoxyphenyl]-3,4,5,6-tetrahydro-2H-1,3-oxazin-2-one (Compound No. 60 of Table 1)

(1) Synthesis of 3-[3-(4-benzyl-1-piperazinyl) propoxy]-4-methoxybenzaldehyde

According to the same procedure as in Example 4(1), using 3-(4-benzyl-1-piperazinyl)propanol instead of cyclopropylcarbinol, 3-[3-(4-benzyl-1-piperazinyl) propoxy]-4-methoxybenzaldehyde (yield 52.2%) was obtained as a brown oil.

$^1$H-NMR (400 MHz, CDCl$_3$) δ2.04 (2H, m), 2.46–2.55 (8H, m), 2.53 (2H, t, J=7.32 Hz), 3.52 (2H, s), 3.94 (3H, s), 4.14 (2H, t, J=6.35 Hz), 6.97 (1H, d, J=8.30 Hz), 7.28–7.33 (5H, m), 7.42 (1H, d, J=1.46 Hz), 7.55–7.57 (1H, m), 9.84 (1H, s)

(2) Synthesis of 3-[3-[3-(4-benzyl-1-piperazinyl) propoxy]-4-methoxyphenyl]-3-hydroxypropiononitrile According to the same procedure as in Example 1(1), using 3-[3-(4-benzyl-1-piperazinyl)propoxy]-4-methoxybenzaldehyde instead of 3,4-dimethoxybenzaldehyde, 3-[3-[3-(4-benzyl-1-piperazinyl) propoxy]-4-methoxyphenyl]-3-hydroxypropiononitrile was obtained as a yellow oil.

$^1$H-NMR (400 MHz, CDCl$_3$) δ2.02 (2H, m), 2.45–2.54 (8H, m), 2.52 (2H, t, J=6.84 Hz), 2.74–2.77 (2H, m), 3.51 (2H, s), 3.85 (3H, s), 4.07 (2H, t, J=6.83 Hz), 4.97 (1H, m), 6.86 (1H, d, J=8.30 Hz), 6.91 (1H, dd, J=8.30,1.95 Hz), 6.97 (1H, d, J=1.95 Hz), 7.30–7.32 (5H, m)

(3) Synthesis of 6-[3-[3-(4-benzyl-1-piperazinyl) propoxy]-4-methoxyphenyl]-3,4,5,6-tetrahydro-2H-1,3-oxazin-2-one According to the same procedure as in Example 1(2) to (3), using 3-[3-[3-(4-benzyl-1-piperazinyl)propoxy]-4-methoxyphenyl]-3-hydroxypropiononitrile instead of 3-(3,4-dimethoxyphenyl)-3-hydroxypropiononitrile, the above-described compound (yield 14.8%) was obtained as a yellow oil.

$^1$H-NMR (400 MHz, CDCl$_3$) δ2.03 (2H, m), 2.04–2.12 (1H, m), 2.15–2.19 (1H, m), 2.35–2.56 (8H, m), 2.54 (2H, t, J=6.83 Hz), 3.36–3.49 (2H, m), 3.51 (2H, s), 3.85 (3H, S), 4.07 (2H, t, J=6.35 Hz), 5.24 (1H, dd, J=9.77,2.44 Hz), 6.26 (1H, broad s), 6.85 (1H, d, J=8.30 Hz), 6.89 (1H, dd, J=8.30,1.95 Hz), 6.92 (1H, d, J=1.95 Hz), 7.23–7.32 (5H, m)

Example 61

Synthesis of 6-(3-cyclobutylmethyloxy-4-methoxyphenyl)-3,4,5,6-tetrahydro-2H-1,3-oxazin-2-one (Compound No. 61 of Table 1)

(1) Synthesis of 3-cyclobutylmethyloxy-4-methoxybenzaldehyde

According to the same procedure as in Example 4(1), using cyclobutylmethanol instead of cyclopropylcarbinol, 3-cyclobutylmethyloxy-4-methoxybenzaldehyde (yield 77.1%) was obtained as a light yellow oil.

$^1$H-NMR (400 MHz, CDCl$_3$) δ1.84–2.01 (4H, m), 2.14–2.22 (2H, m), 2.86 (1H, m), 3.94 (3H, s), 4.06 (2H, d, J=6.83 Hz), 6.97 (1H, d, J=8.30 Hz), 7.41 (1H, d, J=1.95 Hz), 7.44 (1H, dd, J=8.30,1.95 Hz), 9.85 (1H, s)

(2) Synthesis of 3-(3-cyclobutylmethyloxy-4-methoxyphenyl)-3-hydroxypropiononitrile According to the same procedure as in Example 1(1), using 3-cyclobutylmethyloxy-4-methoxybenzaldehyde instead of 3,4-dimethoxybenzaldehyde, 3-(3-cyclobutylmethyloxy-4-methoxyphenyl)-3-hydroxypropiononitrile was obtained as a brown oil.

$^1$H-NMR (400 MHz, CDCl$_3$) δ1.06 (1H, d, J=6.35 Hz), 1.82–2.00 (4H, m), 2.13–2.20 (2H, m), 2.73 (1H, dd, J=16.60,6.35 Hz), 2.78 (1H, dd, J=16.60,6.35 Hz), 2.84 (1H, m,J=6.84 Hz), 3.85 (3H, s), 4.01 (2H, d, J=6.84 Hz), 4.98 (1H, t, J=6.35 Hz), 6.86 (1H, d, J=8.30 Hz), 6.91 (1H, dd, J=8.30,1.96 Hz), 6.95 (1H, d, J=1.96 Hz)

(3) Synthesis of 6-(3-cyclobutylmethyloxy-4-methoxyphenyl)-3,4,5,6-tetrahydro-2H-1,3-oxazin-2-one According to the same procedure as in Example 1(2) to (3), using 3-(3-cyclobutylmethyloxy-4-methoxyphenyl)-3-hydroxypropiononitrile instead of 3-(3,4-dimethoxyphenyl)-3-hydroxypropiononitrile, the above-described compound (yield 55.7%) was obtained as a light yellow solid.

$^1$H-NMR (400 MHz, CDCl$_3$) δ1.83–1.98 (4H, m), 2.08–2.22 (4H, m), 2.83 (1H, m), 3,40 (1H, ddd, J=11.23, 5.86,3.42 Hz), 3,49 (1H, ddd, J=11.23,11.23,5.37 Hz), 3.86 (3H, s), 4.01 (2H, d, J=6.84 Hz), 5.26 (1H, broad s), 5.27 (1H, dd, J=9.77,2.93 Hz), 6.85 (1H, d, J=8.30 Hz), 6.88 (1H, dd, J=8.30,1.95 Hz), 6.93 (1H, d, J=1.95 Hz)

Example 62

Synthesis of 6-(3-cyclobutylmethyloxy-4-methoxyphenyl)-3-methyl-3,4,5,6-tetrahydro-2H-1, 3-oxazin-2-one (Compound No. 62 of Table 1)

According to the same procedure as in Example 8, using the 6-(3-cyclobutylmethyloxy-4-methoxyphenyl)-3,4,5,6- tetrahydro-2H-1,3-oxazin-2-one produced in Example 61 instead of 6-(3,4-dimethoxyphenyl)-3,4,5,6-tetrahydro-2H-1,3-oxazin-2-one, the above-described compound (yield 67.4%) was obtained as a light yellow solid.

$^1$H-NMR (400 MHz, CDCl$_3$) δ1.80–2.00 (4H, m), 2.11–2.24 (4H, m), 2.83 (1H, m), 3.04 (3H, s), 3.26 (1H, ddd, J=11.23,4.88,3,41 Hz), 3.48 (1H, ddd, J=11.23,10.26, 5.86 Hz), 3.85 (3H, s), 4.00 (2H, d, J=6.83 Hz), 5.21 (1H, dd, J=9.28,2.93 Hz), 6.84 (1H, d, J=8.30 Hz), 6.85–6.92 (2H, m)

Example 63

Synthesis of 6-[4-methoxy-3-[(1-methylcyclopropyl)methyloxy]phenyl]-3,4,5,6-tetrahydro-2H-1,3-oxazin-2-one (Compound No. 63 of Table 1)

(1) Synthesis of 4-methoxy-3-[(1-methylcyclopropyl)methyloxy]benzaldehyde

According to the same procedure as in Example 4(1), using 1-methylcyclopropylcarbinol instead of cyclopropylcarbinol, 4-methoxy-3-[(1-methylcyclopropyl) methyloxy]benzaldehyde (yield 65.0%) was obtained as a yellow oil.

$^1$H-NMR (400 MHz, CDCl$_3$) δ0.45–0.47 (2H, m), 0.56–0.57 (2H, m), 1.27 (3H, s), 3.84 (2H, s), 3.95 (3H, s), 6.97 (1H, d, J=8.30 Hz), 7.37 (1H, broad), 7.45 (1H, dd, J=8.30,1.46 Hz), 9.83 (1H, s)

(2) Synthesis of 3-[4-methoxy-3-[(1-methylcyclopropyl)methyloxy]phenyl]-3-hydroxypropiononitrile According to the same procedure as in Example 1(1), using 4-methoxy-3-[(1-methylcyclopropyl)methyloxy] benzaldehyde instead of 3,4-dimethoxybenzaldehyde, 3-[4-methoxy-3-[(1-methylcyclopropyl)methyloxy]phenyl]-3-hydroxypropiononitrile was obtained as a yellow oil.

$^1$H-NMR (400 MHz, CDCl$_3$) δ0.43–0.45 (2H, m), 0.54–0.57 (2H, m), 1.26 (3H, s), 1.61 (1H, broad s), 2.72 (1H, dd, J=16.60,6.35 Hz), 2.77 (1H, dd, J=16.60,6.35 Hz), 3.79 (2H, s), 3.86 (3H, s), 4.97 (1H, t, J=6.35 Hz), 6.85–6.93 (3H, m)

(3) Synthesis of 6-[4-methoxy-3-[(1-methylcyclopropyl)methyloxy]phenyl]-3,4,5,6-tetrahydro-2H-1,3-oxazin-2-one According to the same procedure as in Example 1(2) to (3), using 3-[4-methoxy-3-[(1-methylcyclopropyl) methyloxy]phenyl]-3-hydroxypropiononitrile instead of 3-(3,4-dimethoxyphenyl)-3-hydroxypropiononitrile, the above-described compound (yield 37.5%) was obtained as a colorless solid.

$^1$H-NMR (400 MHz, CDCl$_3$) δ0.42–0.45 (2H, m), 0.54–0.56 (2H, m), 1.26 (3H, s), 2.05–2.12 (1H, m), 2.15–2.20 (1H, m), 3.39 (1H, ddd, J=11.23,5.86,3.42 Hz), 3,47 (1H, ddd, J=11.23,10.74,4.88 Hz), 3.79 (2H, s), 3.87 (3H, s), 5.25 (1H, dd, J=10.26,2.93 Hz), 5.94 (1H, broad s), 6.85–6.90 (3H, m)

Example 64

Synthesis of 6-[4-methoxy-3-[(1-methylcyclopropyl)methyloxy]phenyl]-3-methyl-3,4,5,6-tetrahydro-2H-1,3-oxazin-2-one (Compound No. 64 of Table 1)

According to the same procedure as in Example 8, using the 6-[4-methoxy-3-[(1-methylcyclopropyl)methyloxy] phenyl]-3,4,5,6-tetrahydro-2H-1,3-oxazin-2-one produced in Example 63 instead of 6-(3,4-dimethoxyphenyl)-3,4,5,6-tetrahydro-2H-1,3-oxazin-2-one, the above-described compound (yield 87.9%) was obtained as a light yellow solid.

$^1$H-NMR (400 MHz, CDCl$_3$) δ0.42–0.44 (2H, m), 0.53–0.56 (2H, m), 1.26 (3H, s), 2.13–2.21 (2H, m), 3.04 (3H, s), 3.26 (1H, ddd, J=11.72,5.38,3.42 Hz), 3.48 (1H, ddd, J=11.72,10.74,5.86 Hz), 3.78 (2H, s), 3.86 (3H, s), 5.20 (1H, dd, J=9.77,3.42 Hz), 6.83–6.90 (3H, m)

Example 65

Synthesis of 6-[4-methoxy-3-(2-methylpropoxy) phenyl]-3,4,5,6-tetrahydro-2H-1,3-oxazin-2 -one (Compound No. 65 of Table 1)

(1) Synthesis of 4-methoxy-3-(2-methylpropoxy) benzaldehyde

According to the same procedure as in Example 4(1), using isobutanol instead of cyclopropylcarbinol, 4-methoxy-3-(2-methylpropoxy)benzaldehyde (yield 75.8%) was obtained as a yellow oil.

$^1$H-NMR (400 MHz, CDCl$_3$) δ1.05 (6H, d, J=6.83 Hz), 2.19 (1H, m, J=6.83 Hz), 3.83 (2H, d, J=6.83 Hz), 3.95 (3H, s), 6.97 (1H, d, J=7.81 Hz), 7.40 (1H, d, J=1.46 Hz), 7.44 (1H, dd, J=7.81,1.46 Hz), 9.84 (1H, s)

(2) Synthesis of 3-hydroxy-3-[4-methoxy-3-(2-methylpropoxy)phenyl]propiononitrile According to the same procedure as in Example 1(1), using 4-methoxy-3-(2-methylpropoxy)benzaldehyde instead of 3,4-dimethoxybenzaldehyde, 3-hydroxy-3-[4-methoxy-3-(2-methylpropoxy)phenyl]propiononitrile was obtained as a yellow oil.

$^1$H-NMR (400 MHz, CDCl$_3$) δ1.04 (6H, d, J=6.84 Hz), 2.17 (1H, m,J=6.84 Hz), 2.73 (1H, dd, J=16.60,6.35 Hz), 2.79 (1H, dd, J=16.60,6.35 Hz), 3.78 (2H, d, J=6.84 Hz), 3.86 (3H, s), 4.98 (1H, t, J=6.35 Hz), 6.86 (1H, d, J=8.30 Hz), 6.91 (1H, dd, J=8.30,1.95 Hz), 6.94 (1H, d, J=1.95 Hz)

(3) Synthesis of 6-[4-methoxy-3-(2-methylpropoxy) phenyl]-3,4,5,6-tetrahydro-2H-1,3-oxazin-2-one According to the same procedure as in Example 1(2) to (3), using 3-hydroxy-3-[4-methoxy-3-(2-methylpropoxy) phenyl]propiononitrile instead of 3-(3,4-dimethoxyphenyl)-3-hydroxypropiononitrile, the above-described compound (yield 65.7%) was obtained as a light yellow solid.

$^1$H-NMR (400 MHz, CDCl$_3$) δ1.04 (6H, d, J=6.84 Hz), 2.06–2.22 (3H, m), 3.37–3.52 (2H, m), 3.78 (2H, d, J=6.83 Hz), 3.87 (3H, s), 5.26 (1H, dd, J=10.25,2.93 Hz), 5.91 (1H, broad s), 6.85–6.91 (3H, m)

Example 66

Synthesis of 6-[4-methoxy-3-(2-methylpropoxy) phenyl]-3-methyl-3,4,5,6-tetrahydro-2H-1,3-oxazin-2-one (Compound No. 66 of Table 1)

According to the same procedure as in Example 8, using the 6-[4-methoxy-3-(2-methylpropoxy)phenyl]-3,4,5,6-tetrahydro-2H-1,3-oxazin-2-one of Example 65 instead of 6-(3,4-dimethoxyphenyl)-3,4,5,6-tetrahydro-2H-1,3-oxazin-2-one, the above-described compound (yield 93.6%) was obtained as a light yellow solid.

$^1$H-NMR (400 MHz, CDCl$_3$) δ1.03 (6H, d, J=6.34 Hz), 2.13–2.21 (3H, m), 3.04 (3H, s), 3.26 (1H, ddd, J=11.72, 5.86,3.42 Hz), 3.48 (1H, ddd, J=11.72,10.25,6.34 Hz), 3.77 (2H, d, J=6.83 Hz), 3.86 (3H, s), 5.21 (1H, dd, J=9.76,3.90 Hz), 6.85–6.91 (2H, m), 7.36 (1H, s)

Example 67

Synthesis of 6-[4-methoxy-3-[2-(1-naphthyl)ethoxy] phenyl]-3,4,5,6-tetrahydro-2H-1,3-oxazin-2-one (Compound No. 67 of Table 1)

(1) Synthesis of 4-methoxy-3-[2-(1-naphthyl) ethoxy]benzaldehyde

According to the same procedure as in Example 4(1), using 2-(1-naphthyl)ethanol instead of cyclopropylcarbinol, 4-methoxy-3-[2-(1-naphthyl)ethoxy]benzaldehyde (yield 54.1%) was obtained as a colorless solid.

$^1$H-NMR (400 MHz, CDCl$_3$) δ3.67 (2H, t, J=7.81 Hz), 3.96 (3H, s), 4.41 (2H, t, J=7.81 Hz), 6.98 (1H, d, J=8.30 Hz), 7.37 (1H, d, J=1.47 Hz), 7.41–7.46 (2H, m), 7.48 (1H, dd, J=7.82,0.97 Hz), 7.51 (1H, dd, J=3.42,1.47 Hz), 7.55 (1H, dd, J=6.84,1.47 Hz), 7.77 (1H, dd, J=6.84,2.45 Hz), 7.87 (1H, dd, J=8.30,0.97 Hz), 8.11 (1H, d, J=8.30 Hz), 9.80 (1H, s)

(2) Synthesis of 3-hydroxy-3-[4-methoxy-3-[2-(1-naphthyl)ethoxy]phenyl]propiononitrile According to the same procedure as in Example 1(1), using 4-methoxy-3-[2-(1-naphthyl)ethoxy]benzaldehyde instead of 3,4-dimethoxybenzaldehyde, 3-hydroxy-3-[4-methoxy-3-[2-(1-naphthyl)ethoxy]phenyl]propiononitrile was obtained as a brown oil.

$^1$H-NMR (400 MHz, CDCl$_3$) δ2.23 (1H, broad s), 2.60–2.71 (2H, m),3.66 (2H, t, J=7.32 Hz),3.88 (3H, s), 4.36 (2H, t, J=7.32 Hz),4.88 (1H, t, J=6.35 Hz), 6.84 (1H, d, J=1.95 Hz), 6.86 (1H, d, J=8.30 Hz),6.90 (1H, dd, J=8.30, 1.95 Hz), 7.40–7.56 (4H, m),7.77 (1H, dd, J=7.33,1.96 Hz),7.88 (1H, dd, J=8.79,1.47 Hz),8.12 (1H, d, J=8.30 Hz)

(3) Synthesis of 6-[4-methoxy-3-[2-(1-naphthyl) ethoxy]phenyl]3,4,5,6-tetrahydro-2H-1,3-oxazin-2-one According to the same procedure as in Example 1(2) to (3), using 3-hydroxy-3-[4-methoxy-3-[2-(1-naphthyl) ethoxy]phenyl]propiononitrile instead of 3-(3,4-dimethoxyphenyl)-3-hydroxypropiononitrile, the above-described compound (yield 61.4%) was obtained as a light yellow solid.

$^1$-H-NMR (400 MHz, CDCl$_3$) δ1.93–2.03 (1H, m), 2.07–2.11 (1H, m), 3.32 (1H, ddd, J=11.23,5.86,3.42 Hz), 3.40 (1H, ddd, J=11.23,11.23,4.88 Hz), 3.66 (2H, t, J=7.81 Hz), 3.88 (3H, s), 4.34 (2H, t, J=7.81 Hz), 5.17 (1H, dd, J=10.26,2.44 Hz), 5.84 (1H, broad s), 6.84 (1H, d, J=1.47 Hz), 6.87 (1H, d, J=8.30 Hz), 6.89 (1H, dd, J=8.30,1.47 Hz), 7.38–7.56 (4H, m), 7.76 (1H, dd, J=7.32,1.95 Hz), 7.87 (1H, d, J=7.81 Hz), 8.11 (1H, d, J=8.30 Hz)

Example 68

Synthesis of 6-[4-methoxy-3-[2-(1-naphthyl)ethoxy] phenyl]-3-methyl-3,4,5,6-tetrahydro-2H-1,3-oxazin-2-one (Compound No. 68 of Table 1)

According to the same procedure as in Example 8, using the 6-[4-methoxy-3-[2-(1-naphthyl)ethoxy]phenyl]-3,4,5,6-tetrahydro-2H-1,3-oxazin-2-one produced in Example 67 instead of 6-(3,4-dimethoxyphenyl)-3,4,5,6-tetrahydro-2H-1,3-oxazin-2-one, the above-described compound (yield 77.8%) was obtained as a light yellow oil.

$^1$H-NMR (400 MHz, CDCl$_3$) δ2.01–2.15 (2H, m), 3.00 (3H, s), 3.20 (1H, ddd, J=11.72,5.86,2.93 Hz), 3.42 (1H, ddd, J=11.72,11.72,5.86 Hz), 3.66 (2H, t, J=7.32 Hz), 3.88 (3H, s), 4.35 (2H, m), 5.13 (1H, dd, J=9.77,3.42 Hz), 6.84–6.87 (2H, m), 6.89 (1H, dd, J=8.30,1.47 Hz), 7.41–7.74 (4H, m), 7.76 (1H, dd, J=7.33,1.95 Hz), 7.86 (1H, d, J=7.81 Hz), 8.10 (1H, d, J=8.30 Hz)

Example 69

Synthesis of 6-[3-(2-ethylbutoxy)-4-methoxyphenyl]-3,4,5,6-tetrahydro-2H-1,3-oxazin-2-one (Compound No. 69 of Table 1)

(1) Synthesis of 3-(2-ethylbutoxy)-4-methoxybenzaldehyde

According to the same procedure as in Example 4(1), using 2-ethylbutanol instead of cyclopropylcarbinol, 3-(2-ethylbutoxy)-4-methoxybenzaldehyde (yield 78.4%) was obtained as a colorless oil.

$^1$H-NMR (400 MHz, CDCl$_3$) δ0.94 (6H, t, J=7.32 Hz), 1.43–1.56 (4H, m), 1.80 (1H, m), 3.94 (3H, s), 3.94 (2H, d, J=6.35 Hz), 6.97 (1H, d, J=7.82 Hz), 7.41 (1H, d, J=1.95 Hz), 7.44 (1H, dd, J=7.82,1.95 Hz), 9.85 (1H, s)

(2) Synthesis of 3-[3-(2-ethylbutoxy)-4-methoxyphenyl]-3-hydroxypropiononitrile

According to the same procedure as in Example 1(1), using 3-(2-ethylbutoxy)-4-methoxybenzaldehyde instead of 3,4-dimethoxybenzaldehyde, 3-[3-(2-ethylbutoxy)-4-methoxyphenyl]-3-hydroxypropiononitrile was obtained as a yellow oil.

$^1$H-NMR (400 MHz, CDCl$_3$) δ0.94 (6H, t, J=7.33 Hz), 1.42–1.56 (4H, m), 1.77 (1H, m),2.74 (1H, dd, J=16.60,6.35 Hz), 2.79 (1H, dd, J=16.60,6.35 Hz), 3.85 (3H, s), 3.89 (2H, d, J=6.35 Hz), 4.98 (1H, t, J=6.35 Hz), 6.86 (1H, d, J=8.30 Hz), 6.91 (1H, dd, J=8.30,1.95 Hz), 6.95 (1H, d, J=1.95 Hz)

(3) Synthesis of 6-[3-(2-ethylbutoxy)-4-methoxyphenyl]-3,4,5,6-tetrahydro-2H-1,3-oxazin-2-one According to the same procedure as in Example 1(2) to (3), using 3-[3-(2-ethylbutoxy)-4-methoxyphenyl]-3-hydroxypropiononitrile instead of 3-(3,4-dimethoxyphenyl)-3-hydroxypropiononitrile, the above-described compound (yield 58.5%) was obtained as a light brown solid.

$^1$H-NMR (400 MHz, CDCl$_3$) δ0.94 (6H, t, J=7.32 Hz), 1.40–1.57 (4H, m), 1.77 (1H, m), 2.05–2.15 (1H, m), 2.17–2.21 (1H, m), 3,41 (1H, ddd, J=11.23, 5.86, 3.42 Hz), 3,49 (1H, ddd, J=11.23, 11.23, 5.37 Hz), 3.86 (3H, s), 3.89 (2H, d, J=5.86 Hz), 5.26 (1H, dd, J=10.26, 2.93 Hz), 5.70 (1H, broad s), 6.84–6.93 (3H, m)

Example 70

Synthesis of 6-[3-(2-ethylbutoxy)-4-methoxyphenyl]-3-methyl-3,4,5,6-tetrahydro-2H-1, 3-oxazin-2-one (Compound No. 70 of Table 1)

According to the same procedure as in Example 8, using the 6-[3-(2-ethylbutoxy)-4-methoxyphenyl]-3,4,5,6-tetrahydro-2H-1,3-oxazin-2-one produced in Example 69 instead of 6-(3,4-dimethoxyphenyl)-3,4,5,6-tetrahydro-2H-

1,3-oxazin-2-one, the above-described compound (yield 97.9%) was obtained as a light yellow solid.

$^1$H-NMR (400 MHz, CDCl$_3$) δ0.94 (6H, t, J=7.32 Hz), 1.42–1.55 (4H, m), 1.76 (1H, m,J=6.35 Hz), 2.15–2.23 (2H, m), 3.04 (3H, s), 3.26 (1H, ddd, J=11.72, 5.37, 3.42 Hz), 3.48 (1H, ddd, J=11.72, 10.26, 6.35 Hz), 3.85 (3H, s), 3.88 (2H, d, J=6.35 Hz), 5.21 (1H, dd, J=11.28, 3.42 Hz), 6.85–6.92 (3H, m)

Example 71

Synthesis of 3-ethyl-6-[3-(2-indanyloxy)-4-methoxyphenyl]-3,4,5,6-tetrahydro-2H-1,3-oxazin-2-one (Compound No. 71 of Table 1)

According to the same procedure as in Example 25, using ethyl iodide instead of methyl iodide, the above-described compound (yield 92.0%) was obtained as a light yellow solid.

$^1$H-NMR (400 MHz, CDCl$_3$) δ1.21 (3H, t, J=7.32 Hz), 2.13–2.26 (2H, m), 3.23–3.32 (1H, m), 3.23 (2H, dm, J=16.60 Hz), 3.38 (2H, dd, J=16.60, 6.35 Hz), 3.40–3,49 (1H, m), 3.43 (2H, q, J=7.32 Hz), 3.81 (3H, s), 5.18–5.23 (2H, m), 6.86 (1H, d, J=8.30 Hz), 6.92 (1H, d, J=8.30 Hz), 6.96 (1H, s), 7.16–7.23 (4H, m)

Example 72

Synthesis of 6-[4-methoxy-3-[2-(4-methyl-5-thiazolyl)ethoxy]phenyl]-3,4,5,6-tetrahydro-2H-1,3-oxazin-2-one (Compound No. 72 of Table 1)

(1) Synthesis of 4-methoxy-3-[2-(4-methyl-5-thiazolyl)ethoxy]benzaldehyde

According to the same procedure as in Example 4(1), using 2-(4-methyl-5-thiazolyl)ethanol instead of cyclopropylcarbinol, 4-methoxy-3-[2-(4-methyl-5-thiazolyl)ethoxy]benzaldehyde (yield 79.9%) was obtained as a colorless solid.

$^1$H-NMR (400 MHz, CDCl$_3$) δ2.46 (3H, s), 3.33 (2H, t, J=6.84 Hz), 3.96 (3H, s), 4.24 (2H, t, J=6.84 Hz), 6.99 (1H, d, J=8.30 Hz), 7.39 (1H, d, J=1.95 Hz), 7.48 (1H, dd, J=8.30, 1.95 Hz), 8.60 (1H, s), 9.84 (1H, s)

(2) Synthesis of 3-[4-methoxy-3-[2-(4-methyl-5-thiazolyl)ethoxy]phenyl]-3-hydroxypropiononitrile According to the same procedure as in Example 1(1), using 4-methoxy-3-[2-(4-methyl-5-thiazolyl)ethoxy] benzaldehyde instead of 3,4-dimethoxybenzaldehyde, 3-[4-methoxy-3-[2-(4-methyl-5-thiazolyl)ethoxy]phenyl]-3-hydroxypropiononitrile was obtained as a light yellow solid.

$^1$H-NMR (400 MHz, CDCl$_3$) δ2.44 (3H, s), 2.60 (1H, d, J=3.42 Hz), 2.74 (2H, m), 3.30 (2H, t, J=6.83 Hz), 3.87 (3H, s), 4.19 (2H, t, J=6.83 Hz), 4.97 (1H, m), 6.88 (1H, d, J=7.81 Hz), 6.93–6.95 (2H, m), 8.57 (1H, s)

(3) Synthesis of 6-[4-methoxy-3-[2-(4-methyl-5-thiazolyl)ethoxy]phenyl]-3,4,5,6-tetrahydro-2H-1,3-oxazin-2-one According to the same procedure as in Example 1(2) to (3), using 3-[4-methoxy-3-[2-(4-methyl-5-thiazolyl)ethoxy] phenyl]-3-hydroxypropiononitrile instead of 3-(3,4-dimethoxyphenyl)-3-hydroxypropiononitrile, the above-described compound (yield 27.3%) was obtained as a light yellow solid.

$^1$H-NMR (400 MHz, CDCl$_3$) δ2.07 (1H, dddd, J=14.16, 10.25, 10.25, 5.86 Hz), 2.17–2.21 (1H, m), 2.45 (3H, s), 3.31 (2H, t, J=6.84 Hz), 3.37–3.42 (1H, m), 3.48 (1H, ddd, J=11.27, 10.25, 4.88 Hz), 3.87 (3H, s), 4.19 (2H, ddd, J=6.84, 6.84, 1.95 Hz), 5.25 (1H, dd, J=10.25, 2.44 Hz), 5.40 (1H, broad s), 6.86–6.93 (3H, m), 8.60 (1H, s)

Example 73

Synthesis of 6-[4-methoxy-3-[2-(4-methyl-5-thiazolyl)ethoxy]phenyl]-3-methyl-3,4,5,6-tetrahydro-2H-1,3-oxazin-2-one (Compound No. 70 of Table 1)

According to the same procedure as in Example 8, using the 6-[4-methoxy-3-[2-(4-methyl-5-thiazolyl)ethoxy] phenyl]-3,4,5,6-tetrahydro-2H-1,3-oxazin-2-one produced in Example 72 instead of 6-(3,4-dimethoxyphenyl)-3,4,5,6-tetrahydro-2H-1,3-oxazin-2-one, the above-described compound (yield 54.8%) was obtained as a brown oil.

$^1$H-NMR (400 MHz, CDCl$_3$) δ2.08–2.22 (2H, m), 2.45 (3H, s), 3.03 (3H, s), 3.25 (1H, ddd, J=11.71, 5.37, 2.93 Hz), 3.30 (2H, t, J=6.84 Hz), 3.48 (1H, ddd, J=11.71, 11.23, 5.86 Hz), 3.87 (3H, s), 4.18 (2H, ddd, J=6.84, 6.84, 2.93 Hz), 5.20 (1H, dd, J=9.76, 2.93 Hz), 6.85–6.91 (3H, m), 8.60 (1H, s)

Example 74

Synthesis of 6-[3-[2-(4-fluorophenyl)ethoxy]-4-methoxyphenyl]-3,4,5,6-tetrahydro-2H-1,3-oxazin-2-one (Compound No. 74 of Table 1)

(1) Synthesis of 3-[2-(4-fluorophenyl)ethoxy]-4-methoxybenzaldehyde

According to the same procedure as in Example 4(1), using 4-fluorophenethyl alcohol instead of cyclopropylcarbinol, 3-[2-(4-fluorophenyl)ethoxy]-4-methoxybenzaldehyde (yield 91.6%) was obtained as a light yellow oil.

$^1$H-NMR (400 MHz, CDCl$_3$) δ3.15 (2H, t, J=7.32 Hz), 3.96 (3H, s), 4.25 (2H, t, J=7.32 Hz), 6.98 (1H, d, J=8.30 Hz), 6.98–7.03 (2H, m), 7.24–7.28 (2H, m), 7.39 (1H, d, J=1.47 Hz), 7.46 (1H, dd, J=8.30, 1.47 Hz), 9.83 (1H, s)

(2) Synthesis of 3-[3-[2-(4-fluorophenyl)ethoxy]-4-methoxyphenyl]-3-hydroxypropiononitrile According to the same procedure as in Example 1(1), using 3-[2-(4-fluorophenyl)ethoxy]-4-methoxybenzaldehyde instead of 3,4-dimethoxybenzaldehyde, 3-[3-[2-(4-fluorophenyl)ethoxy]-4-methoxyphenyl]-3-hydroxypropiononitrile was obtained as a brown oil.

$^1$H-NMR (400 MHz, CDCl$_3$) δ2.31 (1H, broad s), 2.71 (1H, dd, J=16.60, 6.35 Hz), 2.75 (1H, dd, J=16.60, 6.35 Hz), 3.13 (1H, d, J=7.33 Hz), 3.86 (3H, s), 4.20 (2H, t, J=7.33 Hz), 4.95 (1H, t, J=6.35 Hz), 6.87 (1H, d, J=8.79 Hz), 6.91–6.93 (2H, m), 6.98–7.02 (2H, m), 7.24–7.28 (2H, m)

(3) Synthesis of 6-[3-[2-(4-fluorophenyl)ethoxy]-4-methoxyphenyl]-3,4,5,6-tetrahydro-2H-1,3-oxazin-2-one According to the same procedure as in Example 1(2) to (3), using 3-[3-[2-(4-fluorophenyl)ethoxy]-4-methoxyphenyl]-3-hydroxypropiononitrile instead of 3-(3,4-dimethoxyphenyl)-3-hydroxypropiononitrile, the above-described compound (yield 48.0%) was obtained as a light brown solid.

$^1$H-NMR (400 MHz, CDCl$_3$) δ2.06 (1H, dddd, J=14.26, 10.25, 10.25, 5.86 Hz), 2.14–2.21 (1H, m), 3.13 (2H, t, J=7.33 Hz), 3.36–3,40 (1H, m), 3.44–3.82 (1H, m), 3.87 (3H, s), 4.19 (2H, ddd, J=7.33, 7.33, 2.44 Hz), 5.25 (1H, dd, J=9.77, 2.44 Hz), 5.25 (1H, broad s), 6.85–6.90 (3H, m), 7.00 (2H, m), 7.26 (2H, m)

Example 75

Synthesis of 6-[3-[2-(4-fluorophenyl)ethoxy]-4-methoxyphenyl]-3-methyl-3,4,5,6-tetrahydro-2H-1,3-oxazin-2-one (Compound No. 75 of Table 1)

According to the same procedure as in Example 8, using the 6-[3-[2-(4-fluorophenyl)ethoxy]-4-methoxyphenyl]-3,4,5,6-tetrahydro-2H-1,3-oxazin-2-one produced in Example 74 instead of 6-(3,4-dimethoxyphenyl)-3,4,5,6-tetrahydro-2H-1,3-oxazin-2-one, the above-described compound (yield 57.3%) was obtained as a brown oil.

$^1$H-NMR (400 MHz, CDCl$_3$) δ2.07–2.21 (2H, m), 3.03 (3H, s), 3.13 (2H, t, J=7.33 Hz), 3.24 (1H, ddd, J=11.72, 5.86, 2.93 Hz), 3,47 (1H, ddd, J=11.72, 11.72, 5.86 Hz), 3.86 (3H, s), 4.19 (2H, ddd, J=7.33, 7.33, 3.42 Hz), 5.19 (1H, dd, J=9.77, 3.42 Hz), 6.86–6.89 (3H, m), 6.98–7.02 (2H, m), 7.24–7.27 (2H, m)

Example 76

Synthesis of 6-(3-cyclopentylmethyloxy-4-methoxyphenyl)-3,4,5,6-tetrahydro-2H-1,3-oxazin-2-one (Compound No. 76 of Table 1)

(1) Synthesis of 3-cyclopentylmethyloxy-4-methoxybenzaldehyde

According to the same procedure as in Example 4(1), using cyclopentylcarbinol instead of cyclopropylcarbinol, 3-cyclopentylmethyloxy-4-methoxybenzaldehyde (yield 80.6%) was obtained as a yellow oil.

$^1$H-NMR (400 MHz, CDCl$_3$) δ1.36–1.42 (2H, m), 1.56–1.66 (4H, m), 1.83–1.92 (2H, m), 2.46 (1H, m), 3.94 (2H, d, J=7.32 Hz), 3.95 (3H, s), 6.97 (1H, d, J=7.81 Hz), 7.41 (1H, d, J=1.95 Hz), 7.44 (1H, dd, J=7.81, 1.95 Hz), 9.84 (1H, s)

(2) Synthesis of 3-(3-cyclopentylmethyloxy-4-methoxyphenyl)-3-hydroxypropiononitrile According to the same procedure as in Example 1(1), using 3-cyclopentylmethyloxy-4-methoxybenzaldehyde instead of 3,4-dimethoxybenzaldehyde, 3-(3-cyclopentylmethyloxy-4-methoxyphenyl)-3-hydroxypropiononitrile was obtained as a brown oil.

$^1$H-NMR (400 MHz, CDCl$_3$) δ1.36–1.42 (2H, m), 1.58–1.68 (4H, m), 1.83–1.91 (2H, m), 2.30 (1H, d, J=2.93 Hz), 2.44 (1H, m, J=7.33 Hz), 2.76 (2H, m), 3.86 (3H, s), 3.89 (2H, d, J=7.33 Hz), 4.98 (1H, m), 6.86 (1H, d, J=8.30 Hz), 6.90 (1H, dd, J=8.30, 1.95 Hz), 6.95 (1H, d, J=1.95 Hz)

(3) Synthesis of 6-(3-cyclopentylmethyloxy-4-methoxyphenyl)-3,4,5,6-tetrahydro-2H-1,3-oxazin-2-one According to the same procedure as in Example 1(2) to (3), using 3-(3-cyclopentylmethyloxy-4-methoxyphenyl)-3-hydroxypropiononitrile instead of 3-(3,4-dimethoxyphenyl)-3-hydroxypropiononitrile, the above-described compound (yield 22.6%) was obtained as a colorless solid.

$^1$H-NMR (400 MHz, CDCl$_3$) δ1.34–1.39 (2H, m), 1.59–1.65 (4H, m), 1.82–1.90 (2H, m), 2.10 (1H, dddd, J=14.16, 10.25, 10.25, 5.37 Hz), 2.17–2.23 (1H, m), 2.44 (1H, m, J=7.32 Hz), 3.38–3.43 (1H, m), 3,49 (1H, ddd, J=10.74, 10.74, 4.88 Hz), 3.87 (3H, s), 3.88 (2H, d, J=7.32 Hz), 5.27 (1H, dd, J=10.25, 2.93 Hz), 5.28 (1H, broad s), 6.84–6.93 (3H, m)

Example 77

Synthesis of 6-(3-cyclopentylmethyloxy-4-methoxyphenyl)-3-methyl-3,4,5,6-tetrahydro-2H-1,3-oxazin-2-one (Compound No. 77 of Table 1)

According to the same procedure as in Example 8, using the 6-(3-cyclopentylmethyloxy-4-methoxyphenyl)-3,4,5,6-tetrahydro-2H-1,3-oxazin-2-one produced in Example 76 instead of 6-(3,4-dimethoxyphenyl)-3,4,5,6-tetrahydro-2H-1,3-oxazin-2-one, the above-described compound (yield 84.3%) was obtained as a colorless solid.

$^1$H-NMR (400 MHz, CDCl$_3$) δ1.35–1.39 (2H, m), 1.54–1.65 (4H, m), 2.13–2.22 (2H, m), 2.43 (1H, m), 3.04 (3H, s), 3.26 (1H, ddd, J=11.72, 5.37, 3.42 Hz), 3.48 (1H, ddd, J=11.72, 10.25, 5.37 Hz), 3.86 (3H, s), 3.88 (2H, d, J=6.83 Hz), 5.21 (1H, dd, J=9.28, 3.42 Hz), 6.83–6.88 (2H, m), 6.92 (1H, m)

Example 78

Synthesis of 6-[4-methoxy-3-(trans-4-phenylcyclohexyloxy)phenyl]-3,4,5,6-tetrahydro-2H-1,3-oxazin-2-one (Compound No. 78 of Table 1)

(1) Synthesis of 4-methoxy-3-(trans-4-phenylcyclohexyloxy)benzaldehyde

According to the same procedure as in Example 4(1), using cis-1-hydroxy-4-phenylcyclohexane instead of cyclopropylcarbinol, 4-methoxy-3-(trans-4-phenylcyclohexyloxy)benzaldehyde (yield 37.5%) was obtained as a colorless solid.

$^1$H-NMR (400 MHz, CDCl$_3$) δ1.59–1.76 (4H, m), 2.01–2.04 (2H, m), 2.30–2.33 (2H, m), 2.60 (1H, m), 3.96 (3H, s), 4.35–4.41 (1H, m), 7.00 (1H, d, J=7.81 Hz), 7.19–7.33 (5H, m), 7.46–7.48 (2H, m), 9.86 (1H, s)

(2) Synthesis of 3-hydroxy-3-[4-methoxy-3-(trans-4-phenylcyclohexyloxy)phenyl]propiononitrile According to the same procedure as in Example 1(1), using 4-methoxy-3-(trans-4-phenylcyclohexyloxy) benzaldehyde instead of 3,4-dimethoxybenzaldehyde, 3-hydroxy-3-[4-methoxy-3-(trans-4-phenylcyclohexyloxy) phenyl]propiononitrile was obtained as a brown oil.

$^1$H-NMR (400 MHz, CDCl$_3$) δ1.56–1.74 (4H, m), 1.99–2.05 (2H, m), 2.27–2.32 (2H, m), 2.58 (1H, m), 2.75 (1H, dd, J=16.60, 6.35 Hz), 2.79 (1H, dd, J=16.60, 6.35 Hz), 3.87 (3H, s), 4.24–4.29 (1H, m), 4.99 (1H, t, J=6.35 Hz), 6.89 (1H, d, J=8.30 Hz), 6.96 (1H, dd, J=8.30, 1.95 Hz), 7.04 (1H, d, J=1.95 Hz), 7.18–7.32 (5H, m)

(3) Synthesis of 6-[4-methoxy-3-(trans-4-phenylcyclohexyloxy)phenyl]-3,4,5,6-tetrahydro-2H-1,3-oxazin-2-one According to the same procedure as in Example 1(2) to (3), using 3-hydroxy-3-[4-methoxy-3-(trans-4-phenylcyclohexyloxy)phenyl]propiononitrile instead of 3-(3,4-dimethoxyphenyl)-3-hydroxypropiononitrile, the above-described compound (yield 59.6%) was obtained as a light brown solid.

$^1$H-NMR (400 MHz, CDCl$_3$) δ1.62–1.73 (4H, m), 1.98–2.01 (2H, m), 2.06–2.16 (1H, m), 2.19–2.22 (1H, m), 2.26–2.29 (2H, m), 2.58 (1H, m), 3.40 (1H, ddd, J=10.74, 5.86, 3.42 Hz), 3.50 (1H, ddd, J=10.74, 10.74, 5.37 Hz), 3.88 (3H, s), 4.27 (1H, m), 5.27 (1H, dd, J=9.47, 2.45 Hz), 5.28 (1H, broad s), 6.89 (1H, d, J=8.30 Hz), 6.94 (1H, dd, J=8.30, 1.95 Hz), 7.00 (1H, d, J=1.95 Hz), 7.18–7.32 (5H, m)

Example 79

Synthesis of 6-[4-methoxy-3-(trans-4-phenylcyclohexyloxy)phenyl]-3-methyl-3,4,5,6-tetrahydro-2H-1,3-oxazin-2-one (Compound No. 79 of Table 1)

According to the same procedure as in Example 8, using the 6-[4-methoxy-3-(trans-4-phenylcyclohexyloxy)phenyl]-3,4,5,6-tetrahydro-2H-1,3-oxazin-2-one produced in Example 79 instead of 6-(3,4-dimethoxyphenyl)-3,4,5,6-tetrahydro-2H-1,3-oxazin-2-one, the above-described compound (yield 82.4%) was obtained as a pale yellow solid.

$^1$H-NMR (400 MHz, CDCl$_3$) δ1.55–1.70 (4H, m), 1.98–2.01 (2H, m), 2.15–2.26 (4H, m), 2.54–2.60 (1H, m), 3.04 (3H, s), 3.27 (1H, ddd, J=11.72, 5.37, 3.42 Hz), 3.48 (1H, ddd, J=11.72, 10.25, 5.86 Hz), 3.87 (3H, s), 4.27 (1H, m), 5.22 (1H, dd, J=9.28, 3.91 Hz), 6.87 (1H, d, J=8.30 Hz), 6.92 (1H, dd, J=8.30, 1.96 Hz), 6.99 (1H, d, J=1.96 Hz), 7.18–7.32 (5H, m)

Example 80

Synthesis of 6-[4-methoxy-3-(1-methylcyclopentyloxy)phenyl]-3,4,5,6-tetrahydro-2H-1,3-oxazin-2-one (Compound No. 80 of Table 1)

(1) Synthesis of 4-methoxy-3-(1-methylcyclopentyloxy)benzaldehyde

According to the same procedure as in Example 4(1), using 1-methylcyclopentanol instead of cyclopropylcarbinol, 4-methoxy-3-(1-methylcyclopentyloxy)benzaldehyde (yield 4.7%) was obtained as a brown oil.

$^1$H-NMR (400 MHz, CDCl$_3$) δ1.49 (3H, s), 1.61–1.73 (2H, m), 1.79–1.91 (2H, m), 2.12–2.18 (2H, m), 3.91 (3H, s), 6.98 (1H, d, J=8.30 Hz), 7.51 (1H, dd, J=8.30, 1.96 Hz), 7.51 (1H, d, J=1.96 Hz), 9.84 (1H, s)

(2) Synthesis of 3-hydroxy-3-[4-methoxy-3-(1-methylcyclopentyloxy)phenyl]propiononitrile According to the same procedure as in Example 1(1), using 4-methoxy-3-(1-methylcyclopentyloxy)benzaldehyde instead of 3,4-dimethoxybenzaldehyde, 3-hydroxy-3-[4-methoxy-3-(1-methylcyclopentyloxy)phenyl]propiononitrile was obtained as a brown oil.

$^1$H-NMR (400 MHz, CDCl$_3$) δ1.43 (3H, s), 1.59–1.73 (4H, m), 1.80–1.90 (2H, m), 2.03–2.15 (2H, m), 2.52 (1H, broad s), 2.71 (1H, dd, J=16.60, 6.35 Hz), 2.76 (1H, dd, J=16.60, 6.35 Hz), 3.81 (3H, s), 4.94 (1H, t, J=6.35 Hz), 6.86 (1H, d, J=8.30 Hz), 7.00 (1H, dd, J=8.30, 1.96 Hz), 7.02 (1H, d, J=1.96 Hz)

(3) Synthesis of 6-[4-methoxy-3-(1-methylcyclopentyloxy)phenyl]-3,4,5,6-tetrahydro-2H-1,3-oxazin-2-one According to the same procedure as in Example 1(2) to (3), using 3-hydroxy-3-[4-methoxy-3-(1-methylcyclopentyloxy)phenyl]propiononitrile instead of 3-(3,4-dimethoxyphenyl)-3-hydroxypropiononitrile, the above-described compound (yield 13.2%) was obtained as a colorless solid.

$^1$H-NMR (400 MHz, CDCl$_3$) δ1.42 (3H, s), 1.59–1.69 (4H, m), 1.85–1.89 (2H, m), 2.08–2.13 (4H, m), 3.39 (1H, ddd, J=11.23, 5.37, 3.42 Hz), 3.44–3.51 (1H, m), 3.82 (3H, s), 5.25 (1H, dd, J=9.77, 2.93 Hz), 5.28 (1H, broad, s), 6.88 (1H, d, J=8.79 Hz), 6.99–7.02 (2H, m)

Example 81

Synthesis of 6-[4-methoxy-3-(2-methylpropoxyphenyl]-6-methyl-3,4,5,6-tetrahydro-2H-1,3-oxazin-2-one (Compound No. 81 of Table 1)

(1) Synthesis of 4-methoxy-3-(2-methylpropoxy)acetophenone

According to the same procedure as in Example 6(1), using the 4-methoxy-3-(2-methylpropoxy)benzaldehyde produced in Example 65(1) instead of 3-cyclopentyloxy-4-methoxybenzaldehyde, 4-methoxy-3-(2-methylpropoxy)acetophenone (yield 90.8%) was obtained as a yellow brown solid.

$^1$H-NMR (400 MHz, CDCl$_3$) δ1.06 (6H, d, J=6.84 Hz), 2.18 (1H, m), 2.56 (3H, s), 3.82 (2H, d, J=6.84 Hz), 3.93 (3H, s), 6.88 (1H, d, J=8.30 Hz), 7.51 (1H, d, J=1.96 Hz), 7.56 (1H, d, J=8.30, 1.96 Hz)

(2) Synthesis of 3-[4-methoxy-3-(2-methylpropoxy)phenyl]-3-hydroxybutyronitrile

According to the same procedure as in Example 1(1), using 4-methoxy-3-(2-methylpropoxy)acetophenone instead of 3,4-dimethoxybenzaldehyde, 3-[4-methoxy-3-(2-methylpropoxy)phenyl]-3-hydroxybutyronitrile was obtained as a yellow oil.

$^1$H-NMR (400 MHz, CDCl$_3$) δ1.04 (6H, d, J=6.84 Hz), 1.76 (3H, s), 2.16 (1H, m, J=6.84 Hz), 2.77 (1H, d, J=16.11 Hz), 2.83 (1H, d, J=16.11 Hz), 3.78 (2H, d, J=6.84 Hz), 3.86 (3H, s), 6.85 (1H, d, J=8.30 Hz), 6.95 (1H, dd, J=8.30, 2.45 Hz), 7.05 (1H, d, J=2.45 Hz)

(3) Synthesis of 6-[4-methoxy-3-(2-methylpropoxy)phenyl]-6-methyl-3,4,5,6-tetrahydro-2H-1,3-oxazin-2-one According to the same procedure as in Example 1(2) to (3), using 3-[4-methoxy-3-(2-methylpropoxy)phenyl]-3-hydroxybutyronitrile instead of 3-(3,4-dimethoxyphenyl)-3-hydroxypropiononitrile, the above-described compound (yield 43.0%) was obtained as a colorless solid.

$^1$H-NMR (400 MHz, CDCl$_3$) δ1.03 (6H, d, J=6.35 Hz), 1.66 (3H, s), 2.10–2.18 (2H, m), 2.31 (1H, ddd, J=13.67, 4.40, 3.91 Hz), 3.07 (1H, ddd, J=11.23, 11.23, 4.40 Hz), 3.27 (1H, dddd, J=11.23, 5.37, 3.91, 3.91 Hz), 3.76 (1H, dd, J=9.28, 6.35 Hz), 3.79 (1H, dd, J=9.28, 6.35 Hz), 3.86 (3H, s), 5.02 (1H, broad s), 6.85–6.90 (3H, m)

Example 82

Synthesis of 3,6-dimethyl-6-[4-methoxy-3-(2-methylpropoxy)phenyl]-3,4,5,6-tetrahydro-2H-1,3-oxazin-2-one (Compound No. 82 of Table 1)

According to the same procedure as in Example 8, using the 6-[4-methoxy-3-(2-methylpropoxy)phenyl]-6-methyl-3, 4,5,6-tetrahydro-2H-1,3-oxazin-2-one produced in Example 82 instead of 6-(3,4-dimethoxyphenyl)-3,4,5,6-tetrahydro-2H-1,3-oxazin-2-one, the above-described compound (yield 79.7%) was obtained as a brown oil.

$^1$H-NMR (400 MHz, CDCl$_3$) δ1.03 (6H, d, J=6.84 Hz), 1.62 (3H, s), 2.15 (1H, m, J=6.84 Hz), 2.18 (1H, ddd, J=14.26, 10.74, 5.86 Hz), 2.35 (1H, ddd, J=14.26, 4.89, 3.42 Hz), 2.90 (3H, s), 3.03 (1H, ddd, J=11.72, 10.74, 4.89 Hz), 3.13 (1H, ddd, J=11.72, 5.86, 3.42 Hz), 3.75 (1H, dd, J=9.28, 6.84 Hz), 3.78 (1H, dd, J=9.28, 6.84 Hz), 3.86 (3H, s), 6.82 (1H, dd, J=8.30, 1.95 Hz), 6.85 (1H, d, J=8.30 Hz), 6.89 (1H, d, J=1.95 Hz)

Example 83

Synthesis of 6-[3-(2-benzyloxyethoxy)-4-methoxyphenyl]-3 4,5,6-tetrahydro-2H-1,3-oxazin-2-one (Compound No. 83 of Table 1)

(1) Synthesis of 3-(2-benzyloxyethoxy)-4-methoxybenzaldehyde

According to the same procedure as in Example 4(1), using 2-benzyloxyethanol instead of cyclopropylcarbinol, 3-(2-benzyloxyethoxy)-4-methoxybenzaldehyde (yield 83,4%) was obtained as a light yellow oil.

$^1$H-NMR (400 MHz, CDCl$_3$) δ3.89 (2H, t, J=4.88 Hz), 3.95 (3H, s), 4.27 (2H, t, J=4.88 Hz), 4.65 (2H, s), 6.97 (1H, d, J=8.30 Hz), 7.27–7.48 (7H, m), 9.83 (1H, s)

(2) Synthesis of 3-[3-(2-benzyloxyethoxy)-4-methoxyphenyl]-3-hydroxypropiononitrile According to the same procedure as in Example 1(1), using 3-(2-benzyloxyethoxy)-4-methoxybenzaldehyde instead of 3,4-dimethoxybenzaldehyde, 3-[3-(2-benzyloxyethoxy)-4-methoxyphenyl]-3-hydroxypropiononitrile was obtained as a brown oil.

$^1$H-NMR (400 MHz, CDCl$_3$) δ2.45 (1H, broad s), 2.65 (1H, dd, J=16.60, 6.34 Hz), 2.70 (1H, dd, J=16.60, 6.34 Hz), 3.86 (3H, s), 3.87 (2H, t, J=4.88 Hz), 4.22 (2H, t, J=4.88 Hz), 4.63 (2H, s), 4.91 (1H, t, J=6.34 Hz), 6.85 (1H, d, J=8.30 Hz), 6.92 (1H, dd, J=8.30, 1.95 Hz), 6.98 (1H, d, J=1.95 Hz), 7.34–7.36 (5H, m)

(3) Synthesis of 6-[3-(2-benzyloxyethoxy)-4-methoxyphenyl]-3,4,5,6-tetrahydro-2H-1,3-oxazin-2-one According to the same procedure as in Example 1(2) to (3), using 3-[3-(2-benzyloxyethoxy)-4-methoxyphenyl]-3-hydroxypropiononitrile instead of 3-(3,4-dimethoxyphenyl)-3-hydroxypropiononitrile, the above-described compound (yield 38.4%) was obtained as a light brown solid.

$^1$H-NMR (400 MHz, CDCl$_3$) δ1.98–2.08 (1H, m), 2.13 (1H, dddd, J=16.61, 8.30, 2.93, 2.93 Hz), 3.35 (1H, ddd, J=11.72, 5.86, 3.42 Hz), 3,41–3.48 (1H, m), 3.87 (3H, s), 3.87 (2H, t, J=5.37 Hz), 4.24 (2H, t, J=5.37 Hz), 4.64 (2H, s), 5.23 (1H, dd, J=10.25, 2.93 Hz), 5.46 (1H, broad s), 6.86 (1H, d, J=8.30 Hz), 6.92 (1H, dd, J=8.30, 1.95 Hz), 6.96 (1H, d, J=1.95 Hz), 7.27–7.40 (5H, m)

Example 84

Synthesis of 6-[3-(2-benzyloxyethoxy)-4-methoxyphenyl]-3-methyl-3,4,5,6-tetrahydro-2H-1,3-oxazin-2-one (Compound No. 84 of Table 1)

According to the same procedure as in Example 8, using the 6-[3-(2-benzyloxyethoxy)-4-methoxyphenyl]-3,4,5,6-tetrahydro-2H-1,3-oxazin-2-one produced in Example 84 instead of 6-(3,4-dimethoxyphenyl)-3,4,5,6-tetrahydro-2H-1,3-oxazin-2-one, the above-described compound (yield 87.9%) was obtained as a yellow brown oil.

$^1$H-NMR (400 MHz, CDCl$_3$) δ2.07–2.18 (2H, m), 3.03 (3H, s), 3.22 (1H, ddd, J=11.72, 5.86, 3.42 Hz), 3.44 (1H, ddd, J=11.72, 11.72, 5.86 Hz), 3.86 (3H, s), 3.86 (2H, t, J=4.88 Hz), 4.23 (2H, t, J=4.88 Hz), 4.63 (2H, s), 5.17 (1H, dd, J=9.76, 2.42 Hz), 6.85 (1H, d, J=8.30 Hz), 6.90 (1H, dd, J=8.30, 1.47 Hz), 6.95 (1H, d, J=1.47 Hz), 7.28–7.40 (5H, m)

Example 85

Synthesis of 6-(3-cyclopentyloxy-4-methoxyphenyl)-5,5-dimethyl-3,4,5,6-tetrahydro-2H-1,3-oxazin-2-one (Compound No. 85 of Table 1)

(1) Synthesis of 3-(3-cyclopentyloxy-4-methoxyphenyl)-2,2-dimethyl-3-hydroxypropiononitrile According to the same procedure as in Example 2(1), using isobutyronitrile instead of acetonitrile, 3-(3-cyclopentyloxy-4-methoxyphenyl)-2,2-dimethyl-3-hydroxypropiononitrile was obtained as a yellow solid.

$^1$H-NMR (400 MHz, CDCl$_3$) δ1.21 (3H, s), 1.46 (3H, s), 1.51–1.65 (2H, m), 1.79–2.02 (6H, m), 3.85 (3H, s), 4.49 (1H, s), 4.80 (1H, m), 6.84 (1H, d, J=8.30 Hz), 6.90 (1H, dd, J=8.30, 1.95 Hz), 7.04 (1H, d, J=1.95 Hz)

(2) Synthesis of 6-(3-cyclopentyloxy-4-methoxyphenyl)-5,5-dimethyl-3,4,5,6-tetrahydro-2H-1,3-oxazin-2-one According to the same procedure as in Example 1(2) to (3), using 3-(3-cyclopentyloxy-4-methoxyphenyl)-2,2-dimethyl-3-hydroxypropiononitrile instead of 3-(3,4-dimethoxyphenyl)-3-hydroxypropiononitrile, the above-described compound (yield 54.3%) was obtained as a colorless oil.

$^1$H-NMR (400 MHz, CDCl$_3$) δ0.92 (3H, s), 0.95 (3H, s), 1.60–1.62 (2H, m), 1.84–1.95 (6H, m), 3.04 (1H, dd, J=11.72, 3.91 Hz), 3.22 (1H, d, J=11.72 Hz), 3.84 (3H, s), 4.79 (1H, m), 4.97 (1H, s), 6.79–6.85 (3H, m), 6.95 (1H, broad)

Example 86

Synthesis of 6-(3-cyclopentyloxy-4-methoxyphenyl)-3,5,5-trimethyl-3,4,5,6-tetrahydro-2H-1,3-oxazin-2-one (Compound No. 86 of Table 1)

According to the same procedure as in Example 8, using the 6-(3-cyclopentyloxy-4-methoxyphenyl)-5,5-dimethyl-3,4,5,6-tetrahydro-2H-1,3-oxazin-2-one produced in Example 85 instead of 6-(3,4-dimethoxyphenyl)-3,4,5,6-tetrahydro-2H-1,3-oxazin-2-one, the above-described compound (yield 63.7%) was obtained as a colorless oil.

$^1$H-NMR (400 MHz, CDCl$_3$) δ0.92 (3H, s), 0.95 (3H, s), 1.58–1.62 (2H, m), 1.82–1.98 (6H, m), 2.92 (1H, d, J=11.72 Hz), 3.04 (3H, s), 3.29 (1H, d, J=11.72 Hz), 3.84 (3H, s), 4.79 (1H, m), 4.95 (1H, s), 6.75–6.85 (3H, m)

Example 87

Synthesis of 5.5-dimethyl-6-[3-(2-indanyloxy)-4-methoxyphenyl]-3,4,5,6-tetrahydro-2H-1,3-oxazin-2-one (Compound No. 87 of Table 1)

(1) Synthesis of 2,2-dimethyl-3-hydroxy-3-[3-(2-indanyloxy)-4-methoxyphenyl]propiononitrile According to the same procedure as in Example 24(2), using isobutyronitrile instead of acetonitrile, 2,2-dimethyl- 3-hydroxy-3-[3-(2-indanyloxy)-4-methoxyphenyl]propiononitrile was obtained as a brown oil.

$^1$H-NMR (400 MHz, CDCl$_3$) δ1.24 (3H, s), 1.47 (3H, s), 2.24 (1H, broad s), 3.20–3.27 (2H, m), 3.36–3.45 (2H, m), 3.82 (3H, s), 4.48 (1H, s), 5.22 (1H, m), 6.86 (1H, d, J=8.30 Hz), 6.96 (1H, dd, J=8.30, 1.95 Hz), 7.11 (1H, d, J=1.95 Hz), 7.16–7.19 (2H, m), 7.22–7.24 (2H, m)

(2) Synthesis of 5,5-dimethyl-6-[3-(2-indanyloxy)-4-methoxyphenyl]-3,4,5,6-tetrahydro-2H-1,3-oxazin-2-one According to the same procedure as in Example 1(2) to (3), using 2,2-dimethyl-3-hydroxy-3-[3-(2-indanyloxy)-4-methoxyphenyl]propiononitrile instead of 3-(3,4-dimethoxyphenyl)-3-hydroxypropiononitrile, the above-described compound (yield 75.9%) was obtained as an off white solid.

$^1$H-NMR (400 MHz, CDCl$_3$) δ0.96 (3H, s), 1.00 (3H, s), 3.06 (1H, dd, J=11.72, 4.39 Hz), 3.21–3.29 (3H, m), 3.36 (2H, ddd, J=16.60, 5.86, 5.86 Hz), 3.82 (3H, s), 5.00 (1H, s), 5.22 (1H, m), 5.25 (1H, broad), 6.86–6.90 (3H, m), 7.16–7.19 (2H, m), 7.22–7.28 (2H, m)

Example 88

Synthesis of 6-[3-(2-indanyloxy)-4-methoxyphenyl]-3,5,5-trimethyl-3,4,5,6-tetrahydro-2H-1,3-oxazin-2-one (Compound No. 88 of Table 1)

According to the same procedure as in Example 8, using the 5,5-dimethyl-6-[3-(2-indanyloxy)-4-methoxyphenyl]-5,5-dimethyl-3,4,5,6-tetrahydro-2H-1,3-oxazin-2-one produced in Example 87 instead of 6-(3,4-dimethoxyphenyl)-3,4,5,6-tetrahydro-2H-1,3-oxazin-2-one, the above-described compound (yield 86.2%) was obtained as an off white solid.

$^1$H-NMR (400 MHz, CDCl$_3$) δ0.94 (3H, s), 0.98 (3H, s), 2.93 (1H, d, J=11.72 Hz), 3.05 (3H, s), 3.22 (2H, ddd, J=16.60, 6.84, 3.91 Hz), 3.30 (1H, d, J=11.72 Hz), 3.35 (2H, ddd, J=16.60, 6.84, 6.84 Hz), 3.82 (3H, s), 4.96 (1H, s), 5.20 (1H, m), 6.85 (2H, s), 6.88 (1H, s), 7.16–7.18 (2H, m), 7.22–7.24 (2H, m)

Example 89

Synthesis of 6-[3-(1-benzyl-4-piperidyloxy)-4-methoxyphenyl]-3,4,5,6-tetrahydro-2H-1,3-oxazin-2-one (Compound No. 89 of Table 1)

(1) Synthesis of 3-(1-benzyl-4-piperidyloxy)-4-methoxybenzaldehyde

According to the same procedure as in Example 4(1), using 1-benzyl-4-hydroxypiperidine instead of cyclopropylcarbinol, 3-(1-benzyl-4-piperidyloxy)-4-methoxybenzaldehyde (yield 64.4%) was obtained as a light yellow oil.

$^1$H-NMR (400 MHz, CDCl$_3$) δ1.73–1.92 (2H, m), 2.00–2.06 (2H, m), 2.25–2.30 (2H, m), 2.78–2.84 (2H, m), 3.54 (2H, s), 3.93 (3H, s), 4.38 (1H, m), 6.98 (1H, d, J=8.30 Hz), 7.32 (1H, d, J=1.46 Hz), 7.33 (5H, m), 7.44 (1H, dd, J=8.30, 1.46 Hz), 9.83 (1H, s)

(2) Synthesis of 3-[3-(1-benzyl-4-piperidyloxy)-4-methoxyphenyl]-3-hydroxypropiononitrile According to the same procedure as in Example 1(1), using 3-(1-benzyl-4-piperidyloxy)-4-methoxybenzaldehyde instead of 3,4-dimethoxybenzaldehyde, 3-[3-(1-benzyl-4-piperidyloxy)-4-methoxyphenyl]-3-hydroxypropiononitrile was obtained as a brown oil.

$^1$H-NMR (400 MHz, CDCl$_3$) δ1.84–1.88 (2H, m), 1.96 (2H, m), 2.25 (2H, m), 2.72–2.78 (5H, m), 3.53 (2H, s), 3.84 (3H, s), 4.27 (1H, m), 4.95 (1H, t, J=6.35 Hz), 6.87 (1H, d, J=8.30 Hz), 6.94 (1H, dd, J=8.30, 1.95 Hz), 6.98 (1H, d, J=1.95 Hz), 7.31–7.32 (5H, m)

(3) Synthesis of 6-[3-(1-benzyl-4-piperidyloxy)-4-methoxyphenyl]-3,4,5,6-tetrahydro-2H-1,3-oxazin-2-one According to the same procedure as in Example 1(2) to (3), using 3-[3-(1-benzyl-4-piperidyloxy)-4-methoxyphenyl]-3-hydroxypropiononitrile instead of 3-(3,4-dimethoxyphenyl)-3-hydroxypropiononitrile, the above-described compound (yield 41.0%) was obtained as a light yellow solid.

$^1$H-NMR (400 MHz, CDCl$_3$) δ1.85–1.89 (2H, m), 1.97 (2H, m), 2.07 (1H, dddd, J=13.67, 10.25, 10.25, 5.86 Hz), 2.17–2.20 (1H, m), 2.25 (2H, m), 2.79 (2H, m), 3.36–3,41 (1H, m), 3.44–3.48 (1H, m), 3.54 (2H, s), 3.84 (3H, s), 4.27 (1H, m), 5.23 (1H, broad s), 5.25 (1H, dd, J=9.76, 2.93 Hz), 6.87 (1H, d, J=8.30 Hz), 6.92–6.94 (2H, m), 7.30–7.33 (4H, m)

Example 90

Synthesis of 6-[3-[2-(cyclopropylmethyloxy)ethoxy]-4-methoxyphenyl]-3,4,5,6-tetrahydro-2H-1,3-oxazin-2-one (Compound No. 90 of Table 1)

(1) Synthesis of 3-[2-(cyclopropylmethyloxy)ethoxy]-4-methoxybenzaldehyde

According to the same procedure as in Example 4(1), using 2-(cyclopropylmethyloxy)ethanol instead of cyclopropylcarbinol, 3-[2-(cyclopropylmethyloxy)ethoxy]-4-methoxybenzaldehyde (yield 87.2%) was obtained as a pale yellow oil.

$^1$H-NMR (400 MHz, CDCl$_3$) δ0.21–0.24 (2H, m), 0.52–0.57 (2H, m), 1.10 (1H, m), 3.40 (2H, d, J=6.84 Hz), 3.89 (2H, t, J=4.88 Hz), 3.95 (3H, s), 4.25 (2H, t, J=4.88 Hz), 6.98 (1H, d, J=7.81 Hz), 7.45–7.48 (2H, m), 9.84 (1H, s)

(2) Synthesis of 3-[3-[2-(cyclopropylmethyloxy)ethoxy]-4-methoxyphenyl]-3-hydroxypropiononitrile According to the same procedure as in Example 1(1), using 3-[2-(cyclopropylmethyloxy)ethoxy]-4-methoxybenzaldehyde instead of 3,4-dimethoxybenzaldehyde, 3-[3-[2-(cyclopropylmethyloxy)ethoxy]-4-methoxyphenyl]-3-hydroxypropiononitrile was obtained as a dark brown oil.

$^1$H-NMR (400 MHz, CDCl$_3$) δ0.20–0.24 (2H, m), 0.52–0.56 (2H, m), 1.09 (1H, m), 2.41 (1H, broad), 2.73 (1H, dd, J=16.60, 6.35 Hz), 2.77 (1H, dd, J=16.60, 6.35 Hz), 3.39 (2H, d, J=6.83 Hz), 3.86 (3H, s), 3.86 (2H, t, J=5.37 Hz), 4.20 (2H, t, J=5.37 Hz), 4.97 (1H, t, J=6.35 Hz), 6.86 (1H, d, J=8.30 Hz), 6.94 (1H, dd, J=8.30, 1.95 Hz), 7.01 (1H, d, J=1.95 Hz)

(3) Synthesis of 6-[3-[2-(cyclopropylmethyloxy)ethoxy]-4-methoxyphenyl]-3,4,5,6-tetrahydro-2H-1,3-oxazin-2-one According to the same procedure as in Example 1(2) to (3), using 3-[3-[2-(cyclopropylmethyloxy)ethoxy]-4- methoxyphenyl]-3-hydroxypropiononitrile instead of 3-(3, 4-dimethoxyphenyl)-3-hydroxypropiononitrile, the above-described compound (yield 13,4%) was obtained as a pale brown solid.

$^1$H-NMR (400 MHz, CDCl$_3$) δ0.21–0.24 (2H, m), 0.52–0.56 (2H, m), 1.04–1.13 (1H, m), 2.07 (1H, dddd, J=14.16, 10.25, 10.25, 5.86 Hz), 2.18–2.20 (1H, m), 3.36–3.42 (1H, m), 3.40 (2H, d, J=6.84 Hz), 3.48 (1H, ddd, J=11.23, 11.23, 4.88 Hz), 3.86 (3H, s), 3.86 (2H, t, J=5.37 Hz), 4.20 (2H, t, J=5.37 Hz), 5.26 (1H, dd, J=10.25, 2.93 Hz), 5.35 (1H, broad), 6.86 (1H, d, J=8.30 Hz), 6.92 (1H, dd, J=8.30, 1.95 Hz), 6.97 (1H, d, J=1.95 Hz)

Example 91

Synthesis of rel-(5R,6S)-6-(3-cyclopentyloxy-4-methoxyphenyl)-5-phenyl-3,4,5,6-tetrahydro-2H-1, 3-oxazin-2-one (Compound No. 91 of Table 1, wherein the planar structural formula is shown)

(1) Synthesis of 3-(3-cyclopentyloxy-4-methoxyphenyl)-3-hydroxy-2-phenylpropiononitrile According to the same procedure as in Example 2(1), using phenylacetonitrile instead of acetonitrile, a crude product of 3-(3-cyclopentyloxy-4-methoxyphenyl)-3-hydroxy-2-phenylpropiononitrile 1.53 g was obtained as a yellow oil.

(2) Synthesis of 3-amino-1-(3-cyclopentyloxy-4-methoxyphenyl)-2-phenyl-1-propanol According to the same procedure as in Example 1(2), using 3-(3-cyclopentyloxy-4-methoxyphenyl)-3-hydroxy-2-phenylpropiononitrile instead of 3-(3,4-dimethoxyphenyl)-3-hydroxypropiononitrile, the above-described compound (yield 51.3%) was obtained as a light yellow oil.

(3) Synthesis of 1-(3-cyclopentyloxy-4-methoxyphenyl)-3-(methoxycarbonylamino)-2-phenyl-1-propanol According to the same procedure as in Example 1(3), using 3-amino-1-(3-cyclopentyloxy-4-methoxyphenyl)-2-phenyl-1-propanol instead of 3-amino-1-(3,4-dimethoxyphenyl)-1-propanol, a diastereo mixture of the above-described compound was obtained as a colorless oil. The mixture was separated by flash column chromatography (SiO$_2$; eluted by 1.5% methanol/methylene chloride) to obtain a large Rf value fraction 0.36 g (yield 39.0%) and a small Rf value fraction 0.49 g (yield 53.5%).

(4) Synthesis of rel-(5R,6S)-6-(3-cyclopentyloxy-4-methoxyphenyl)-5-phenyl-3,4,5,6-tetrahydro-2H-1, 3-oxazin-2-one According to the same procedure as in Example 1(3), using the large Rf value fraction of the 1-(3-cyclopentyloxy-4-methoxyphenyl)-3-(methoxycarbonylamino)-2-phenyl-1-propanol obtained in (3) instead of 1-(3,4-dimethoxyphenyl)-3-(methoxycarbonylamino)-1-propanol, the above-described compound (yield 85.1%) was obtained as a colorless solid.

$^1$H-NMR (400 MHz, CDCl$_3$) δ1.50–1.73 (8H, m), 3.50–3.53 (1H, m), 3.64–3.70 (1H, m), 3.75–3.80 (1H, m), 3.80 (3H, s), 4.38 (1H, m), 5.57 (1H, broad), 5.61 (1H, d, J=3,41 Hz), 6.27 (1H, d, J=1.95 Hz), 6.58 (1H, dd, J=8.30, 1.95 Hz), 6.73 (1H, d, J=8.30 Hz), 6.91–6.93 (2H, m), 7.21–7.22 (3H, m), Example 92

Synthesis of rel-(5R,6R)-6-(3-cyclopentyloxy-4-methoxyphenyl)-5-phenyl-3,4,5,6-tetrahydro-2H-1, 3-oxazin-2-one (Compound No. 92 of Table 1, wherein the planar structural formula is shown)

According to the same procedure as in Example 1(3), using the small Rf value fraction of the 1-(3-cyclopentyloxy-4-methoxyphenyl)-3-(methoxycarbonylamino)-2-phenyl-1-propanol obtained in Example 92(3) instead of 1-(3,4-dimethoxyphenyl)-3-(methoxycarbonylamino)-1-propanol, the above-described compound (yield 99.3%) was obtained as a light yellow solid.

$^1$H-NMR (400 MHz, CDCl$_3$) δ1.51–1.86 (8H, m), 3.24 (1H, ddd, J=10.74,10.25,5.37 Hz), 3.57 (1H, ddd, J=10.74, 5.37,5.37 Hz), 3.69 (1H, m), 3.76 (3H, s), 4.58 (1H, m), 5.31 (1H, d, J=10.25 Hz), 5.70 (1H, broad), 6.59 (1H, s), 6.68 (2H, s), 7.02–7.04 (2H, m), 7.17–7.25 (3H, m)

Example 93

Synthesis of 6-[3-(3-tetrahydrofuryloxy)-4-methoxyphenyl]-3,4,5,6-tetrahydro-2H-1,3-oxazin-2-one (Compound No. 93 of Table 1)

(1) Synthesis of 3-(3-tetrahydrofuryloxy)-4-methoxybenzaldehyde

According to the same procedure as in Example 4(1), using 3-hydroxytetrahydrofuran instead of cyclopropylcarbinol, 3-(3-tetrahydrofuryloxy)-4-methoxybenzaldehyde (yield 71.3%) was obtained as a colorless solid.

$^1$H-NMR (400 MHz, CDCl$_3$) δ2.18–2.30 (2H, m), 3.89–3.93 (2H, m), 3.94 (3H, s), 3.99–4.07 (2H, m), 5.01–5.05 (1H, m), 6.99 (1H, d, J=8.30 Hz), 7.35 (1H, d, J=1.95 Hz), 7.49 (1H, dd, J=8.30,1.95 Hz), 9.84 (1H, s)

(2) Synthesis of 3-[3-(3-tetrahydrofuryloxy)-4-methoxyphenyl]-3-hydroxypropiononitrile According to the same procedure as in Example 1(1), using 3-(3-tetrahydrofuryloxy)-4-methoxybenzaldehyde instead of 3,4-dimethoxybenzaldehyde, 3-[3-(3-tetrahydrofuryloxy)-4-methoxyphenyl]-3-hydroxypropiononitrile was obtained as a yellow oil.

$^1$H-NMR (400 MHz, CDCl$_3$) δ2.17–2.20 (2H, m), 2.74 (2H, d, J=6.35 Hz), 3.85 (3H, s), 3.87–4.03 (4H, m), 4.97–4.98 (3H, m), 6.87–6.98 (3H, m)

(3) Synthesis of 6-[3-(3-tetrahydrofuryloxy)-4-methoxyphenyl]-3,4,5,6-tetrahydro-2H-1,3-oxazin-2-one According to the same procedure as in Example 1(2) to (3), using 3-[3-(3-tetrahydrofuryloxy)-4-methoxyphenyl]-3-hydroxypropiononitrile instead of 3-(3,4-dimethoxyphenyl)-3-hydroxypropiononitrile, the above-described compound (yield 24.7%) was obtained as a light brown solid.

$^1$H-NMR (400 MHz, CDCl$_3$) δ2.03–2.15 (2H, m), 2.16–2.23 (2H, m), 3.39 (1H, m), 3,49 (1H, m), 3.86 (3H, s), 3.87–4.06 (4H, m), 4.96–5.00 (1H, m), 5.25–5.28 (1H, broad), 5.26 (1H, m), 6.88 (1H, m), 6.88 (1H, m), 6.94 (1H, m)

TABLE 1

[Structure: 3,4-dialkoxyphenyl-substituted 1,3-oxazinan-2-one with R₁O and R₂O on phenyl, R₄ at C6, R₅ R₆ at C5, R₃ on N]

| Compound No. | R₁ | R₂ | R₃ | R₄ | R₅ | R₆ |
|---|---|---|---|---|---|---|
| 1 | Me | Me | H | H | H | H |
| 2 | cyclopentyl-CH₂– | Me | H | H | H | H |
| 3 | Bu | Me | H | H | H | H |
| 4 | cyclopropyl-CH₂CH₂– | Me | H | H | H | H |
| 5 | Me | Me | H | Me | H | H |
| 6 | cyclopentyl-CH₂– | Me | H | Me | H | H |
| 7 | cyclopentyl-CH₂– | Me | H | Ph | H | H |
| 8 | Me | Me | Me | H | H | H |
| 9 | Me | Me | –CH₂CH₂–Ph | H | H | H |
| 10 | cyclopentyl-CH₂– | Me | Me | H | H | H |
| 11 | cyclopentyl-CH₂– | Me | –CH₂CH₂–(4-bromophenyl) | H | H | H |
| 12 | cyclopentyl-CH₂– | Me | –CH₂CH₂–(quinolin-2-yl) | H | H | H |
| 13 | cyclopentyl-CH₂– | Me | –CH₂CH₂–(naphthalen-1-yl) | H | H | H |

TABLE 1-continued

| Compound No. | R₁ | R₂ | R₃ | R₄ | R₅ | R₆ |
|---|---|---|---|---|---|---|
| 14 | cyclopentyl | Me | 4-pyridylethyl | H | H | H |
| 15 | cyclopentyl | Me | 2-naphthylethyl | H | H | H |
| 16 | cyclopentyl | Me | 2-pyridylethyl | H | H | H |
| 17 | cyclopentyl | Me | Bu | H | H | H |
| 18 | cyclopentyl | Me | phenacyl (PhCOCH₂) | H | H | H |
| 19 | cyclopentyl | Me | EtOOC-CH₂CH₂ | H | H | H |
| 20 | cyclopentyl | Me | 3-pyridylethyl | H | H | H |
| 21 | cyclopentyl | Me | Me | Me | H | H |
| 22 | cyclopentyl | Me | 4-pyridylethyl | Me | H | H |
| 23 | phenylpropyl | Me | H | H | H | H |

TABLE 1-continued

| Compound No. | $R_1$ | $R_2$ | $R_3$ | $R_4$ | $R_5$ | $R_6$ |
|---|---|---|---|---|---|---|
| 24 | 2-indanyl | Me | H | H | H | H |
| 25 | 2-indanyl | Me | Me | H | H | H |
| 26 | cyclopentyl | Me | H | Et | H | H |
| 27 | Me | Me | H | 2-thiazolyl-methyl | H | H |
| 28 | cyclopentyl | Me | Et | H | H | H |
| 29 | cyclopentyl | Me | H | 2-thienyl-methyl | H | H |
| 30 | cyclopentyl | Me | H | Bu | H | H |
| 31 | cyclopentyl | Me | H | 2-thiazolyl-methyl | H | H |
| 32 | cyclopentyl | Me | 3-(piperidin-1-yl)propyl | H | H | H |
| 33 | cyclopentyl | Me | 3-(morpholin-4-yl)propyl | H | H | H |

TABLE 1-continued
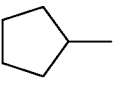
| Compound No. | R₁ | R₂ | R₃ | R₄ | R₅ | R₆ |
|---|---|---|---|---|---|---|
| 34 | 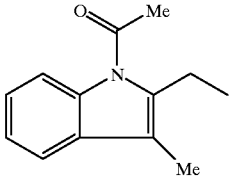 | Me | 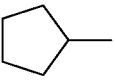 | H | H | H |
| 35 | 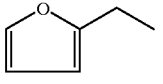 | Me | 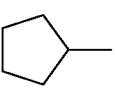 | H | H | H |
| 36 | 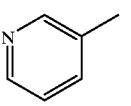 | Me | H | 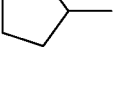 | H | H |
| 37 | 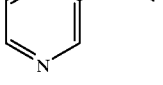 | Me | 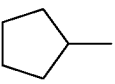 | H | H | H |
| 38 | 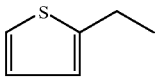 | Me | 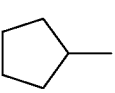 | H | H | H |
| 39 | 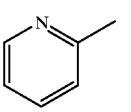 | Me | H | 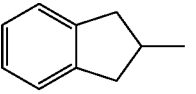 | H | H |
| 40 | 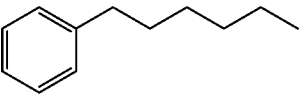 | Me | H | Me | H | H |
| 41 | 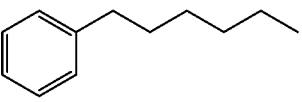 | Me | H | H | H | H |
| 42 | 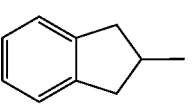 | Me | Me | H | H | H |
| 43 |  | Me | Me | Me | H | H |

TABLE 1-continued

| Compound No. | R₁ | R₂ | R₃ | R₄ | R₅ | R₆ |
|---|---|---|---|---|---|---|
| 44 | PhCH₂CH₂CH₂– | Me | Me | H | H | H |
| 45 | Ph(CH₂)₅– | Me | H | Me | H | H |
| 46 | PhCH₂CH₂– | Me | H | Me | H | H |
| 47 | Ph(CH₂)₅– | Me | Me | Me | H | H |
| 48 | PhCH₂CH₂CH₂– | Me | Me | Me | H | H |
| 49 | cyclopropyl-CH₂– | Me | Me | H | H | H |
| 50 | cyclopropyl-CH₂– | Me | H | Me | H | H |
| 51 | cyclopropyl-CH₂– | Me | Me | Me | H | H |
| 52 | Bu | Me | H | Me | H | H |
| 53 | Bu | Me | Me | H | H | H |
| 54 | Bu | Me | Me | Me | H | H |
| 55 | 2-pyridyl-CH₂CH₂– | Me | H | H | H | H |
| 56 | 1-phenylcyclopropyl-CH₂– | Me | H | H | H | H |

TABLE 1-continued

| Compound No. | R₁ | R₂ | R₃ | R₄ | R₅ | R₆ |
|---|---|---|---|---|---|---|
| 57 | 1-ethyl-1-phenylcyclopropyl | Me | Me | H | H | H |
| 58 | 10,11-dihydro-5H-dibenzo[a,d]cyclohepten-5-yl (methyl) | Me | H | H | H | H |
| 59 | 10,11-dihydro-5H-dibenzo[a,d]cyclohepten-5-yl (methyl) | Me | Me | H | H | H |
| 60 | 4-benzylpiperazin-1-yl butyl | Me | H | H | H | H |
| 61 | cyclobutylmethyl (ethyl) | Me | H | H | H | H |
| 62 | cyclobutylmethyl (ethyl) | Me | Me | H | H | H |
| 63 | 1-methylcyclopropylethyl | Me | H | H | H | H |
| 64 | 1-methylcyclopropylethyl | Me | Me | H | H | H |
| 65 | isobutyl (sec-butyl) | Me | H | H | H | H |
| 66 | isobutyl (sec-butyl) | Me | Me | H | H | H |

TABLE 1-continued
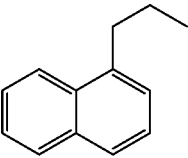
| Compound No. | R₁ | R₂ | R₃ | R₄ | R₅ | R₆ |
|---|---|---|---|---|---|---|
| 67 | 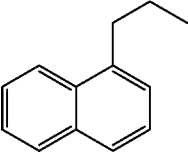 | Me | H | H | H | H |
| 68 | 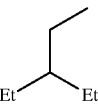 | Me | Me | H | H | H |
| 69 | 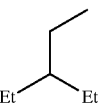 | Me | H | H | H | H |
| 70 | 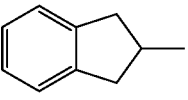 | Me | Me | H | H | H |
| 71 | 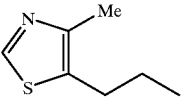 | Me | Et | H | H | H |
| 72 | 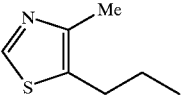 | Me | H | H | H | H |
| 73 | 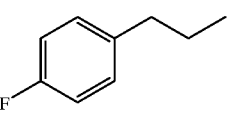 | Me | Me | H | H | H |
| 74 | 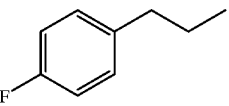 | Me | H | H | H | H |
| 75 |  | Me | Me | H | H | H |

TABLE 1-continued
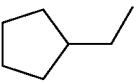
| Compound No. | R₁ | R₂ | R₃ | R₄ | R₅ | R₆ |
|---|---|---|---|---|---|---|
| 76 | 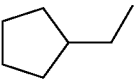 | Me | H | H | H | H |
| 77 | 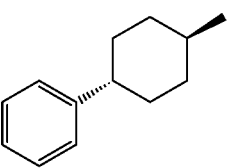 | Me | Me | H | H | H |
| 78 | 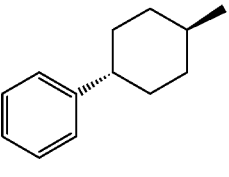 | Me | H | H | H | H |
| 79 |  | Me | Me | H | H | H |
| 80 | 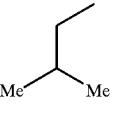 | Me | H | H | H | H |
| 81 | 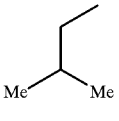 | Me | H | Me | H | H |
| 82 | 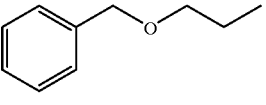 | Me | Me | Me | H | H |
| 83 | 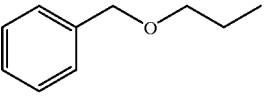 | Me | H | H | H | H |
| 84 | 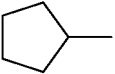 | Me | Me | H | H | H |
| 85 |  | Me | H | H | Me | Me |

TABLE 1-continued

| Compound No. | R₁ | R₂ | R₃ | R₄ | R₅ | R₆ |
|---|---|---|---|---|---|---|
| 86 | 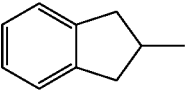 | Me | Me | H | Me | Me |
| 87 | 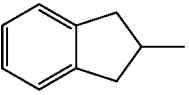 | Me | H | H | Me | Me |
| 88 | 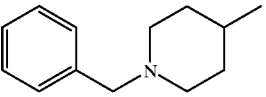 | Me | Me | H | Me | Me |
| 89 | 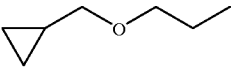 | Me | H | H | H | H |
| 90 | 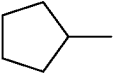 | Me | H | H | H | H |
| 91 | 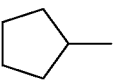 | Me | H | H | Ph | H |
| 92 | 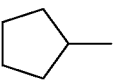 | Me | H | H | H | Ph |
| 93 | 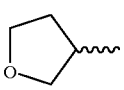 | Me | H | H | H | H |

Example 95

Production of Tablets 6-(3-Cyclopentyloxy-4-methoxyphenyl)-6-methyl-3,4,5,6-tetrahydro-2H-1,3-oxazin-2-one (Compound No. 6 of Table 1) (30 g), lactose (253 g), corn starch (63 g), low substituted hydroxypropylcellulose (40 g), and calcium stearate (4 g) were mixed together, then compressed by an ordinary method so that each tablet contained 10 mg of the above compound.

Example 96

Production of Capsules 6-(3-Cyclopentyloxy-4-methoxyphenyl)-3-(4-pyridylmethyl)-3,4,5,6-tetrahydro-2H-1,3-oxazin-2-one (Compound No. 12 of Table 1) (30 g), lactose (260 g), corn starch (66 g), and calcium stearate (4 g) were mixed together, then were filled into a gelatin capsule by an ordinary method so that each capsule contained 10 mg of the above compound.

Example 97

Production of Inhalant 6-(3-Cyclopentyloxy-4-methoxyphenyl)-3-methyl-3,4,5,6-tetrahydro-2H-1,3-oxazin-2-one (Compound No. 10 of Table 1) (0.15 g) pulverized well to a particle size of 1 to 5 μm and lactose (60 g) (325 mesh, DMV Co.) were mixed together. This was filled in capsules by an ordinary method so that each capsule contained (50 μg) of the compound. Inhalation was performed by charging a capsule in a powder inhalation container.

Test Example 1

Separation of Phosphodiesterase (PDE) and Measurement of PDE Inhibitory Activity Type I, III, IV, and V PDE isozymes were prepared to study the PDE inhibitory activities and selectivities with the compound of the invention [Trends Pharmacol. Sci., 12, 19–27 (1992)]. Type I PDE was purchased from Sigma Corp. Type III, IV, and V PDE isozymes were partially purified from rats platelets (Type III and V) or neutrophils (Type IV). Each enzyme source was homogenized in a buffer (pH 6.5) containing 20 mM bisTris, 2 mM EDTA (ethylenediamine tetraacetate), 0.1 mM PMSF (phenylmethylsulfonyl fluoride), 5 mM 2-mercaptoethanol, 0.001 mM pepstatin, and 0.01 mM leupeptin and was centrifuged at 30,000×G for 30 minutes to obtain a supernatant, which was applied to an ion exchange column (Q-sepharose First Flow, Pharmacia Corp.) and was eluted with 0 to 1M sodium acetate. Partially purified isozymes were identified by observing the effects of conventional inhibitors.

Each PDE isozyme and the test compound dissolved in DMSO (dimethyl sulfoxide) were added to 50 mM Tris-HCl buffer containing 5 mM magnesium chloride. $^3$H-cAMP (for type III and IV PDE) or $^3$H-cGMP (for type I and V PDE) were added as substrates and were reacted at 30° C. for 30 minutes. The reaction was terminated by placing the test tube in boiling water of 100° C. for 5 minutes. The nucleotides formed by PDE were broken down by 5'-nucleotidase to $^3$H-adenosine or $^3$H-guanosine. The unreacted substrate and reaction product were separated through an ion-exchange column (QAE sephadex, Pharmacia Corp.) The eluted $^3$H-nucleoside was measured for its radioactivity by a liquid scintillation counter. The inhibiting activities of the compound of the present invention are shown by the $IC_{50}$ value (M). The inhibitory activities against Type IV is shown in Table 2. Further, the inhibitory activities of the test samples against Type I, III, and V are 1/10 or less than that against type IV.

TABLE 2

| Compound No. | Type IV PDE inhibitory activity $IC_{50}$ (M) |
|---|---|
| 1 | $1.0 \times 10^{-5}$ |
| 2 | $1.2 \times 10^{-6}$ |
| 3 | $6.8 \times 10^{-6}$ |
| 4 | $3.2 \times 10^{-6}$ |
| 5 | $6.8 \times 10^{-6}$ |
| 6 | $1.1 \times 10^{-6}$ |
| 7 | $4.3 \times 10^{-6}$ |
| 8 | $1.9 \times 10^{-5}$ |
| 9 | $2.2 \times 10^{-5}$ |
| 10 | $1.3 \times 10^{-6}$ |
| 11 | $1.4 \times 10^{-6}$ |
| 12 | $7.3 \times 10^{-8}$ |
| 13 | $1.7 \times 10^{-6}$ |
| 14 | $6.1 \times 10^{-6}$ |
| 15 | $9.8 \times 10^{-7}$ |
| 16 | $5.5 \times 10^{-6}$ |
| 17 | $2.1 \times 10^{-6}$ |
| 18 | $4.1 \times 10^{-7}$ |
| 19 | $1.8 \times 10^{-6}$ |
| 20 | $3.5 \times 10^{-6}$ |
| 21 | $6.6 \times 10^{-7}$ |
| 22 | $5.9 \times 10^{-6}$ |
| 23 | $1.5 \times 10^{-6}$ |
| 24 | $1.3 \times 10^{-7}$ |
| 25 | $1.9 \times 10^{-7}$ |
| 26 | $3.5 \times 10^{-6}$ |
| 27 | $2.1 \times 10^{-5}$ |
| 28 | $1.7 \times 10^{-6}$ |
| 29 | $3.4 \times 10^{-6}$ |
| 30 | $9.0 \times 10^{-6}$ |
| 31 | $4.6 \times 10^{-6}$ |
| 32 | $3.2 \times 10^{-5}$ |
| 33 | $8.8 \times 10^{-6}$ |
| 34 | $8.6 \times 10^{-7}$ |
| 35 | $2.0 \times 10^{-6}$ |
| 36 | $1.6 \times 10^{-6}$ |
| 37 | $4.5 \times 10^{-6}$ |
| 38 | $2.2 \times 10^{-6}$ |
| 39 | $1.8 \times 10^{-5}$ |
| 40 | $5.0 \times 10^{-8}$ |
| 41 | $7.3 \times 10^{-7}$ |
| 42 | $1.0 \times 10^{-6}$ |
| 43 | $6.6 \times 10^{-8}$ |
| 44 | $1.5 \times 10^{-6}$ |
| 45 | $2.6 \times 10^{-7}$ |
| 46 | $4.9 \times 10^{-7}$ |
| 47 | $2.2 \times 10^{-7}$ |
| 48 | $7.0 \times 10^{-7}$ |
| 49 | $2.0 \times 10^{-6}$ |
| 50 | $1.1 \times 10^{-6}$ |
| 51 | $1.9 \times 10^{-6}$ |
| 52 | $1.4 \times 10^{-6}$ |
| 53 | $9.1 \times 10^{-6}$ |
| 54 | $2.0 \times 10^{-6}$ |
| 55 | $1.7 \times 10^{-6}$ |
| 56 | $9.4 \times 10^{-7}$ |
| 57 | $1.3 \times 10^{-6}$ |
| 58 | $9.4 \times 10^{-6}$ |
| 59 | $2.7 \times 10^{-5}$ |
| 60 | $5.2 \times 10^{-5}$ |
| 61 | $3.2 \times 10^{-6}$ |
| 62 | $3.3 \times 10^{-6}$ |
| 63 | $3.4 \times 10^{-6}$ |
| 64 | $4.6 \times 10^{-6}$ |
| 65 | $2.2 \times 10^{-6}$ |
| 66 | $3.8 \times 10^{-6}$ |
| 67 | $1.1 \times 10^{-6}$ |
| 68 | $2.6 \times 10^{-6}$ |
| 69 | $5.0 \times 10^{-6}$ |
| 70 | $3.5 \times 10^{-6}$ |
| 71 | $3.1 \times 10^{-7}$ |
| 72 | $8.3 \times 10^{-6}$ |
| 73 | $7.3 \times 10^{-6}$ |
| 74 | $1.3 \times 10^{-6}$ |
| 75 | $1.8 \times 10^{-6}$ |
| 76 | $2.9 \times 10^{-6}$ |
| 77 | $3.3 \times 10^{-6}$ |
| 78 | $1.9 \times 10^{-6}$ |
| 79 | $1.2 \times 10^{-6}$ |
| 80 | $1.5 \times 10^{-6}$ |
| 81 | $1.3 \times 10^{-6}$ |
| 82 | $1.9 \times 10^{-6}$ |
| 83 | $3.4 \times 10^{-6}$ |
| 84 | $3.1 \times 10^{-6}$ |
| 85 | $7.8 \times 10^{-7}$ |
| 86 | $8.6 \times 10^{-7}$ |
| 87 | $8.8 \times 10^{-8}$ |
| 88 | $1.9 \times 10^{-7}$ |
| 89 | $3.5 \times 10^{-5}$ |
| 90 | $1.9 \times 10^{-6}$ |
| 91 | $2.7 \times 10^{-6}$ |
| 92 | $9.0 \times 10^{-7}$ |
| 93 | $3.7 \times 10^{-6}$ |

Test Example 2

Inhibitory effects on activity of rat neutrophils

The release of super oxide anions was measured so as to study the inhibitory effects of the compound on inflammatory leukocytes, that is, neutrophils.

Blood sample was obtained from Wister rats anesthetized with ether. It was superposed on a blood cell separation solution (Polymorphoprep 1.113, made by Naicomet Co. (phonetic)) and the neutrophils were separated by centrifugation. The neutrophils were resuspended in a Hank's balanced salt solution at a concentration of $0.5 \times 10^4$ cell/ml. 0.1 mM of Lusigenin and the test substance dissolved in DMSO were added to 2 ml of the cell-suspension. The chemiluminescence generated by stimulation of 0.3 $\mu$M calcium ionophore A23187 was measured by a chemiluminescence reader so as to evaluate the release of super oxide anions. The efficacy of the compounds of the present invention was expressed by an $IC_{50}$ value and is shown in Table 3.

TABLE 3

| Compound No. | Inhibitory action of super oxide anion release from rat neutrophils $IC_{50}$ (M) |
| --- | --- |
| 1 | $8.8 \times 10^{-6}$ |
| 2 | $5.5 \times 10^{-7}$ |
| 5 | $2.4 \times 10^{-6}$ |
| 8 | $4.1 \times 10^{-6}$ |
| 9 | $2.3 \times 10^{-6}$ |
| 10 | $9.0 \times 10^{-8}$ |
| 11 | $5.0 \times 10^{-8}$ |

Test Example 3

Inhibitory effect on antigen-induced Bronchospasm (anti-asthmatic action)

A Hartley male guinea pig was sensitized by intramuscular administration of 35 mg Ovalbumin (OA) on first day and fourth day, and used after 24th day. A trachial canula was introduced in the guinea pig anesthetized with pentobarbital and artificial ventilation was performed 25 to 29 days after the first sensitization. The overflow of the ventilation was measured by the Konzett-Roessler method while 0.2 mg/kg OA were administered intravenously. The test compound was dissolved in polyethylene glycol 400 and intravenously administered 10 minutes before administration of the antigens. The effect of the present invention was expressed by the $ED_{50}$ value and is shown in Table 4.

TABLE 4

| Compound No. | Action for suppressing antigen-induced bronchospasms $ED_{50}$ (mg/kg) |
| --- | --- |
| 2 | 0.23 |
| 4 | 0.23 |
| 5 | 0.30 |
| 6 | 0.30 |
| 10 | 0.95 |
| 11 | 3.1 |
| 14 | 2.4 |
| 16 | 2.1 |
| 20 | 8.5 |
| 21 | 0.29 |
| 23 | 13.6 |
| 24 | 1.6 |
| 25 | 0.061 |
| 26 | 2.4 |
| 28 | 7.4 |
| 40 | 0.47 |
| 43 | 0.29 |
| 46 | 11.4 |
| 49 | 3.10 |
| 50 | 0.30 |
| 51 | 2.23 |

TABLE 4-continued

| Compound No. | Action for suppressing antigen-induced bronchospasms $ED_{50}$ (mg/kg) |
| --- | --- |
| 56 | 1.72 |
| 57 | 15.9 |
| 61 | 1.84 |
| 65 | 0.22 |
| 66 | 0.051 |
| 71 | 2.67 |
| 76 | 0.27 |
| 81 | 0.028 |
| 82 | 0.045 |

Test Example 4

Acute Toxicity Test

Compounds No. 1 to 93 were suspended in a saline containing 0.5% sodium carboxylmethylcellulose and were administered intraperitoneally. The survival rate of the next day was examined. No death was observed at a dosage of 30 mg/kg of any compound.

Industrial Applicability

As described above, the compound according to the present invention exhibits an excellent type IV PDE inhibitory activity and is very useful for treating inflammatory diseases such as asthma and dermatitis and autoimmune diseases such as multiple sclerosis and rheumatism.

What is claimed is:

1. A 6-phenyltetrahydro-1,3-oxazin-2-one derivative having the formula (I):

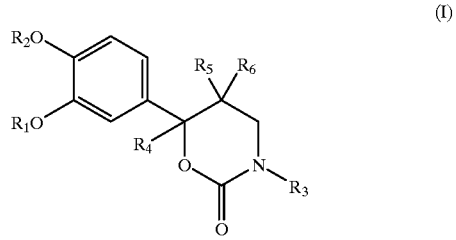

wherein:
  $R_1$ represents an unsubstituted or substituted $C_1$ to $C_8$ alkyl group, an unsubstituted or substituted $C_3$ to $C_7$ cycloalkyl group, an unsubstituted or substituted heterocycle, or a polycyclic hydrocarbon;
  $R_2$ represents a $C_1$ to $C_4$ alkyl group;
  $R_3$ is a hydrogen atom, an unsubstituted or substituted $C_1$ to $C_5$ alkyl group, an unsubstituted or substituted $C_3$ to $C_7$ cycloalkyl group, an unsubstituted or substituted aryl group, an unsubstituted or substituted heteroaryl group, or an acyl group;
  $R_4$ is a hydrogen atom, an unsubstituted or substituted $C_1$ to $C_6$ alkyl group, an unsubstituted or substituted aryl group, or an unsubstituted or substituted heteroaryl group; and
  $R_5$ and $R_6$ are each independently a hydrogen atom, an unsubstituted or substituted $C_1$ to $C_5$ alkyl group, an unsubstituted or substituted $C_3$ to $C_7$ cycloalkyl group, an unsubstituted or substituted aryl group, or an unsubstituted or substituted heteroaryl group;
an optical isomer or a pharmacologically acceptable salt thereof, a hydrate thereof or a solvate thereof with a solvent selected from the group consisting of methanol, ethanol, isopropanol, butanol, acetone, ethyl acetate and chloroform.

2. A compound as claimed in claim 1, wherein $R_1$ represents a $C_1$ to $C_6$ alkyl group; a $C_1$ to $C_5$ alkyl group substituted with at least one group selected from the group consisting of an unsubstituted or substituted aryl group, an unsubstituted or substituted heterocyclic ring group, an unsubstituted or substituted alkoxy group, and an unsubstituted or substituted $C_3$ to $C_6$ cycloalkyl group; a cyclopentyl group; a benzylpiperidyl group; a tetrahydrofuryl group; a dibenzocycloheptyl group; or an indanyl group.

3. A compound as claimed in claim 1, wherein $R_1$ represents a methyl group; a butyl group; a 2-methylpropyl group; a 2-ethylbutyl group; a $C_1$ to $C_5$ alkyl group substituted with a phenyl group, a pyridyl group, a naphthyl group, a methylthiazonyl group, a fluorophenyl group, a benzylpiperazinyl group, a benzylpiperidyl group, a benzyloxy group, a cyclopropylmethoxy group, or a $C_3$ to $C_6$ cycloalkyl group which may have a phenyl group; a cyclopentyl group; a benzylpiperidyl group; tetrahydrofuryl group; a dibenzocycloheptyl group; or a 2-indanyl group.

4. A compound as claimed in claim 1 or 2, wherein $R_2$ represents a methyl group.

5. A compound as claimed in claim 1, wherein $R_3$ represents a hydrogen atom; a $C_1$ to $C_4$ alkyl group; an aryl group which may be substituted with a halogen atom; a heteroaryl group; a $C_1$ to $C_3$ alkyl group substituted with a $C_4$ to $C_6$ cycloalkyl group containing at least one hetero atom selected from the group consisting of oxygen, nitrogen, and sulfur atoms; an ethyoxycarbonylmethyl group; or a benzoyl group.

6. A compound as claimed in claim 1, wherein $R_4$ represents a hydrogen atom, a $C_1$ to $C_4$ alkyl group, a phenyl group, a thiazolyl group, a thienyl group, or a pyridyl group.

7. A compound as claimed in claim 1, wherein $R_5$ and $R_6$ each independently represent a hydrogen atom, a methyl group, or a phenyl group.

8. A pharmaceutical composition comprising a compound according to claim 1 and a pharmacologically acceptable carrier.

9. A 6-phenyltetrahydro-1,3-oxazin-2-one derivative having the formula (I):

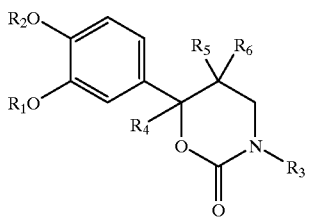

(I)

wherein:
$R_1$ represents a $C_1$ to $C_8$ alkyl group which may be substituted with one substituent, a $C_3$ to $C_7$ cycloalkyl group which may be substituted with one substituent, a 5- or 6-membered heterocyclic group containing at least one heteroatom selected from the group consisting of oxygen, nitrogen and sulfur atoms which may be substituted with one substituent, or a $C_9$ to $C_{15}$ bicyclic or tricyclic hydrocarbon;
$R_2$ represents a $C_1$ to $C_4$ alkyl group;
$R_3$ represents a hydrogen atom, a $C_1$ to $C_5$ alkyl group which may be substituted with one substituent, a $C_3$ to $C_7$ cycloalkyl group which may be substituted with one substituent, a $C_6$ to $C_{10}$ monocyclic or bicyclic aromatic group which may be substituted with one substituent, a 5- or 6-membered heteroaryl group containing at least one hetero atom selected from oxygen, nitrogen, and sulfur atoms which may be substituted with one substituent, or an acyl group;

$R_4$ represents a hydrogen atom, a $C_1$ to $C_6$ alkyl group which may be substituted with one substituent, a $C_6$ to $C_{10}$ monocyclic or bicyclic aromatic group which may be substituted with one substituent, or a 5- or 6-membered heteroaryl group containing at least one hetero atom selected from oxygen, nitrogen, and sulfur atoms which may be substituted with one substituent; and $R_5$ and $R_6$ each independently represent a hydrogen atom, a $C_1$ to $C_5$ alkyl group which may be substituted with one substituent, a $C_3$ to $C_7$ cycloalkyl group which may be substituted with one substituent, a $C_6$ to $C_{10}$ monocyclic or bicyclic aromatic group which may be substituted with one substituent, or a 5- or 6-membered heteroaryl group containing at least one hetero atom selected from oxygen, nitrogen, and sulfur atoms which may be substituted with one substituent;

an optical isomer or a pharmacologically acceptable salt thereof, a hydrate thereof or a solvate thereof with a solvent selected from the group consisting of methanol, ethanol, isopropanol, butanol, acetone, ethyl acetate and chloroform.

10. A compound as claimed in claim 9, wherein $R_1$ represents a $C_1$ to $C_6$ alkyl group, a cyclopentyl group, a benylpiperidyl group, a tetrahydrofuryl group, a dibenzocycloheptyl group an indanyl group, a $C_1$ to $C_5$ alkyl group substituted with at least one group selected from the group consisting of 5 to 10 membered monocyclic and bicyclic heterocyclic groups containing at least one hetero atom selected from the group consisting of oxygen, nitrogen, and sulfur atoms which may be substituted with one substituent, an alkoxy group which may be substituted with one substituent, a $C_3$ to $C_6$ cycloalkyl group which may be substituted with one substituent, and a $C_6$ to $C_{10}$ monocyclic or bicyclic aromatic group which may be substituted with one substituent.

11. A compound as claimed in claim 9, wherein $R_1$ represents a methyl group, a butyl group, a 2-methyl-propyl group, a 2-ethyl butyl group, a cyclopentyl group, a benzylpiperidyl group, a tetrahydrofuryl group, a dibenzylcycloheptyl group, a 2-indanyl group, or a $C_1$ to $C_5$ alkyl group substituted with a phenyl group, a pyridyl group, a naphthyl group, a methylthiazolyl group, a fluorophenyl group, a benzylpiperazinyl group, a benzylpiperyl group, a benzyloxy group, a cyclopropylmethoxy group, or a $C_3$ to $C_6$ cycloalkyl group which may have a phenyl group.

12. A compound as claimed in claim 9, wherein $R_2$ represents a methyl group.

13. A compound as claimed in claim 9, wherein $R_3$ represents a hydrogen atom; a $C_1$ to $C_4$ alkyl group; an ethyoxycarbonylmethyl group; a benzoyl group; or a $C_1$ to $C_3$ alkyl group, substituted with one group selected from the group consisting of (1) a $C_6$ to $C_{10}$ monocyclic or bicyclic aromatic group which may be substituted with one substituent, (2) a 5 to 10 membered monocyclic or bicyclic heteroaryl group containing at least one hetero atom selected from the group consisting of oxygen, nitrogen, and sulfur atoms which may be substituted with one substituent, and (3) a $C_4$ to $C_6$ cycloalkyl group containing at least one hetero atom selected from the group consisting of oxygen, nitrogen, and sulfur atoms.

14. A compound as claimed in claim 9, wherein $R_4$ represents a hydrogen atom, a $C_1$ to $C_4$ alkyl group, a phenyl group, a thiazolyl group, a thienyl group, or a pyridyl group.

15. A compound as claimed in claim 9, wherein $R_5$ and $R_6$ each independently represent a hydrogen atom, a methyl group, or a phenyl group.

16. A pharmaceutical composition comprising a compound according to claim 9 and a pharmacologically acceptable carrier.

17. A method for treating dermatitis in a patient comprising administering a therapeutically effective amount of a pharmaceutical composition according to claim 8.

18. A method for treating dermatitis in a patient comprising administering a therapeutically effective amount of a pharmaceutical composition according to claim 16.

19. A method for treating asthma in a patient comprising administering a therapeutically effective amount of a pharmaceutical composition according to claim 8.

20. A method for treating asthma in a patient comprising administering a therapeutically effective amount of a pharmaceutical composition according to claim 16.

* * * * *

UNITED STATES PATENT AND TRADEMARK OFFICE
CERTIFICATE OF CORRECTION

PATENT NO. : 6,251,897 B1
DATED : June 26, 2001
INVENTOR(S) : Shinji Ina, Kenjirou Yamana and Kyoji Noda It is certified that error appears in the above-identified patent and that said Letters Patent is hereby corrected as shown below:

<u>Title page,</u>
Item [56], FOREIGN PATENT DOCUMENTS, replace "6-17777  1/1994  (JP)." with
-- 6-1777   1/1994  (JP). --.
Item [57], ABSTRACT,
Lines 3-4, after the formula, replace "cycloalkyl group;, etc.," with -- cycloalkyl group, etc.; --.
Line 4, after the formula, replace "alkyl group; etc.," with -- alkyl group, ect.; --.
Line 7, after the formula, replace "alkyl group; etc." with -- alkyl group, etc.; --.
Line 15, after the formula, replace "antiinflammatory" with -- anti-inflammatory --.

<u>Column 77,</u>
Line 30, replace "ethyoxycarbonylmethyl" with -- ethoxycarbonylmethyl --.

<u>Column 78,</u>
Line 31, replace "benylpiperidyl" with -- benzylpiperidyl --.
Line 50, replace "benzylpiperyl" with -- benzylpiperidyl --.
Line 57, replace "ethyoxycarbonylmethyl" with -- ethoxycarbonylmethyl --.

Signed and Sealed this

Fifth Day of November, 2002

*Attest:*

*Attesting Officer*

JAMES E. ROGAN
*Director of the United States Patent and Trademark Office*